United States Patent
Amano et al.

(10) Patent No.: US 6,293,915 B1
(45) Date of Patent: *Sep. 25, 2001

(54) PULSE WAVE EXAMINATION APPARATUS, BLOOD PRESSURE MONITOR, PULSE WAVEFORM MONITOR, AND PHARMACOLOGICAL ACTION MONITOR

(75) Inventors: Kazuhiko Amano; Kazuo Uebaba, both of Yokohama; Hitoshi Ishiyama, Toride; Hiroshi Kasahara, Kashiwa, all of (JP)

(73) Assignee: Seiko Epson Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/341,787

(22) PCT Filed: Nov. 20, 1998

(86) PCT No.: PCT/JP98/05259

§ 371 Date: Jul. 16, 1999

§ 102(e) Date: Jul. 16, 1999

(87) PCT Pub. No.: WO99/26529

PCT Pub. Date: Jun. 3, 1999

(30) Foreign Application Priority Data

Nov. 20, 1997 (JP) .................................................. 9-320149
Nov. 21, 1997 (JP) .................................................. 9-321768
Jul. 12, 1998 (JP) .................................................. 10-213494

(51) Int. Cl.[7] ...................................................... A61B 5/02
(52) U.S. Cl. ........................... 600/501; 600/500; 600/485
(58) Field of Search ................................... 600/500, 501, 600/485, 486, 502

(56) References Cited

U.S. PATENT DOCUMENTS 5,623,933 * 4/1997 Amano et al. ...................... 600/500
5,755,229 * 5/1998 Amano et al. ...................... 600/500

FOREIGN PATENT DOCUMENTS

| 0 638 281 A1 | 2/1995 | (EP) . |
|---|---|---|
| 59-189830 | 10/1984 | (JP) . |
| 4-250132 | 9/1992 | (JP) . |
| 8-257000 | 10/1996 | (JP) . |
| 8-289876 | 11/1996 | (JP) . |
| 9-135819 | 5/1997 | (JP) . |
| 139440 | 8/1990 | (TW) . |
| WO96 35368 | 11/1996 | (WO) . |

OTHER PUBLICATIONS

"Medical Diagnostics, vol. 1 (in Japanese)", supervised by Akira Shibata, Mar., 10, 1995, Nishimura Shoten, pp401–409.

"Application of Wavelet Transformation to Wave Pulse of Living Body (in Japanese)", Preprint of 15th Scientific Lectures on Biomechanism, (Japan), (1994), pp121–124.

* cited by examiner

Primary Examiner—Cary O'Connor
Assistant Examiner—Navin Natnithithadha

(57) ABSTRACT

An FFT treating section (40) carries out the frequency analysis of a pulse waveform MHj excluding a body movement component to yield pulse wave analysis data MKD and then a tidal wave-character extracting section (50) and a dicrotic wave-character extracting section (60) yield a tidal wave-character data (TWD) and a dicrotic wave-character data (DWD) showing the characteristics of a tidal wave and dicrotic wave respectively. Then, a pulse condition judging section (70) yields pulse condition data (ZD) on the basis of this data (TWD, DWD) and in succession a notifying section (80) advises of the pulse condition of a subject.

61 Claims, 56 Drawing Sheets

WAVELET ANALYSIS RESULT

PING MAI

XUAN MAI

FIG. 14

|  | HUA MAI | PING MAI | XUAN MAI |
|---|---|---|---|
| AMPLITUDE OF DICROTIC WAVE [mmHG] | 7.3 | 10.6 | 2.9 |
| AMPLITUDE OF TIDAL WAVE [mmHG] | 0 | 0 | 3.8 |

FIG. 15

|  | HUA MAI | PING MAI | XUAN MAI |
|---|---|---|---|
| FUNDAMENTAL WAVE | 100.0 | 100.0 | 100.0 |
| 2 | 75.5 | 66.0 | 47.9 |
| 3 | 67.8 | 64.3 | 45.5 |
| 4 | 30.6 | 20.1 | 25.0 |
| 5 | 21.1 | 15.9 | 17.6 |
| 6 | 11.1 | 5.4 | 16.8 |
| 7 | 3.5 | 4.3 | 7.1 |
| 8 | 2.0 | 5.3 | 4.9 |
| 9 | 2.0 | 3.0 | 6.5 |
| 10 | 3.0 | 3.6 | 5.1 |

FIG. 28

| | t1 | t2 | t3 | t4 | t5 | t6 | t7 | t8 |
|---|---|---|---|---|---|---|---|---|
| 4.0~3.5Hz | 8 | 4 | 6 | 0 | 0 | 0 | 0 | 0 |
| 3.5~3.0Hz | 5 | 2 | 3 | 1 | 0 | 0 | 0 | 0 |
| 3.0~2.5Hz | 2 | 1 | 4 | 0 | 0 | 0 | 0 | 0 |
| 2.5~2.0Hz | 1 | 1 | 3 | 0 | 1 | 0 | 0 | 1 |
| 2.0~1.5Hz | 2 | 3 | 1 | 1 | 1 | 0 | 0 | 1 |
| 1.5~1.0Hz | 4 | 5 | 5 | 5 | 5 | 6 | 5 | 4 |
| 1.0~0.5Hz | 4 | 7 | 8 | 8 | 6 | 8 | 8 | 8 |
| 0.5~0.0Hz | 6 | 7 | 7 | 10 | 10 | 9 | 9 | 9 |

FIG. 29

| | t1 | t2 | t3 | t4 | t5 | t6 | t7 | t8 |
|---|---|---|---|---|---|---|---|---|
| 4.0~3.5Hz | 0 | 0 | 0 | 0 | 0 | 0 | 0 | 0 |
| 3.5~3.0Hz | 0 | 0 | 0 | 0 | 0 | 0 | 0 | 0 |
| 3.0~2.5Hz | 0 | 0 | 0 | 0 | 0 | 0 | 0 | 0 |
| 2.5~2.0Hz | 0 | 0 | 0 | 0 | 0 | 0 | 0 | 0 |
| 2.0~1.5Hz | 0 | 0 | 0 | 0 | 0 | 1 | 0 | 0 |
| 1.5~1.0Hz | 0 | 1 | 1 | 0 | 0 | 2 | 1 | 0 |
| 1.0~0.5Hz | 4 | 5 | 7 | 7 | 5 | 6 | 6 | 7 |
| 0.5~0.0Hz | 5 | 6 | 6 | 6 | 7 | 6 | 6 | 6 |

FIG. 30

| | t1 | t2 | t3 | t4 | t5 | t6 | t7 | t8 |
|---|---|---|---|---|---|---|---|---|
| 4.0~3.5Hz | 8 | 4 | 6 | 0 | 0 | 0 | 0 | 0 |
| 3.5~3.0Hz | 5 | 2 | 3 | 1 | 0 | 0 | 0 | 0 |
| 3.0~2.5Hz | 2 | 1 | 4 | 0 | 0 | 0 | 0 | 0 |
| 2.5~2.0Hz | 1 | 1 | 3 | 0 | 1 | 0 | 0 | 0 |
| 2.0~1.5Hz | 2 | 3 | 1 | 1 | 1 | 0 | 0 | 1 |
| 1.5~1.0Hz | 4 | 4 | 4 | 5 | 5 | 4 | 4 | 4 |
| 1.0~0.5Hz | 0 | 2 | 1 | 1 | 1 | 2 | 2 | 1 |
| 0.5~0.0Hz | 1 | 1 | 1 | 4 | 3 | 3 | 3 | 3 |

| | t1 | t2 | t3 | t4 | t5 | t6 | t7 | t8 |
|---|---|---|---|---|---|---|---|---|
| 4.0~3.5Hz | 8 | 4 | 6 | 0 | 0 | 0 | 0 | 0 |
| 3.5~3.0Hz | 5 | 2 | 3 | 1 | 0 | 0 | 0 | 0 |
| 3.0~2.5Hz | 2 | 1 | 4 | 0 | 0 | 0 | 0 | 0 |
| 2.5~2.0Hz | 1 | 1 | 3 | 0 | 1 | 0 | 0 | 1 |
| 2.0~1.5Hz | 2 | 3 | 1 | 1 | 1 | 0 | 0 | 1 |
| 1.5~1.0Hz | 4 | 5 | 5 | 5 | 5 | 6 | 5 | 4 |
| 1.0~0.5Hz | 0 | 0 | 0 | 0 | 0 | 0 | 0 | 0 |
| 0.5~0.0Hz | 0 | 0 | 0 | 0 | 0 | 0 | 0 | 0 |

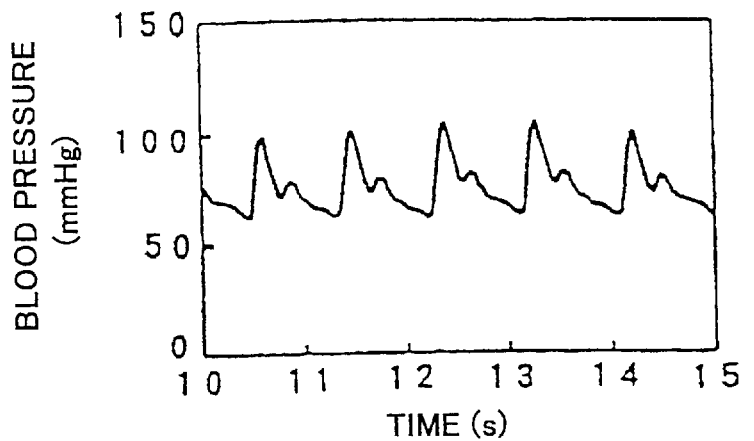
FIG. 45A — PING MAI
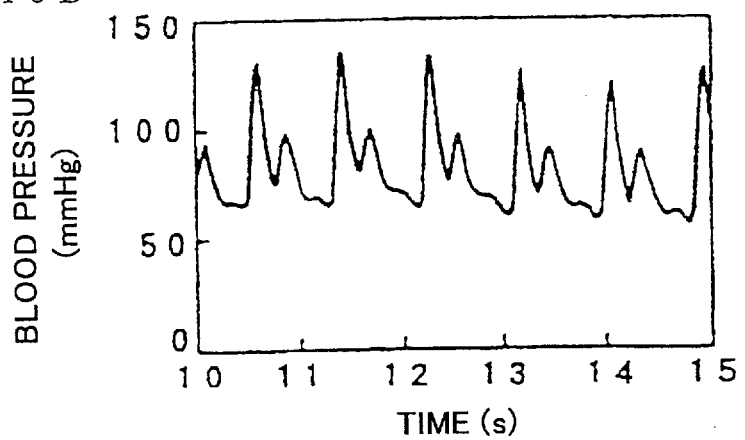
FIG. 45B — HUA MAI
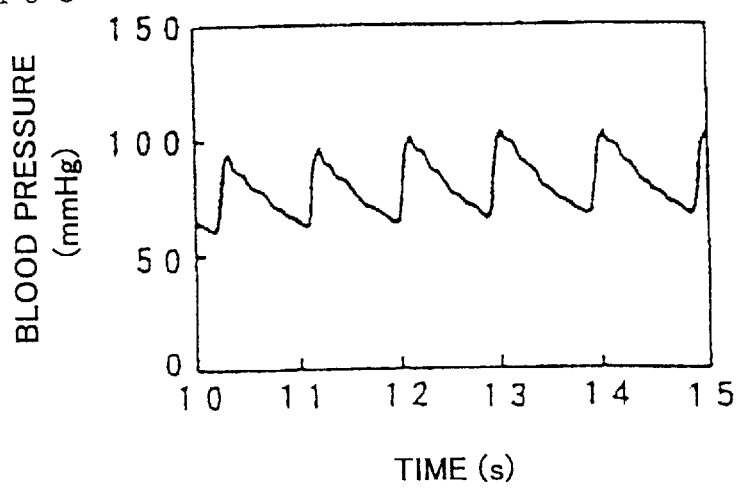
FIG. 45C — XUAN MAI

PULSE WAVE EXAMINATION APPARATUS, BLOOD PRESSURE MONITOR, PULSE WAVEFORM MONITOR, AND PHARMACOLOGICAL ACTION MONITOR

TECHNICAL FIELD

The present invention relates to a pulse wave examination apparatus suitable for specifying the type of human pulse wave, a blood pressure monitor using the mean blood pressure and pulse pressure as its parameters and a pulse waveform monitor and a pharmacological action monitor which use a parameter related to a dicrotic notch part of an arterial pressure waveform.

BACKGROUND ART

The pulse wave is usually defined as a wave of blood which is output from the heart and propagates through a blood vessel. For this reason, it is known that various types of medical information can be obtained by the detection of pulse wave and analysis of the detected pulse wave. with the progress of studies on the pulse wave, it has become clear that various types of information, not obtainable only from the blood pressure and the pulse rate, can be obtained by analyzing the pulse wave, collected from the human body, by various techniques, making a diagnosis possible on the basis of these types of information.

The inventors of the present invention remarked the relation between the pulse waveform and its distortion rate in PCT/JP96/01254 (Title of the Invention: DIAGNOSTIC APPARATUS FOR DETECTING CONDITION OF LIVING BODY AND CONTROLLER) and made it possible to diagnose the living condition of a subject by detecting and treating the pulse waveform of the subject, calculating the distortion rate of the waveform and specifying the waveform from the distortion rate.

Here, the relationship between a pulse waveform and a distortion rate which are mentioned in the above application will be described briefly.

First, there are various types of pulse waveforms and the forms are diversified. Here, typical forms of pulse waveforms by the classification of Chinese medicine which is one of a traditional oriental medicine will be described. FIGS. 45A to 45C are the charts showing representative pulse waveforms by this classification.

The pulse waveform shown in FIG. 45A is called a "Ping mai" which is the pulse condition of a normal man in good health. This "Ping mai" is characterized in that, as shown in the figure, the pulse is relaxed, and exhibits a constant rhythm without disruption.

Secondly, the pulse waveform shown in FIG. 45B is called a "Hua mai" which is the pulse condition of a man who shows an abnormality in his blood stream condition. The waveform of a Hua mai exhibits a sharp, rapid rise, and then falls off immediately, the aortic dicrotic notch is deep and at the same time the subsequent peak is considerably higher than that of a Ping mai. It is considered that diseases such as a mammary tumor, liver or kidney ailment, respiratory ailment, stomach or intestinal ailment or inflammation, or some other illness cause the movement of the blood to be very fluent and smooth, which causes this "Hua mai".

Moreover, the pulse waveform shown in FIG. 45C is called a "Xuan mai" which is the pulse condition of a man whose blood vessel wall tension has increased. The Xuan mai is characterized in that its waveform rises steeply and remains at a high pressure state for a fixed period of time without an immediate drop. This "Xuan mai" is seen in diseases such as liver and gall ailments, dermatological ailments, high blood pressure, and pain ailments. It is believed that tension in the automatic nervous system causes the walls of the blood vessels to constrict, decreasing elasticity, so that the effect of the blood pulsation of the pumped blood is not readily expressed, causing this phenomenon.

The ordinate and the abscissa in the graphs of FIGS. 45A to 45C show blood pressure (mmHg) and time (second) respectively.

The relationship between the pulse condition of the pulse waveform and its distortion rated is shown in FIG. 46. Here, the distortion rate d of the pulse waveform is determined by the following equation (1):

$$d = \frac{\sqrt{A_2^2 + A_3^2 + \cdots + A_n^2}}{A_1} \quad (1)$$

wherein $A_1$ is the amplitude of a basic wave component in the pulse wave and $A_2, A_3, \ldots, A_n$ are the amplitudes of the second, third, . . . and nth harmonic components respectively.

It is therefore possible to specify the pulse condition of the pulse waveform quantitatively from the correlation shown in FIG. 46 if the pulse waveform of a subject is detected and the detected waveform is subjected to FFT (Fourier transformation) treatment to find the amplitudes $A_1$ to $A_n$ from which the distortion rate d is calculated.

As shown in FIG. 46, when the pulse condition of the subject is judged to be a Hua mai, the distortion rate d is in a range between 0.98 and 1.22. When the pulse condition is judged to be a Ping mai, the distortion rate d is in a range between 0.92 and 1.10. When the pulse condition is judged to be a Xuan mai, the distortion rate d is in a range between 0.73 and 0.94.

In this case, the pulse condition can be judged to be a Hua mai or a Ping mai when the distortion rate d of the pulse waveform is in a range between 0.98 and 1.10. Also, the pulse condition can be judged to be a Ping mai or a Xuan mai when the distortion rate d of the pulse waveform is in a range between 0.92 and 0.94. It is therefore difficult to judge the pulse condition precisely by a conventional pulse wave examination apparatus.

In the meantime, a blood pressure gauge measuring a maximum blood pressure and a minimum blood pressure and displaying these pressures is used in noninvasive detection of blood pressure.

Although the maximum blood pressures or minimum pressures of subjects are alike, there are various types of waveforms for blood pressure. Hence the characteristics of the blood pressure of an individual expressed only by a maximum blood pressure and a minimum blood pressure are insufficient.

The mean blood pressure is an important parameter for knowing the condition of the blood pressure of an individual. The mean blood pressure cannot be obtained only by measurements of a maximum blood pressure and minimum blood pressure.

In sphygmic detection adopted in Chinese medicine or in Indian traditional medicine, a medical examination is carried out by examining the pulse waveform detected by the fingers when a medical examiner presses with an optimum pressing force against a distal position of the forearm from the arteria radialis, that is, a medical examination is conducted by detection of a variation with the pressing force, which variation is felt by the fingers of the medical examiner corresponding to a variation in blood pressure.

In Chinese medicine, for instance, the pulse waveform felt when a proper pressing force is applied to the arteria radialis is roughly divided into three categories, which are designated as a "Ping mai", "Hua mai" and "Xuan mai" respectively as aforementioned. The Ping mai is deliberate and mild and its rhythm is stable and reduced in turbulence. This Ping mai is a pulse image for a man in good health. The Hua mai is the type in which the flow of the pulse is felt to be very fluent and smooth, showing abnormality in the blood stream condition. The Xuan mai is felt to be a straight, tense and long pulse and is regarded to be due to tension or aging of a blood vessel wall.

Such a medical examination method, however, is dependent upon the pulse waveform classified by the sense of the medical examiner posing problems with regard to its objectivity and reproducibility.

The present invention has been conducted in the above situation and has an object of providing a pulse wave examination apparatus which can judge the pulse condition objectively and accurately.

Another object of the present invention is to provide a blood pressure monitor which can indicate blood conditions in more detail than the information of a maximum and minimum blood pressure and can monitor the monitor parameters signifying blood pressure noninvasively.

A further object of the present invention is to provide a pulse waveform monitor which can carry out an examination by the pulse waveform objectively and reproducibly.

DISCLOSURE OF THE INVENTION (1) A pulse wave examination apparatus according to the present invention comprises:
  a pulse wave detecting means for detecting a pulse waveform from a living body;
  a tidal wave-character extracting means for extracting the characteristics of a tidal wave from the pulse waveform to yield tidal wave-character information;
  a dicrotic wave-character extracting means for extracting the characteristics of a dicrotic wave from the pulse waveform to yield dicrotic wave-character information; and
  a pulse condition judging means for judging the pulse condition of the living body on the basis of the tidal wave-character information and the dicrotic wave-character information.

(2) In the pulse wave examination apparatus according to (1), preferably the tidal wave-character extracting means yields the tidal wave-character information on the basis of a variation in the amplitude in the time-domain of the tidal wave, and the dicrotic wave-character extracting means yields the dicrotic wave-character information on the basis of a variation in the amplitude in the time-domain of the dicrotic wave.

(3) In the pulse wave examination apparatus according to (2), preferably the variations in the amplitude in the time-domain of the tidal wave and the dicrotic wave are calculated from the primary or secondary time derivative of the pulse waveform.

(4) A pulse wave examination apparatus according to the present invention comprises:
  a pulse wave detecting means for detecting a pulse waveform from a living body;
  a frequency analyzing means for performing a frequency analysis of the pulse waveform;
  a tidal wave-character extracting means for extracting the characteristics of a tidal wave from the result of the analysis of the frequency analyzing means to yield tidal wave-character information;
  a dicrotic wave-character extracting means for extracting the characteristics of a dicrotic wave from the result of the analysis of the frequency analyzing means to yield dicrotic wave-character information; and
  a pulse condition judging means for judging the pulse condition of the living body on the basis of the tidal wave-character information and the dicrotic wave-character information.

(5) In the pulse wave examination apparatus according to (4), preferably the tidal wave-character information extracting means specifies a period of the tidal wave in the pulse waveform and extracts the characteristics of the tidal wave from the tidal waveform on the basis of the result of the analysis of the frequency analyzing means in the period of the tidal wave to yield tidal wave-character information, and the dicrotic wave-character information extracting means specifies a period of the dicrotic wave in the pulse waveform and extracts the characteristics of the dicrotic wave from the tidal waveform on the basis of the result of the analysis of the frequency analyzing means in the period of the dicrotic wave to yield dicrotic wave-character information.

(6) In the pulse wave examination apparatus according to (4) or (5), preferably the frequency analyzing means performs FFT treatment of the pulse waveform.

(7) In the pulse wave examination apparatus according to (4) or (5), preferably the frequency analyzing means performs wavelet transformation treatment of the pulse waveform.

(8) The pulse wave examination apparatus according to any one of (1) to (7), preferably further comprises a notification means for communicating the pulse condition judged by the pulse condition judging means.

(9) A pulse wave examination apparatus according to the present invention comprises:
  a pulse wave detecting means for detecting a pulse waveform from the detecting position of a living body;
  a auto-correlation calculating means for calculating auto-correlation data giving the auto-correlation of the pulse waveform detected by the pulse wave detecting means; and
  a pulse condition-data yielding means for yielding pulse condition data giving the type of pulse waveform based on the auto-correlation data.

(10) In the pulse wave examination apparatus according to (9), preferably the pulse condition-data yielding means produces the pulse condition data by comparing the auto-correlation data with a prescribed threshold value.

(11) In the pulse wave examination apparatus according to (10), preferably the pulse condition-data yielding means comprises a minimum value detecting section for detecting the minimum value of the auto-correlation data during a period of one heart beat, and a comparing section for comparing the minimum value, detected by the minimum value detecting section, with the threshold value to yield the pulse condition data.

(12) In the pulse wave examination apparatus according to (10), preferably the pulse condition-data yielding means comprises a minimum value detecting section for detecting an average minimum value by averaging each minimum value of the auto-correlation data detected in each of plural heart beat periods, and a comparing section for comparing the average minimum value, detected by the minimum value detecting section, with the threshold value to yield the pulse condition data.

(13) In the pulse wave examination apparatus according to (9), preferably the pulse condition-data yielding means comprises: a time measuring section for comparing the auto-correlation data with a prescribed threshold value to measure a time interval in which the auto-correlation data exceeds or is less than the threshold value; a calculating section for calculating the ratio of the time interval, measured by the time measuring section, to a period of one heart beat; and a comparing section for comparing the result, calculated by the calculating section, with a prescribed threshold value to yield the pulse condition data.

(14) In the pulse wave examination apparatus according to (13), preferably the calculating section calculates the ratio of the time interval, measured by the time measuring section, to a period of one heart beat and calculates the average of the calculated results.

(15) In the pulse wave examination apparatus according to (9), preferably the pulse condition-data yielding means comprises a change rate calculating section for detecting the change rate of the auto-correlation data on the basis of the auto-correlation data, and a change rate comparing section for comparing the change rate, detected by the change rate calculating section, with a prescribed threshold value to yield the pulse condition data.

(16) In the pulse wave examination apparatus according to (15), preferably the change rate comparing section detects a maximum value of the change rate and compares the maximum value of the change rate with the threshold value to yield the pulse condition data.

(17) In the pulse wave examination apparatus according to (9), preferably the pulse condition data yielding means comprises:
- a minimum value detecting section for detecting the minimum value of the auto-correlation data in a period of one heart beat;
- a first comparing section for comparing the minimum value, detected by the minimum value detecting section, with a prescribed first threshold value to yield pulse condition data indicating a Xuan mai when the minimum value is less than the first threshold value;
- a time measuring section for comparing the auto-correlation data with a prescribed second threshold value to measure a time interval in which the auto-correlation data exceeds or is less than the second threshold value;
- a calculating section for calculating the ratio of the time interval, measured by the time measuring section, to a period of one heart beat; and
- a second comparing section for comparing the result, calculated by the calculating section, with a prescribed third threshold value to yield the pulse condition data indicating a Ping mai or a Hua mai.

(18) In the pulse wave examination apparatus according to (9), preferably the pulse condition data yielding means comprises:
- a minimum value detecting section for detecting the minimum value of the auto-correlation data in a period of one heart beat;
- a first comparing section for comparing the minimum value, detected by the minimum value detecting section, with the first threshold value to yield pulse condition data indicating a Xuan mai when the minimum value is less than the threshold value;
- a variation calculating section for detecting a change rate of the auto-correlation data on the basis of the auto-correlation data; and
- a second comparing section for comparing the change rate, calculated by the change rate calculating section, with a prescribed threshold value to yield the pulse condition data indicating a Ping mai or a Hua mai.

(19) In the pulse wave examination apparatus according to (17) or (18), preferably the auto-correlation data is a coefficient of auto-correlation and the first threshold value used in the comparing operation performed in the first comparing section is 0.25 approximately.

(20) In the pulse wave examination apparatus according to (17), preferably the auto-correlation data is a coefficient of auto-correlation and the second threshold value used in the comparing operation performed in the time measuring section is designed to be in a range between 0.4 and 0.8.

(21) The pulse wave examination apparatus according to any one of (9) to (20), preferably further comprises;
- a body movement detecting means for detecting the waveform of the body movement indicating the body movement of the living body; and
- a body movement-component eliminating means for eliminating a body movement component from the pulse waveform to yield a body movement-removed pulse waveform, said body movement component in the pulse waveform generated on the basis of the body movement waveform;
- wherein the auto-correlation calculating means calculates auto-correlation data giving auto-correlation on the basis of the body movement-removed pulse waveform in place of the pulse waveform.

(22) The pulse wave examination apparatus according to (21), preferably further comprises judging means for judging the presence of body movement of the living body on the basis of the body movement waveform detected by the body movement detecting means,
- wherein the body movement-component eliminating means stops the body movement eliminating operation when the judging means shows the absence of body movement to output the pulse waveform in place of the body movement-removed pulse waveform.

(23) The pulse wave examination apparatus according to any one of (9) to (20), preferably further comprises:
- a first wavelet transformation means for performing wavelet transformation of the pulse waveform to yield pulse wave analysis data for every frequency zone;
- a body movement detecting means for detecting the movement of the living body to output the waveform of the body movement;
- a second wavelet transformation means for performing wavelet transformation of the waveform of the body movement detected by the body movement detecting means to yield body movement analysis data for every frequency zone;
- a body movement component eliminating means for subtracting the body movement analysis data from the pulse wave analysis data to yield body movement-eliminated pulse wave analysis data; and
- an inverse wavelet transformation means for performing inverse wavelet transformation of the body movement-eliminated pulse wave analysis data to yield a body movement-eliminated pulse waveform;
- wherein the auto-correlation calculating means calculates auto-correlation data giving auto-correlation on the basis of the body movement-eliminated pulse waveform in place of the pulse waveform.

(24) The pulse wave examination apparatus according to any one of (9) to (20), preferably further comprises:

a wavelet transformation means for performing wavelet transformation of the pulse waveform detected by the pulse waveform detecting means to yield pulse wave analysis data for every frequency zone;

a body movement component eliminating means for eliminating a prescribed frequency component corresponding to a body movement among the pulse wave analysis data to yield body movement-eliminated pulse wave analysis data; and an inverse wavelet transformation means for performing inverse wavelet transformation of the body movement-eliminated pulse wave analysis data to yield a body movement-eliminated pulse waveform;

wherein the auto-correlation calculating means calculates auto-correlation data giving auto-correlation on the basis of the body movement-eliminated pulse wave analysis data in place of the pulse waveform.

(25) A pulse wave examination apparatus according to the present invention comprises:

a pulse wave detecting means for detecting a pulse waveform from the detecting position of a living body;

a wavelet transformation means for performing wavelet transformation of the pulse waveform detected by the pulse wave detecting means to yield pulse wave analysis data for every frequency zone;

an auto-correlation calculating means for calculating auto-correlation data giving auto-correlation of the pulse wave analysis data in a given frequency zone; and a pulse condition data yielding means for yielding a pulse condition data giving the type of pulse waveform on the basis of the auto-correlation data.

(26) A pulse wave examination apparatus according to the present invention comprises:

a pulse wave detecting means for detecting a pulse waveform from the detecting position of a living body;

a first wavelet transformation means for performing wavelet transformation of the pulse waveform detected by the pulse wave detecting means to yield pulse wave analysis data for every frequency zone;

a body movement detecting means for detecting the movement of the living body to output the waveform of the body movement;

a second wavelet transformation means for performing wavelet transformation of the waveform of the body movement detected by the body movement detecting means to yield body movement analysis data for every frequency zone;

a body movement component eliminating means for subtracting the body movement analysis data from the pulse wave analysis data to yield body movement-eliminated pulse wave analysis data; and an auto-correlation calculating means for calculating auto-correlation data giving auto-correlation of the body movement-eliminated pulse wave analysis data in a given frequency zone; and a pulse condition data yielding means for yielding pulse condition data giving the type of pulse waveform on the basis of the auto-correlation data.

(27) A pulse wave examination apparatus according to the present invention comprises:

a pulse wave detecting means for detecting a pulse waveform from the detecting position of a living body;

a wavelet transformation means for performing wavelet transformation of the pulse waveform detected by the pulse wave detecting means to yield pulse wave analysis data for every frequency zone;

a body movement component eliminating means for eliminating a prescribed frequency component corresponding to a body movement to yield body movement-eliminated pulse wave analysis data;

an auto-correlation calculating means for calculating auto-correlation data giving auto-correlation of the body movement-eliminated pulse wave analysis data in a given frequency zone; and a pulse condition data yielding means for yielding a pulse condition data giving the type of pulse waveform on the basis of the auto-correlation data.

(28) The pulse wave examination apparatus according to any one of (9) to (27), preferably further comprise a notification means for communicating the pulse condition data yielded by the pulse condition data yielding means.

(29) A blood pressure monitor according to the present invention comprises:

an arterial pressure waveform detecting section for measuring blood pressure in an artery continuously to detect a waveform of arterial pressure; and a mean blood pressure calculating section for calculating the mean blood pressure on the basis of the waveform of arterial pressure.

The blood pressure monitor of the present invention comprises the mean blood pressure calculating section for calculating the mean blood pressure on the basis of the waveform of arterial pressure detected by the arterial pressure waveform detecting section. Therefore the mean blood pressure can be monitored using the waveform of arterial pressure detected by the arterial pressure waveform detecting section.

(30) The blood pressure monitor according to (29), preferably further comprises a pulse pressure calculating section for calculating pulse pressure which is a pressure difference between a maximum blood pressure and a minimum blood pressure on the basis of the waveform of arterial pressure.

According to the invention, the pulse pressure can be monitored using the waveform of arterial pressure detected by the arterial pressure waveform detecting section.

(31) The blood pressure monitor according to (30), preferably further comprises a blood pressure conversion section for converting the waveform of arterial pressure detected by the arterial pressure waveform detecting section into the waveform of cardiac-position arterial pressure which is a waveform of arterial pressure at a position corresponding to the altitude of a heart;

wherein the mean blood pressure calculating section calculates the mean blood pressure on the basis of the waveform of cardiac-position arterial pressure; and wherein the pulse pressure calculating section calculates the pulse pressure on the basis of the waveform of cardiac-position arterial pressure.

According to the invention, the waveform of arterial pressure detected by the arterial pressure waveform detecting section is converted into the waveform of cardiac-position arterial pressure, which is a waveform of arterial pressure at a position corresponding to the altitude of an artery, by the blood pressure conversion section. Then,based on the waveform of cardiac-position arterial pressure, the mean blood pressure calculating section calculates the mean blood pressure and the pulse pressure calculating section calculates the pulse pressure. At least either one of the mean blood pressure and the pulse pressure in an artery at a position corresponding to the altitude of an artery can be monitored using the waveform of arterial pressure detected by the arterial pressure waveform detecting section.

(32) The blood pressure monitor according to (30) or (31), preferably further comprises:

a blood pressure-judging information storing section for storing blood pressure-judging information in advance; and a blood pressure judging section for judging blood pressure on the basis of at least either one of the mean blood pressure and the pulse pressure and on the blood pressure-judging information.

According to the invention, the blood pressure monitor can determine whether the blood pressure is high, low, or normal on the basis of at least either one of the resulting mean blood pressure and pulse pressure and on the blood pressure-judging information stored in advance.

(33) The blood pressure monitor according to any one of (30) and (32), preferably further comprises an output section for outputting at least one piece of information corresponding to the mean blood pressure, to the pulse pressure and to the blood pressure judgment.

According to the invention, at least one piece of information corresponding to the mean blood pressure, to the pulse pressure and to the blood pressure judgment can be output by the output section in the form of, for instance, numerals, graphs or voltages.

(34) A blood pressure monitor according to the present invention comprises:

an arterial pressure waveform detecting section for continuously measuring blood pressure in an artery to detect a waveform of arterial pressure; and a pulse pressure calculating section for calculating pulse pressure, which is a pressure difference between a maximum blood pressure and a minimum blood pressure, on the basis of the waveform of arterial pressure.

According to the invention, the pulse pressure can be monitored using the waveform of arterial pressure detected by the arterial pressure waveform detecting section.

(35) The blood pressure monitor according to (34), preferably further comprises:

a maximum blood pressure calculating section for calculating a maximum blood pressure on the basis of the pulse pressure; and a minimum blood pressure calculating section for calculating a minimum blood pressure on the basis of the pulse pressure and the maximum blood pressure.

According to the invention, the maximum blood pressure calculating section determines a maximum blood pressure by making use of the fact that the maximum blood pressure can be given by a linear function of pulse pressure. Also, since the pulse pressure is a pressure difference between a maximum pressure and a minimum pressure, the minimum blood pressure calculating section can determine a minimum blood pressure if a maximum blood pressure and pulse pressure are clarified.

(36) A pulse waveform monitor according to the present invention comprises:

an arterial pressure waveform detecting section for continuously measuring blood pressure in an artery to detect a waveform of arterial pressure; and a dicrotic wave height calculating section for calculating a dicrotic wave height which is a difference in blood pressure between a dicrotic notch and a peak of a dicrotic wave which are obtained from the waveform of arterial pressure.

According to the invention, the pulse waveform monitor can calculate a dicrotic wave height on the basis of the waveform of arterial pressure obtained by continuously measuring blood pressure in an artery by using the arterial pressure waveform detecting section.

(37) The pulse waveform monitor according to (36), preferably further comprises a dicrotic pressure difference ratio calculating section for calculating, based on the waveform of arterial pressure, the ratio of a dicrotic pressure difference, which is a pressure difference between blood pressure at a dicrotic notch and a minimum blood pressure, to a pulse pressure which is a pressure difference between a maximum blood pressure and a minimum blood pressure.

According to the invention, the pulse waveform monitor can calculate a dicrotic wave height and the ratio of a dicrotic pressure difference on the basis of the waveform of arterial pressure obtained by continuously measuring blood pressure in an artery by using the arterial pressure waveform detecting section.

(38) The pulse waveform monitor according to (37), preferably further comprises a mean blood pressure-pulse pressure ratio calculating section for calculating, based on the waveform of arterial pressure, the ratio of the mean blood pressure to pulse pressure which is a pressure difference between a maximum blood pressure and a minimum blood pressure.

According to the invention, the pulse waveform monitor can calculate a dicrotic wave height, the ratio of a dicrotic pressure difference, and the mean blood pressure-pulse pressure ratio on the basis of the waveform of arterial pressure obtained by continuously measuring blood pressure in an artery by using the arterial pressure waveform detecting section.

(39) The pulse waveform monitor according to (38), preferably further comprises a blood pressure conversion section for converting the waveform of arterial pressure detected by the arterial pressure waveform detecting section into the waveform of cardiac-position arterial pressure which is a waveform of arterial pressure at a position corresponding to the altitude of a heart;

wherein the dicrotic wave height calculating section calculates, based on the waveform of cardiac-position arterial pressure, a dicrotic wave height which is a pressure difference in blood pressure between a dicrotic notch and a peak of a dicrotic wave;

wherein the dicrotic pressure difference ratio calculating section calculates, based on the cardiac-position arterial pressure, the ratio of a dicrotic pressure difference, which is a pressure difference between blood pressure at a dicrotic notch and a minimum blood pressure, to a pulse pressure which is a pressure difference between a maximum blood pressure and a minimum blood pressure; and wherein the mean blood pressure-pulse pressure ratio calculating section calculates, based on the waveform of arterial pressure, the ratio of the mean blood pressure to a pulse pressure which is a pressure difference between a maximum blood pressure and a minimum blood pressure.

According to the invention, the waveform of arterial pressure detected by the arterial pressure waveform detecting section is converted into the waveform of cardiac-position arterial pressure, which is a waveform of arterial pressure at a position corresponding to the altitude of an artery, by the blood pressure conversion section. Then, based on the cardiac-position arterial pressure, the dicrotic wave height calculating section calculates a dicrotic wave height, the dicrotic pressure difference ratio calculating section calculates the dicrotic pressure difference ratio, and the mean blood pressure-pulse pressure ratio calculating section calculates the mean blood pressure-pulse pressure ratio. Hence, using the waveform of arterial pressure detected by the arterial pressure waveform detecting section, at least one of the dicrotic wave height, dicrotic pressure difference ratio and mean blood pressure-pulse pressure ratio can be monitored.

(40) The pulse waveform monitor according to (36), preferably further comprises:
 a pulse waveform-judging information storing section for storing pulse waveform-judging information in advance; and
 a pulse waveform judging section for judging the waveform of a pulse wave on the basis of the dicrotic wave height and the pulse waveform-judging information.

According to the invention, the pulse wave judging section can judge the pulse waveform on the basis of the dicrotic wave height and the pulse waveform-judging information.

(41) The pulse waveform monitor according to (37), preferably further comprises:
 a pulse waveform-judging information storing section for storing pulse waveform-judging information in advance; and
 a pulse waveform judging section for judging the pulse waveform on the basis of the dicrotic wave height, the dicrotic pressure difference ratio and the pulse waveform-judging information.

According to the invention, the pulse wave judging section can judge the pulse waveform on the basis of the dicrotic wave height, the dicrotic pressure difference ratio and the pulse waveform-judging information.

(42) The pulse waveform monitor according to (38), preferably further comprises:
 a pulse waveform-judging information storing section for storing pulse waveform-judging information in advance; and
 a pulse waveform judging section for judging the pulse waveform on the basis of the dicrotic wave height, the dicrotic pressure difference ratio, the mean blood pressure-pulse pressure ratio, and the pulse waveform-judging information.

According to the invention, the pulse wave judging section can judge the pulse waveform on the basis of the dicrotic wave height, the dicrotic pressure difference ratio, the mean blood pressure-pulse wave ratio, and the pulse waveform-judging information.

(43) The pulse waveform monitor according to (36), preferably further comprises an output section for outputting at least one piece of information corresponding to the dicrotic wave height and to the pulse waveform.

According to the invention, at least one piece of information corresponding to the information corresponding to the dicrotic wave height, and to the pulse waveform can be output by the output section in the form of, for instance, numerals, graphs or voltages.

(44) The pulse waveform monitor according to (37), preferably further comprises an output section for outputting at least one piece of information corresponding to the dicrotic wave height, to the dicrotic pressure difference ratio and to the pulse waveform.

According to the invention, the pulse waveform monitor can output at least one piece of information corresponding to the dicrotic wave height, to the dicrotic pressure difference ratio, and to the pulse waveform from the output section in the form of, for instance, numerals, graphs or voltages.

(45) The pulse waveform monitor according to (38), preferably further comprises an output section for outputting at least one piece of information corresponding to the dicrotic wave height, to the dicrotic pressure difference ratio, to the mean blood pressure-pulse pressure ratio and to the pulse waveform.

According to the invention, the pulse waveform monitor can output at least one piece of information corresponding to the dicrotic wave height, to the dicrotic pressure difference ratio, to the mean blood pressure-pulse wave ratio, and to the pulse waveform from the output section in the form of, for instance, numerals, graphs or voltages.

(46) A pulse waveform monitor according to the present invention comprises:
 a pulse waveform detecting section for detecting the pulse waveform from a living body; and
 a dicrotic pressure difference ratio calculating section for calculating, based on the pulse waveform, the dicrotic pressure difference ratio, which is a pressure difference between a dicrotic pressure and a minimum pressure, to a pulse pressure which is a pressure difference between a maximum pressure and a minimum pressure.

This aspect differs from the aspect according to (36) in that the dicrotic pressure difference ratio calculating section does not need an absolute value of blood pressure to calculate the ratio. In the aspect, therefore, the arterial pressure waveform detecting section used in (36) may be replaced by a pulse wave detecting section for detecting only a pulse wave which is a waveform corresponding to that in (36).

(47) A pulse waveform monitor according to the present invention comprises:
 a pulse waveform detecting section for detecting a pulse waveform from a living body; and
 a mean pressure-pulse pressure ratio calculating section for calculating, based on the pulse waveform, the ratio of the mean pressure to pulse pressure which is a pressure difference between a maximum pressure and a minimum pressure.

This aspect differs from the aspect according to (16) in that the mean blood pressure-pulse pressure ratio calculating section does not need an absolute value of blood pressure to calculate the ratio. In this aspect, therefore, the arterial pressure waveform detecting section used in (16) may be replaced by a pulse wave detecting section for detecting only a pulse wave which is a waveform corresponding to that in (16).

(48) A blood pressure monitor according to the present invention comprises:
 an arterial pressure waveform detecting section for measuring blood pressure in an artery continuously to detect a waveform of arterial pressure;
 a mean blood pressure calculating section for calculating the mean blood pressure on the basis of the waveform of arterial pressure; and
 a dicrotic wave height calculating section for calculating, based on the waveform of arterial pressure, the dicrotic wave height which is a difference in blood pressure between a dicrotic notch and a peak of a dicrotic wave.

(49) A blood pressure monitor according to the present invention comprises:
 an arterial pressure waveform detecting section for continuously measuring blood pressure in an artery to detect a waveform of arterial pressure;

a mean blood pressure calculating section for calculating the mean blood pressure on the basis of the waveform of arterial pressure; and a dicrotic pressure difference ratio calculating section for calculating, based on the waveform of arterial pressure, the dicrotic pressure difference ratio which is the ratio of a dicrotic pressure difference, which is a pressure difference between blood pressure at a dicrotic notch and a minimum blood pressure, to a pulse pressure which is a pressure difference between a maximum blood pressure and a minimum blood pressure.

(50) A blood pressure monitor according to the present invention comprises:

an arterial pressure waveform detecting section for continuously measuring blood pressure in an artery to detect a waveform of arterial pressure;

a mean blood pressure calculating section for calculating the mean blood pressure on the basis of the waveform of arterial pressure; and a mean blood pressure-pulse pressure ratio calculating section for calculating, based on the waveform of arterial pressure, the ratio of the mean blood pressure to a pulse pressure which is a pressure difference between a maximum blood pressure and a minimum blood pressure.

(51) A blood pressure monitor according to the present invention comprises:

an arterial pressure waveform detecting section for measuring blood pressure in an artery continuously to detect a waveform of arterial pressure;

a pulse pressure calculating section for calculating pulse pressure, which is the pressure difference between the maximum blood pressure and the minimum blood pressure, on the basis of the waveform of arterial pressure; and a dicrotic wave height calculating section for calculating, based on the waveform of arterial pressure, the dicrotic wave height which is a difference in blood pressure between a dicrotic notch and a peak of a dicrotic wave.

(52) A blood pressure monitor according to the present invention comprises:

an arterial pressure waveform detecting section for measuring blood pressure in an artery continuously to detect a waveform of arterial pressure;

a pulse pressure calculating section for calculating pulse pressure, which is the pressure difference between the maximum blood pressure and the minimum blood pressure, on the basis of the waveform of arterial pressure; and a dicrotic pressure difference ratio calculating section for calculating, based on the waveform of arterial pressure, the dicrotic pressure difference ratio which is the ratio of a dicrotic pressure difference, which is a pressure difference between a dicrotic blood pressure and a minimum blood pressure, to a pulse pressure which is a pressure difference between a maximum blood pressure and a minimum blood pressure.

(53) A blood pressure monitor according to the present invention comprises:

an arterial pressure waveform detecting section for measuring blood pressure in an artery continuously to detect a waveform of arterial pressure;

a pulse pressure calculating section for calculating pulse pressure, which is the pressure difference between the maximum blood pressure and the minimum blood pressure, on the basis of the waveform of arterial pressure; and a mean blood pressure-pulse pressure ratio calculating section for calculating, based on the waveform of arterial pressure, the ratio of the mean blood pressure to a pulse pressure which is a pressure difference between a maximum blood pressure and a minimum blood pressure.

(54) A pulse waveform monitor according to the present invention comprises:

an arterial pressure waveform detecting section for continuously measuring blood pressure in an artery to detect a waveform of arterial pressure; and an ejection diastolic pressure calculating section for calculating, based on the waveform of arterial pressure, ejection diastolic pressure which is a pressure difference between a systolic blood pressure and a dicrotic blood pressure.

(55) The pulse waveform monitor according to (54), preferably further comprises:

a pulse waveform-judging information storing section for storing pulse waveform-judging information in advance; and a pulse waveform judging section for judging the pulse waveform on the basis of the ejection diastolic pressure and the pulse waveform-judging information.

(56) A pulse waveform monitor according to the present invention comprises:

a pulse wave detecting section for detecting a pulse waveform from a living body; and an ejection diastolic pressure ratio calculating section for calculating, based on the pulse waveform, the ratio of ejection diastolic pressure, which is a pressure difference between systolic pressure and dicrotic pressure, to pulse pressure which is a pressure difference between systolic pressure and diastolic pressure.

(57) The pulse waveform monitor according to (56), preferably further comprises:

a pulse waveform-judging information storing section for storing pulse waveform-judging information in advance; and a pulse waveform judging section for judging the pulse waveform on the basis of the ejection diastolic pressure ratio and the pulse waveform judging information.

(58) A pharmacological action monitor according to the present invention comprises:

an arterial pressure waveform detecting section for measuring blood pressure in an artery continuously to detect a waveform of arterial pressure; and and the pulse waveform judging information.

an ejection diastolic pressure calculating section for calculating, based on the waveform of arterial pressure, ejection diastolic pressure which is a pressure difference between systolic blood pressure and dicrotic blood pressure.

(59) The pharmacological action monitor according to (58), preferably further comprises a dicrotic wave height calculating section for calculating, based on the waveform of arterial pressure, a dicrotic wave height which is the blood pressure difference between a dicrotic notch and a peak of a dicrotic wave.

(60) A pharmacological action monitor according to the present invention comprises:

a pulse wave detecting section for detecting a pulse waveform from a living body; and an ejection diastolic pressure ratio calculating section for calculating the ejection diastolic pressure ratio which is the ratio of the ejection diastolic pressure, which is a pressure difference between systolic pressure and dicrotic pressure, to a pulse pressure which is a pressure difference between the diastolic pressure and the systolic pressure.

(61) The pharmacological action monitor according to (60), preferably further comprises a dicrotic wave height calculating section for calculating, based on the pulse waveform, a dicrotic wave height ratio which is the ratio of a dicrotic wave height, which is the difference in pressure between a dicrotic notch and a peak of a dicrotic wave, to pulse pressure which is a pressure difference between systolic pressure and diastolic pressure.

BRIEF DESCRIPTION OF THE DRAWINGS

FIG. 14 is a table showing the amplitudes of a tidal wave and dicrotic wave for each pulse condition.

FIG. 15 is a table showing a harmonic component of each pulse condition.

FIG. 28 is a view showing amended data MKDa of a pulse wave during the period Tc in the sixth embodiment.

FIG. 29 is a view showing body movement-amended data TKDa during the period Tc in the sixth embodiment.

FIG. 30 is a view showing body movement-eliminating pulse wave data MKDaj excluding a body movement component in the sixth embodiment.

FIG. 45A is a view showing the pulse waveform of a typical Ping mai.

FIG. 45B is a view showing the pulse waveform of a typical Hua mai.

FIG. 45C is a view showing the pulse waveform of a typical Xuan mai.

BEST MODE FOR CARRYING OUT THE INVENTION

1. First Embodiment

A pulse wave examination apparatus according to a first embodiment of the present invention will be described below.

1.1 Theoretical Basis for the First Embodiment

Needless to say, the heart ejects blood by repeated contractions and dilatations. Here, the time of causing blood to flow from the heart by a contraction/dilatation in one cycle is called "ejection time". When the pulse rate, which is the number of contractions of the heart per unit time, is increased by, for instance, exercise, a catecholamine, e.g., adrenaline, is liberated, with the result that the ejection time tends to be short. This implies an increase in the contraction force of the heart muscle.

With increased ejection time, the output of blood by the contraction/dilatation in one cycle tends to increase.

Meanwhile, when a person exercises, it is necessary to supply much oxygen to the heart muscle, the skeletal muscle and the like, hence the product of the pulse rate and the output, that is, the flow rate of blood (per unit time) ejected from the heart increases. As a result of the increased pulse rate, the ejection time is short and the output is small. However, since the rate of increase in the pulse rate exceeds the rate of decrease in the output, the product of the pulse rate and the output increases on the whole.

Next, description of the relationship between the movement of the heart and the waveform of the blood pressure will be given. In the electrocardiogram shown in FIG. 8, generally the period from the R point to the terminal point U of the T wave is said to be "a ventricular systole", which corresponds to the foregoing ejection time. The period from the U point to the next R point is said to be "a ventricular diastole". In the ventricular systole, a ventricular contraction does not take place uniformly but proceeds at a slow pace as it spreads from the outside to the inside. Because of this, the waveform of the blood pressure at the proximal portion of an aorta has an upwardly convex form as shown in FIG. 8 in the ventricular systole ranging from the opening to the closing of the aortic valve.

Figure 8:
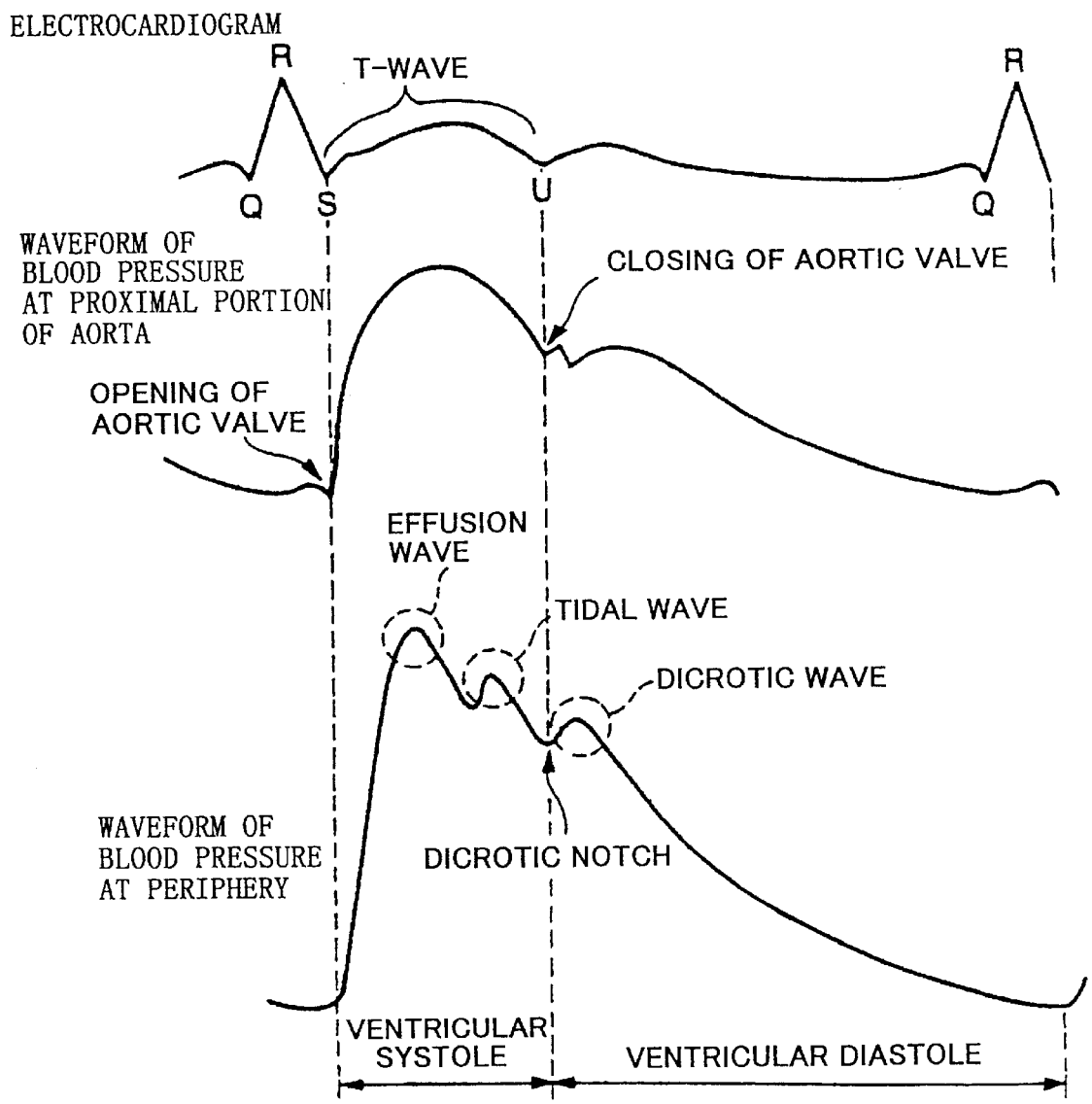
FIG. 8 is a view showing an electrocardiographic waveform, a waveform of arterial pressure and a waveform of blood pressure at a peripheral part in correspondence to each other.

The waveform of the blood pressure at the periphery (arteria radialis) corresponding to such a blood waveform at the proximal portion of an aorta, that is, the pulse waveform at the periphery is as shown in FIG. 8. The reason why such a waveform is formed is considered that a first wave called an "ejection wave" occurs by the ejection of blood from the heart, a second wave called a "tidal wave" successively occurs due to a reflex at furcations of the blood vessel close to the heart, and a third wave called a "dicrotic wave" then occurs due to the occurrence of a dicrotic notch concomitant with the closing of the aortic valve.

In the pulse waveform, therefore, the range from the point at which the blood pressure reach a minimum to the dicrotic notch corresponds to the ventricular systole, and the range from the dicrotic notch to the point at which the blood pressure reaches a minimum in the next cycle corresponds to the ventricular diastole.

Here, the point corresponding to the opening of the aortic valve in the pulse waveform is the minimum minimal point of blood pressure. Also, the point, specifically, the dicrotic notch, corresponding to the closing of the aortic valve is the third minimal point from the minimum minimal point viewing from time series and the second minimal point from the minimum minimal point viewing from the magnitude of the blood pressure.

Incidentally, the waveform of the peripheral blood pressure shown in FIG. 8, namely, the pulse waveform actually exhibits time delay with respect to the waveform of aortic blood pressure. However, in the figure, this time delay is neglected for the sake of simplicity and these phases are made to be uniform.

Next, the waveform of peripheral blood pressure, namely, the pulse waveform will be discussed. The pulse wave form detected at the peripheries of a subject is the so-called pattern of the pressure wave of blood which propagates through a closed system consisting of the heart as a pulsatile pump and the blood circulatory system as a conduit. Hence, first, the pulse wave form is regulated by the pumping function of the heart, namely, by the condition of a cardiac function. Second, the pulse wave form is affected, for example, by the diameter of a blood vessel, contraction/dilatation of a blood vessel, and viscous resistance of blood. It is considered that if the pulse waveform is detected to analyze it, the condition of the cardiac function of the subject as well as the aortic condition of the subject can be evaluated. It may be understood that specialists in Oriental medicine diagnose a living condition by the features of pulsation.

Now, a discussion will follow in which a portion is analyzed in the pulse waveform.

Figure 9:
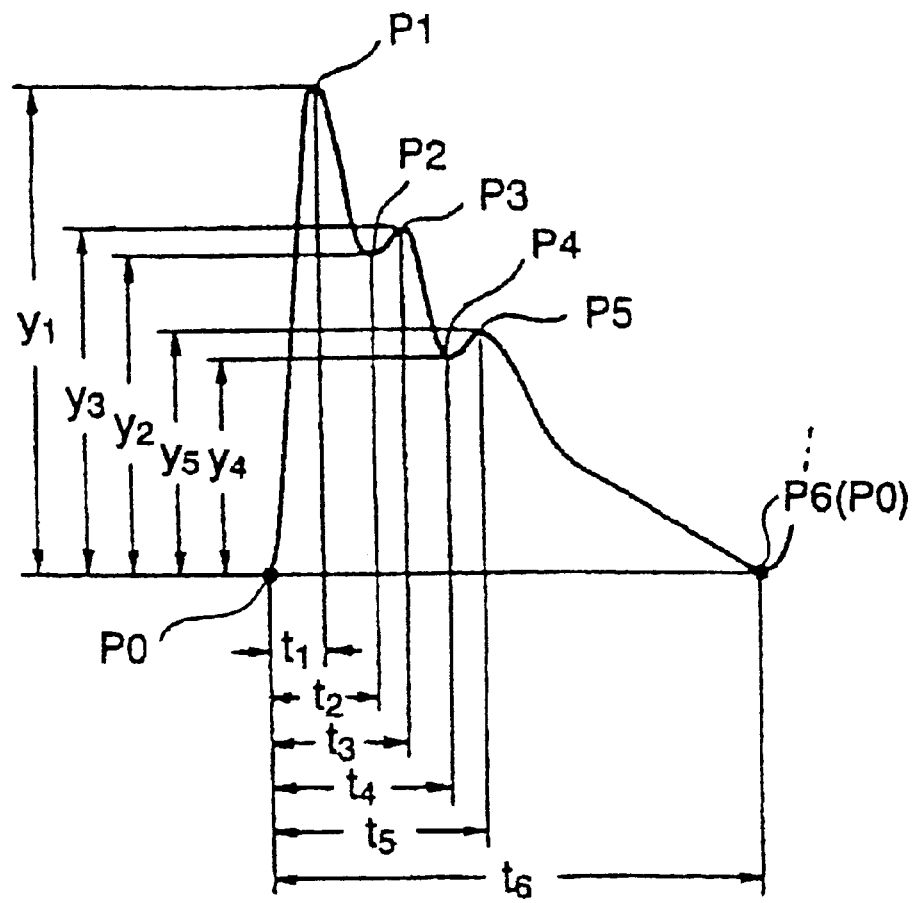
FIG. 9 is a view for describing the relationship between pulse waveform and waveform parameters.

First the inventors of the present invention selected the parameters shown in FIG. 9 as those which determine the features of the pulse waveform. Specifically, the selected parameters are as follows:

(1) a time $t_6$ between a peak point P0 (the minimum minimal point) of the ascending slope of one beat, at which point the value of the blood pressure in the pulse waveform reaches a minimum, and a peak point P6 of the ascending slope of the next pulse;

(2) the values of the blood pressure (difference) $y_1$ to $y_5$ at a peak points (maximal points and minimal points) which appear sequentially in the pulse wave form; and (3) time passages $t_1$ to $t_5$ from the peak point P0 (the minimum minimal point) at the pulse wave starting point to the point at which each of peak points P1 to P5 appear respectively.

In this case, each of $y_1$ to $y_5$ denotes a relative value of blood pressure by setting the value of the blood pressure at a peak point P0 as a datum.

The inventors of the present invention actually detected the pulse waves of 74 healthy adults between the ages of 22 and 46. The waveform parameters of these pulse waves were calculated while each pulse waveform was subjected to FFT treatment as in the aforementioned PCT/JP96/01254 to calculate the distortion rate d of the pulse waveform by using the foregoing equation (1).

Figure 10:
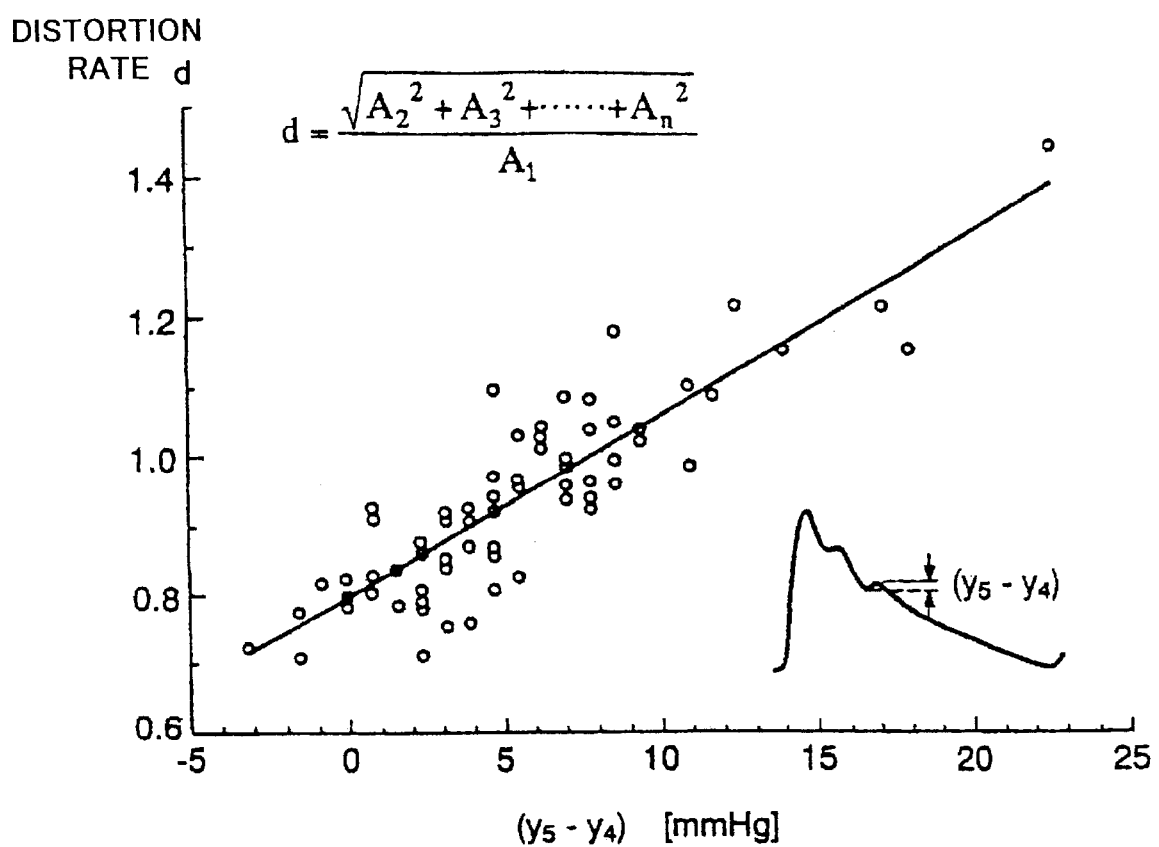
FIG. 10 is a view showing the relationship between a difference in blood pressures ($y_5$–$y_4$) and a distortion rate d.

Then the inventors of the present invention investigated the correlation between the calculated distortion rate d and each waveform parameter or the differences between these parameters separately. As a result, it was clarified that the distortion rate d had a high correlation with the pressure differences ($y_5$–$y_4$) in the values of blood pressure, which difference was the amplitude of a dicrotic wave from the dicrotic notch, with the coefficient of correlation ($R^2$) being 0.77. This correlation is shown in FIG. 10.

From this fact, the inventors of the present invention made the following analysis on the hypothesis that specialists in Oriental medicine sensed the features of the dicrotic wave and tidal wave to diagnose the pulse condition.

Figure 11:
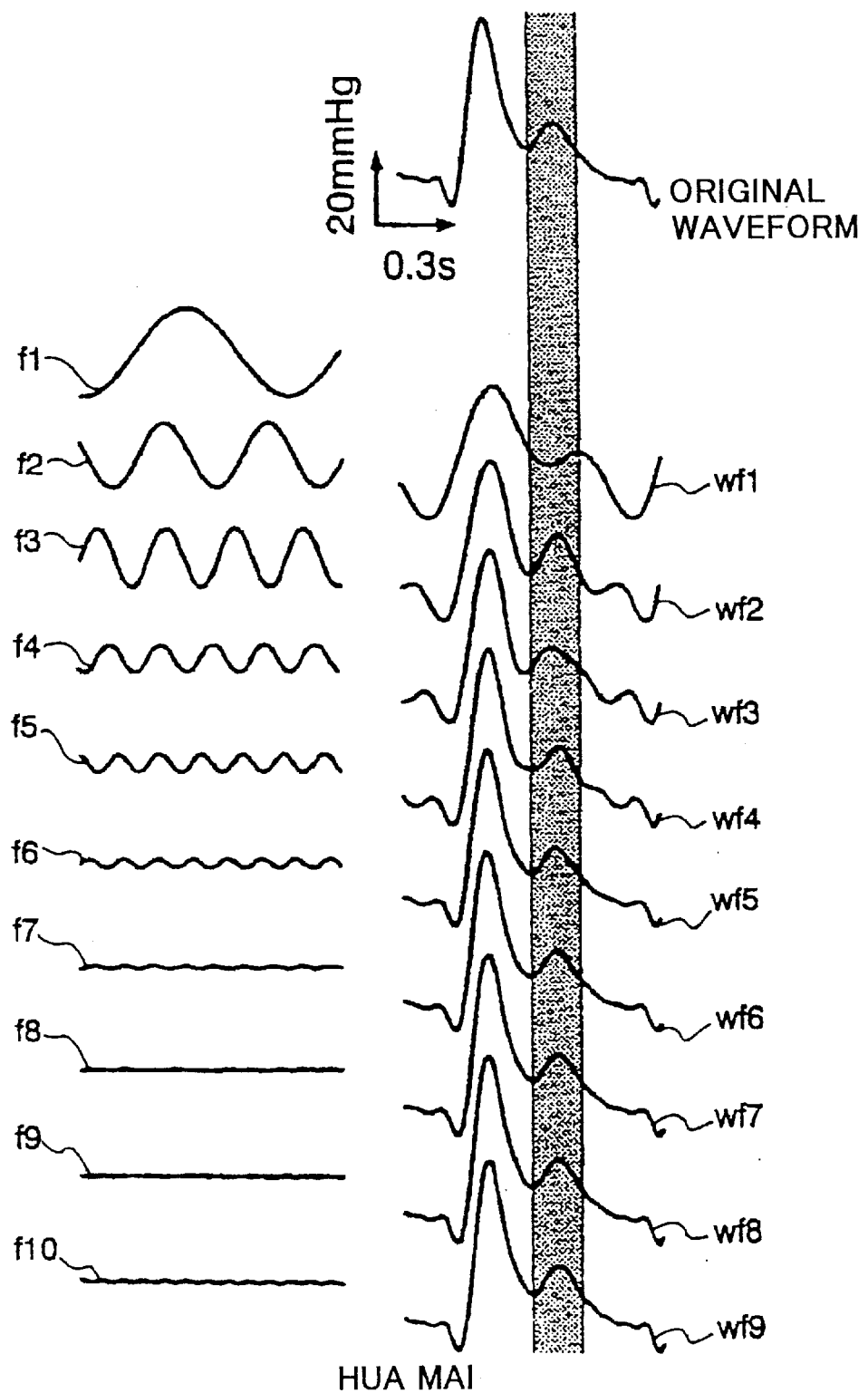
FIG. 11 is a view showing the result of frequency analysis of a Hua mai.
Figure 12:
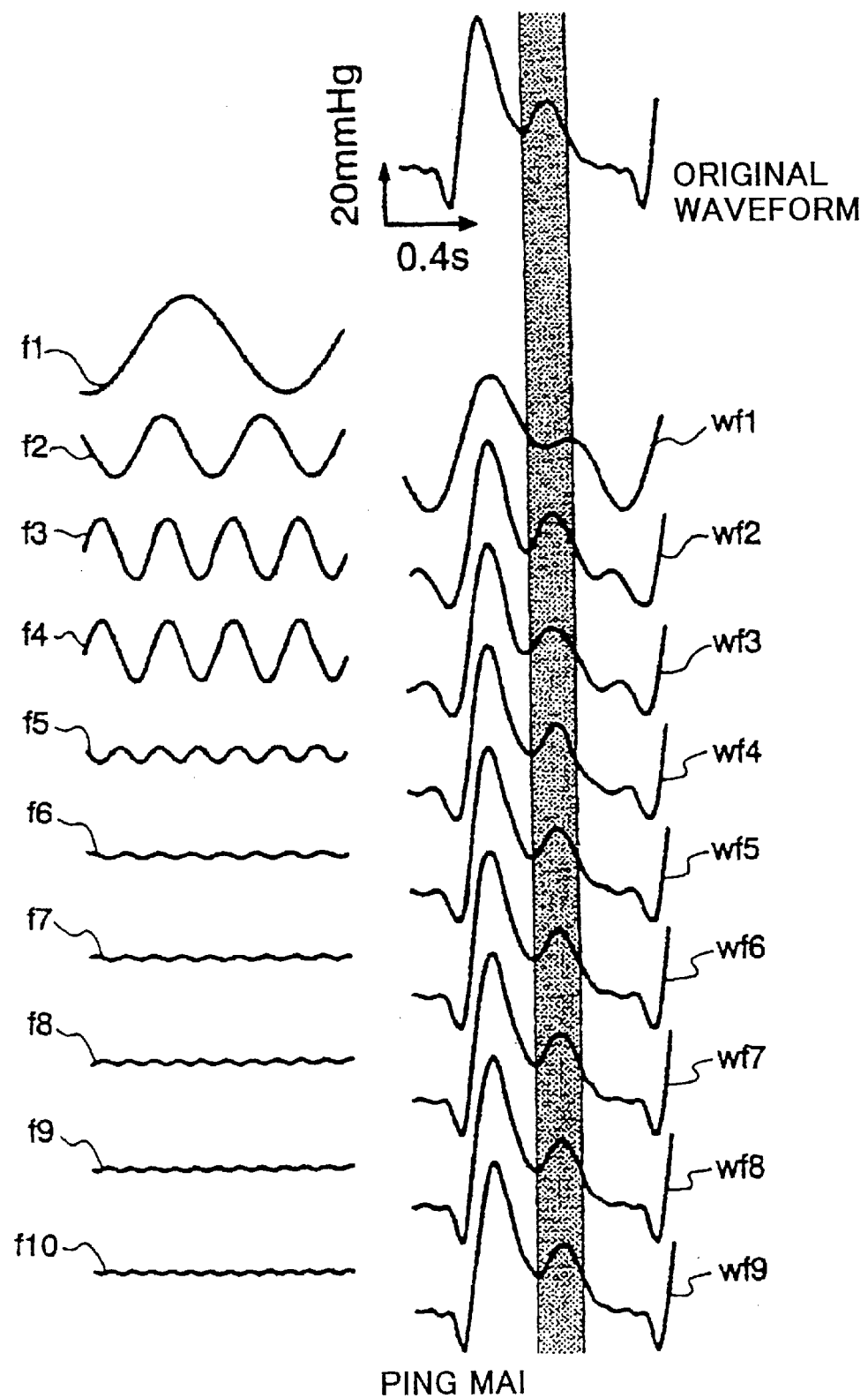
FIG. 12 is a view showing the result of frequency analysis of a Ping mai.
Figure 13:
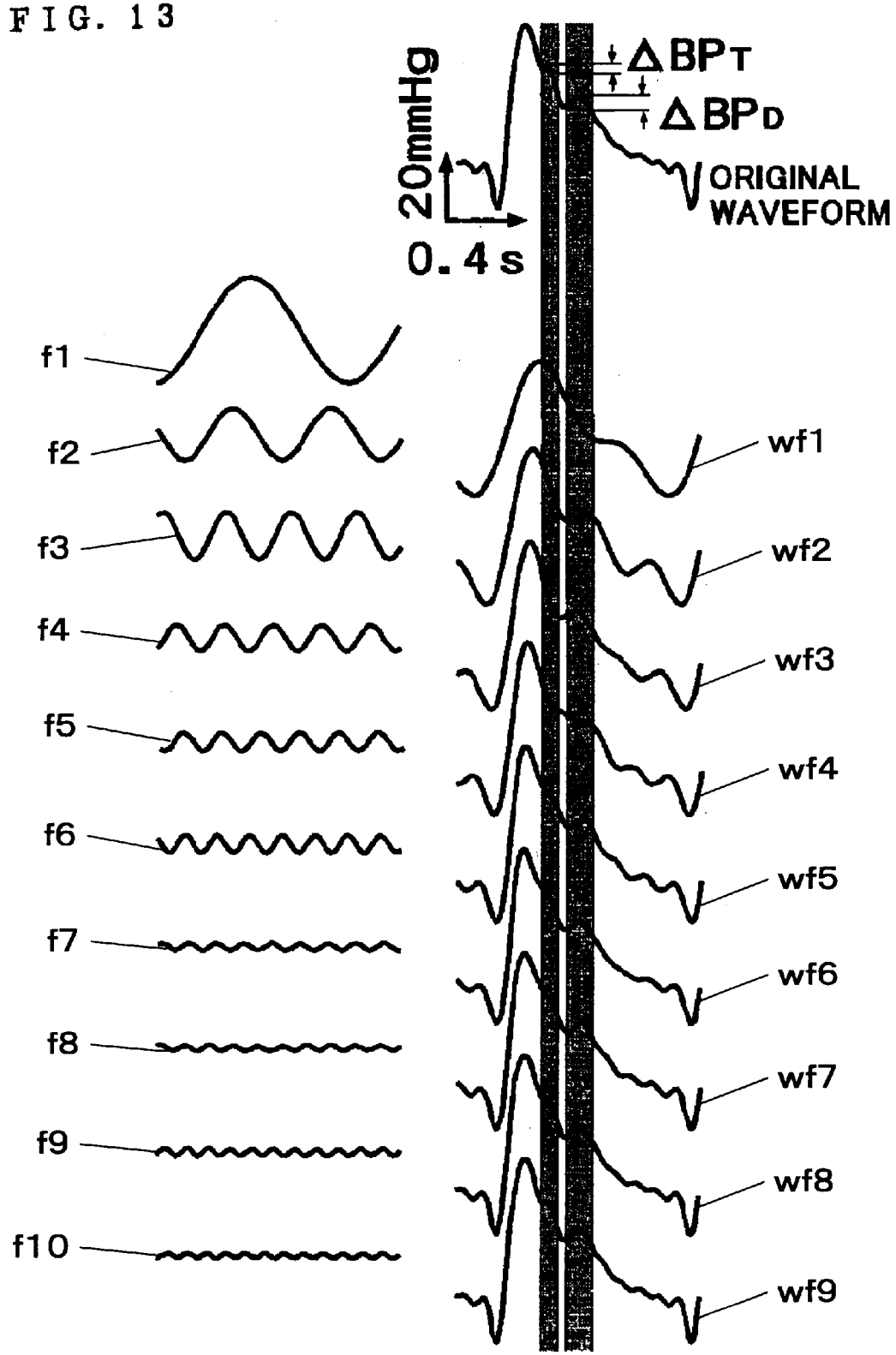
FIG. 13 is a view showing the result of frequency analysis of a Xuan mai.

In this analysis, each pulse waveform which was judged for the pulse condition by specialists in Oriental medicine was subjected to FFT treatment to calculate the ratio of each harmonic component to a fundamental wave component. FIGS. 11, 12 and 13 show the results of analysis of a Hua mai, Ping mai and Xuan mai respectively.

In FIGS. 11 to 13, f1, f2, f3, , f10 indicate the amplitudes and phases of a fundamental wave, second harmonic, third harmonic, . . . , tenth harmonic respectively. The waveform wf1 is the sum of the fundamental wave f1 and the second harmonic f2, waveform wf2 is the sum of the fundamental wave f1 to the third harmonic, . . . , and the waveform wf9 is the sum of the fundamental wave f1 to the tenth harmonic f10.

Here, comparing the original waveform shown in FIG. 11, whose pulse condition was judged to be a Hua mai by the specialist, with the original waveform shown in FIG. 12, whose pulse condition was judged to be a Ping mai by the specialists, it is understood that both closely resemble one another but the height of the dicrotic notch is lower in a Hua mai than in a Ping mai and the amplitude of the dicrotic wave is larger in a Ping mai than in a Hua mai. When attention is given to the synthesized waveform, it is understood that each original waveform of the dicrotic waves of a Hua mai and Ping mai is almost reproduced by the waveform wf3 which is the sum of the fundamental wave f1 to the third harmonic f4.

On the other hand, in a Xuan mai as shown in FIG. 13, it is understood that the original waveform of the tidal wave is almost reproduced by the waveform wf6 which is the sum of the fundamental wave f1 to the seventh harmonic f7.

FIG. 14 shows the amplitudes of the dicrotic wave and the tidal wave in the pulse waveform representing the pulse condition which is described in FIGS. 11 to 13. The amplitudes of the dicrotic waves are relatively as high as 7.3 mmHg and 10.6 mmHg in a Hua mai and in a Ping mai respectively whereas the amplitude of the dicrotic wave in a Xuan mai is as small as 2.9 mmHg. The amplitudes of the tidal waves in a Hua mai and in a Ping mai are 0 whereas the amplitude of the tidal wave in a Xuan mai is 3.8 mmHg.

From these facts, in a Hua mai and Ping mai, each dicrotic wave has specific characteristics which are observed in the fundamental wave f1 to the fourth harmonic f4. In a Xuan mai, the tidal wave has specific characteristics which are observed in high frequency components, e.g., the fifth harmonic f5 to the seventh harmonic f7.

Next, FIG. 15 shows the percentage ratio of the amplitude of each harmonic to the amplitude of the fundamental wave for every pulse condition. Here, when attention is given to the ratio of the sum of the second harmonic f2, the third harmonic f3, and the fourth harmonic f4 to the fundamental wave f1 in terms of amplitude, namely, (f2+f3+f4)/f1, this is 1.74 in a Hua mai and 1.5 in a Ping mai. It is therefore possible to discriminate between a Hua mai and a Ping mai on the basis of these values. When attention is given to the ratio of the sum of the fifth harmonic f5, sixth harmonic f6, and seventh harmonic f7 to the fundamental wave f1 in terms of amplitude, namely, (f5+f6+f7)/f1, this is 0.36 in a Hua mai, 0.26 in a Ping mai and 0.42 in a Xuan mai. It is therefore possible to discriminate between a Xuan mai and other pulses on the basis of these values.

1.2 Structure of the Pulse Wave Examination Apparatus

The pulse wave examination apparatus according to this embodiment is structured based on the theoretical basis as described above. In the pulse wave examination apparatus, the pulse wave forms detected from subjects are treated by frequency analysis to extract a tidal wave component and a dicrotic wave component thereby judging the pulse condition on the basis of the results of the extraction. Incidentally, the external structure of the pulse wave examination apparatus will be described later in the section "10. External structures of aforementioned embodiments".

Figure 1:
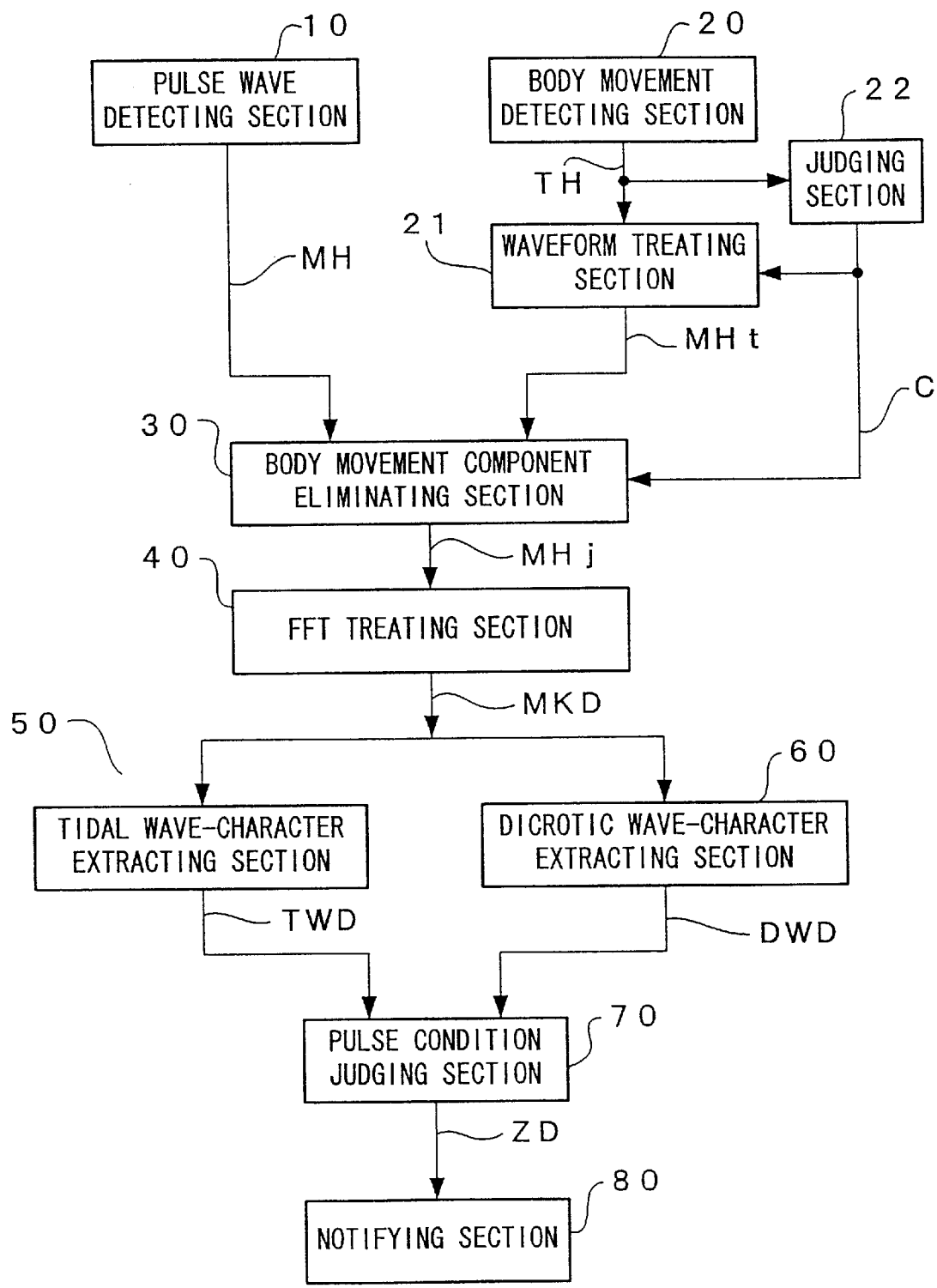
FIG. 1 is a block diagram showing the structure of a pulse wave examination apparatus of a first embodiment.

FIG. 1 is a block diagram showing the functional structure of the pulse wave examination apparatus according to this embodiment. In this figure, a pulse wave detecting section 10 detects the pulse waveform of, for instance, the periphery (e.g., arteria radialis) of a subject, to output the detected signal as MH to a body movement eliminating section 30.

A body movement detecting section 20 comprises, for instance, an acceleration sensor and detects the body movement of a subject to output the detected signal as a signal TH to a waveform treating section 21. The waveform treating section 21 comprises, for instance, a low-pass filter, and performs waveform-shaping treatment of the signal TH output from the body movement detecting section 20 to output a signal MHt showing a body movement component. The body movement eliminating section 30 subtracts the signal MHt showing a body movement component from the signal MH output from the pulse wave detecting section 10 to output a signal MHj showing a pulse wave component.

The pulse wave examination apparatus according to this embodiment is a type treating the pulse waveform detected from a subject. In general, when the subject itself carries some movement, in addition to the signal MHj showing a pulse wave component, the signal MHt showing a body movement component is superimposed on the signal MH detected by the pulse wave detecting section 10. For this, MH=MHt+MHj and hence the signal MH output from the pulse wave detecting section 10 does not show the exact pulse waveform of the subject.

Meanwhile, since the blood flow is affected by, for instance, blood vessels and organizations, the body movement component MHt included in the signal MH is not considered to be just the signal TH showing the body movement of the subject but is considered to be somewhat dulled.

Because of this, the body movement eliminating section 30 uses, as the signal MHt, a signal produced by shaping the waveform of the signal TH in the waveform treating section 21. The signal TH shows the body movement of the subject directly and is output from the body movement detecting section 20. The body movement eliminating section 30 subtracts the signal MHt from the signal MH output from the pulse wave detecting section 10 to eliminate the influence of the body movement, thereby outputting the signal MHj showing the pulse component. The type, number of stages, constant, and the like of the low-pass filter used in the waveform treating section 21 are determined based on the data measured in practice.

In the meantime, when the body movement component eliminating section 30 is made to operate for the elimination of the body movement component even if there is no body movement, the noise of the body movement detecting section 20 causes a deterioration of the S/N ratio of the signal output from the body movement component eliminating section 30, and power is consumed by the body movement eliminating operation. Hence, in this embodiment, a judging section 22 is provided. The judging section 22 determines whether body movement is present or not, based on the body movement waveform TH, to yield a control signal C. Specifically, the judging section 22 makes a judgment by comparing a threshold value with the body movement waveform TH. The threshold value is prescribed in advance, taking a noise level into consideration, so that whether the body movement is present or not can be determined. Then, when the control signal C indicates that no body movement is present, the operations of the waveform treating section 21 and body movement component eliminating section 30 are suspended. In this case, the pulse waveform MH is output directly from the body movement component eliminating section 30. This can improve the SN ratio of the output signal from the body movement component eliminating section 30 and reduce power consumption in the apparatus.

Next, an FFT treating section 40 provides the signal MHj, showing a pulse wave component, with FFT treatment to carry out frequency analysis of the pulse wave component. The result of the frequency analysis can be obtained in the form of a plurality of line spectrums. Then the frequency and the energy level of every line spectrum are calculated. The FFT treating section 40 compares this spectrum data and specifies one having the highest energy level as the fundamental wave f1 of the pulse wave component. The FFT treating section 40 also multiplies the frequency of the fundamental wave f1 integral-fold to specify each harmonic, and outputs pulse wave analysis data MKD showing each energy level of the fundamental wave f1 and of the second harmonic f2 to the tenth harmonic f10.

In succession, a tidal wave-character extracting section 50 yield a tidal wave-character data TWD showing the characteristics of the tidal wave on the basis of the pulse wave analysis data MKD. As outlined above, the characteristics of the tidal wave can be expressed by the ratio of the sum of the fifth harmonic f5, the sixth harmonic f6, and the seventh harmonic f7 to the fundamental wave f1 in the pulse waveform. Hence the tidal wave-character extracting section 50 yields the tidal wave-character data TWD according to the following equation:

$$TWD=(f5+f6+f7)/f1$$

Then, a dicrotic wave-character extracting section 60 yields dicrotic wave-character data DWD showing the characteristics of the dicrotic wave. As outlined above, the characteristics of the dicrotic wave can be expressed by the ratio of the sum of the second harmonic f2, the third harmonic f3, and the fourth harmonic f4 to the fundamental wave f1 in the pulse waveform. Hence the tidal wave-character extracting section 60 yields the dicrotic wave-character data DWD according to the following equation:

$$DWD=(f2+f3+f4)/f1$$

Then, a pulse condition judging section 70 judges the pulse condition on the basis of the tidal wave-character data TWD and the dicrotic wave-character data DWD to yield pulse condition data ZD showing the type of pulse condition of the subject. In more detail, first, the pulse condition judging section 70 compares the tidal wave-character data TWD with a first threshold value to yield pulse condition data ZD1 showing that the pulse condition is a Xuan mai if the tidal wave-character data TWD exceeds the first threshold value. The first threshold value is prescribed in advance so as to determine whether the tidal wave-character data TWD shows a Xuan mai or not. In this instance, the first threshold value is designed to be 0.41.

When the tidal wave-character data TWD is less than the first threshold value, on the contrary, the dicrotic wave-character data DWD is compared with a second threshold value. If the dicrotic wave-character data DWD is less than the second threshold value, pulse condition data ZD2 showing that the pulse condition is a Ping mai is yielded, whereas, if the dicrotic wave-character data DWD exceeds the second threshold value, pulse condition data ZD3 showing that the pulse condition is a Hua mai is yielded. Here, the second threshold value is prescribed in advance so as to determine whether the dicrotic wave-character data DWD shows a Ping mai or a Xuan mai. In this instance, the second threshold value is designed to be 1.62.

A notifying section 80 is a type which outputs pulse condition data ZD by display or voice. For instance, the notifying section 80 displays the characters "Hua mai, Ping mai, Xuan mai" or symbols, e.g., icons. This allows the subject and a third party, e.g., a doctor to recognize the pulse condition.

1.3 Action of the Pulse Wave Examination Apparatus.

Figure 2:
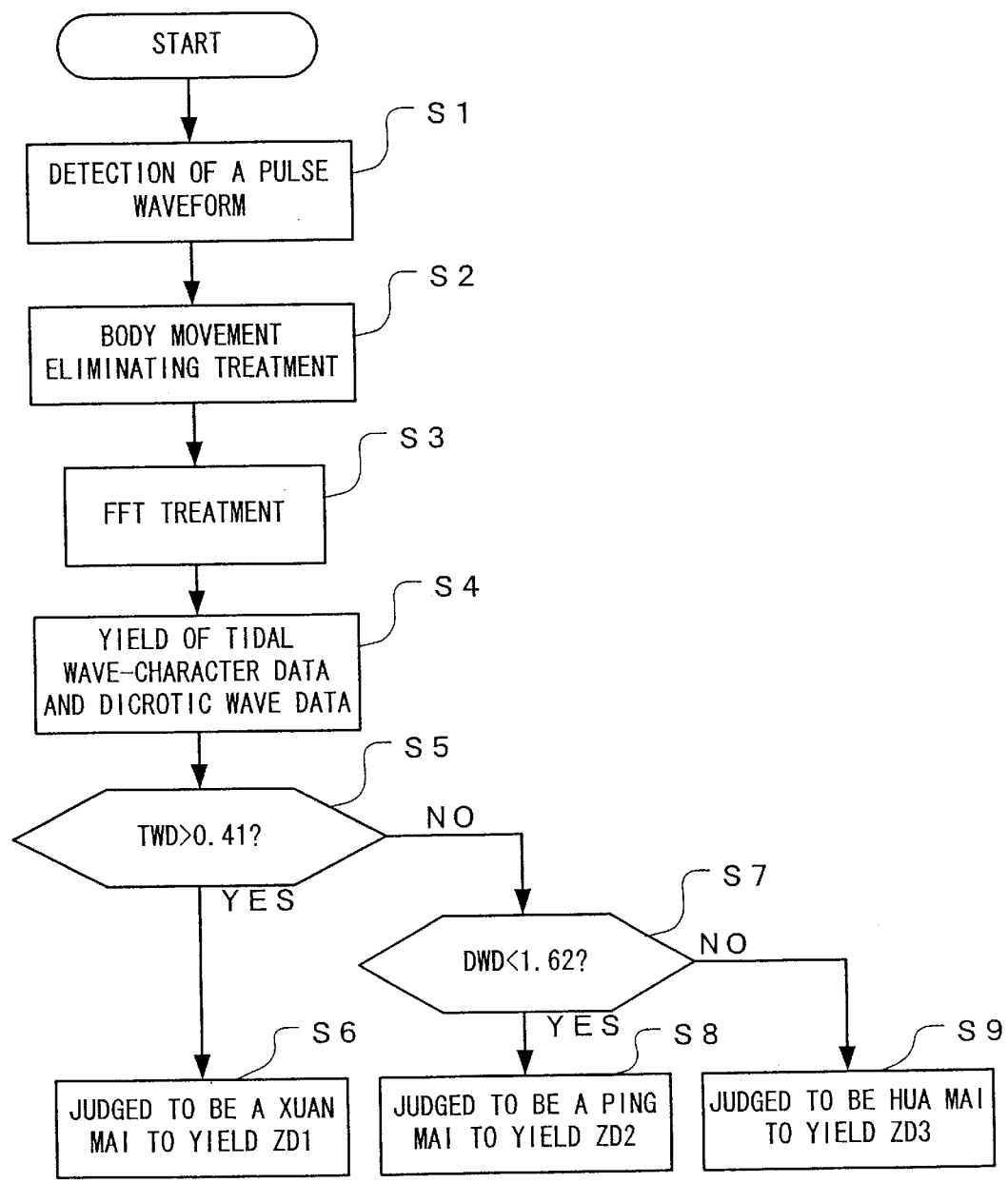
FIG. 2 is a flow chart for describing the action of the pulse wave examination apparatus of the first embodiment.

Next, the action of the pulse wave examination apparatus of the first embodiment will be described with reference to FIG. 2.

First, although a body movement component due to the movement of the subject is superimposed on the signal MH output from the pulse condition detecting section 10, the body movement component is eliminated by the body movement component eliminating section 30 and the signal MHj showing only a pulse wave component is supplied to the FFT treating section 40 (Step S1 and Step S2).

Next, in the FFT treating section 40, the signal MHj is subjected to FFT treatment to yield the fundamental wave f1 of the pulse wave component and each of harmonics f2 to f10 as the pulse wave analysis data MKD, which is then supplied to the tidal wave-character extracting section 50 and the dicrotic-character extracting section 60 (Step S3).

After this step, the tidal wave-character extracting section 50 calculates the ratio of the sum of the fifth harmonic f5, the sixth harmonic f6, and the seventh harmonic f7 to the fundamental wave f1 of the pulse waveform, which ratio expresses the characteristics of the tidal wave, to yield the tidal wave-character data TWD. The dicrotic wave-character extracting section 60 calculates the ratio of the sum of the second harmonic f2, the third harmonic f3, and the fourth harmonic f4 to the fundamental wave f1 of the pulse waveform, which ratio expresses the characteristics of the dicrotic wave, to yield the dicrotic wave-character data DWD (Step S4).

After the characteristics of the tidal wave and dicrotic wave of the pulse waveform are extracted in this manner, the pulse condition judging section 70, first compares the tidal wave-character data TWD with a first threshold value (Step S5). If the tidal wave-character data TWD exceeds the first threshold value (0.41), pulse condition data ZD1 showing that the pulse condition is a Xuan mai is yielded in Step S6.

On the other hand, if the tidal wave-character data TWD is less than the first threshold value (0.41), the result of the judgment in the Step 5 is "No" and a judgment on the pulse condition will be made based on the dicrotic wave-character data DWD in Step S6. In this case, the pulse condition judging section 70 determines whether the dicrotic wave-character data DWD is less than a second threshold value (1.62) or not, and yields pulse condition data ZD2 showing that the pulse condition is a Ping mai if the dicrotic wave-character data DWD is less than the second threshold value in Step S8. On the other hand, if the dicrotic wave-character data DWD exceeds the second threshold value (1.62), the result of the judgment in Step S7 is "NO" and pulse condition data ZD3 showing that the pulse condition is a Hua mai is yielded in Step S9.

In the first embodiment, in this manner, attention is given to the fact that specialists skilled in sphygmopalpation judge the pulse condition on the basis of the tidal wave and dicrotic wave of the pulse waveform, and that the characteristics of the tidal wave and dicrotic wave appear on specific high harmonics and the pulse waveform is subjected to frequency analysis to extract the characteristics of the tidal wave and dicrotic wave. Thus the pulse condition can be judged objectively and accurately.

2. Second Embodiment

Next, a pulse wave examination apparatus according to a second embodiment of the present invention will be described.

In the foregoing first embodiment, attention is paid to the fact that the Hua mai and the Ping mai are characterized by the dicrotic wave, the Xuan mai is characterized by the tidal wave, and the pulse waveform is subjected to FFT treatment. Based on the result of the analysis, frequency components corresponding to the dicrotic wave and to the tidal wave are respectively extracted to make a judgment on the basis of the extraction.

Now, in the frequency analysis by FFT treatment, if there is no data over a somewhat extended period, no analysis result can be obtained. In general FFT treatment, therefore, the treatment is performed on a pulse waveform over several cycles.

However, the dicrotic wave and the tidal wave appear in a partial period in the pulse waveform. Accordingly, if the frequency analysis is carried out only in the periods corresponding to the dicrotic wave and tidal wave, the judgment accuracy for the pulse condition can be further improved.

As a consequence, in the second embodiment, the pulse waveform is treated using wavelet transformation performing frequency analysis and time analysis simultaneously to specify the pulse condition.

2.1 Whole Structure of the Pulse Wave Apparatus

Figure 3:
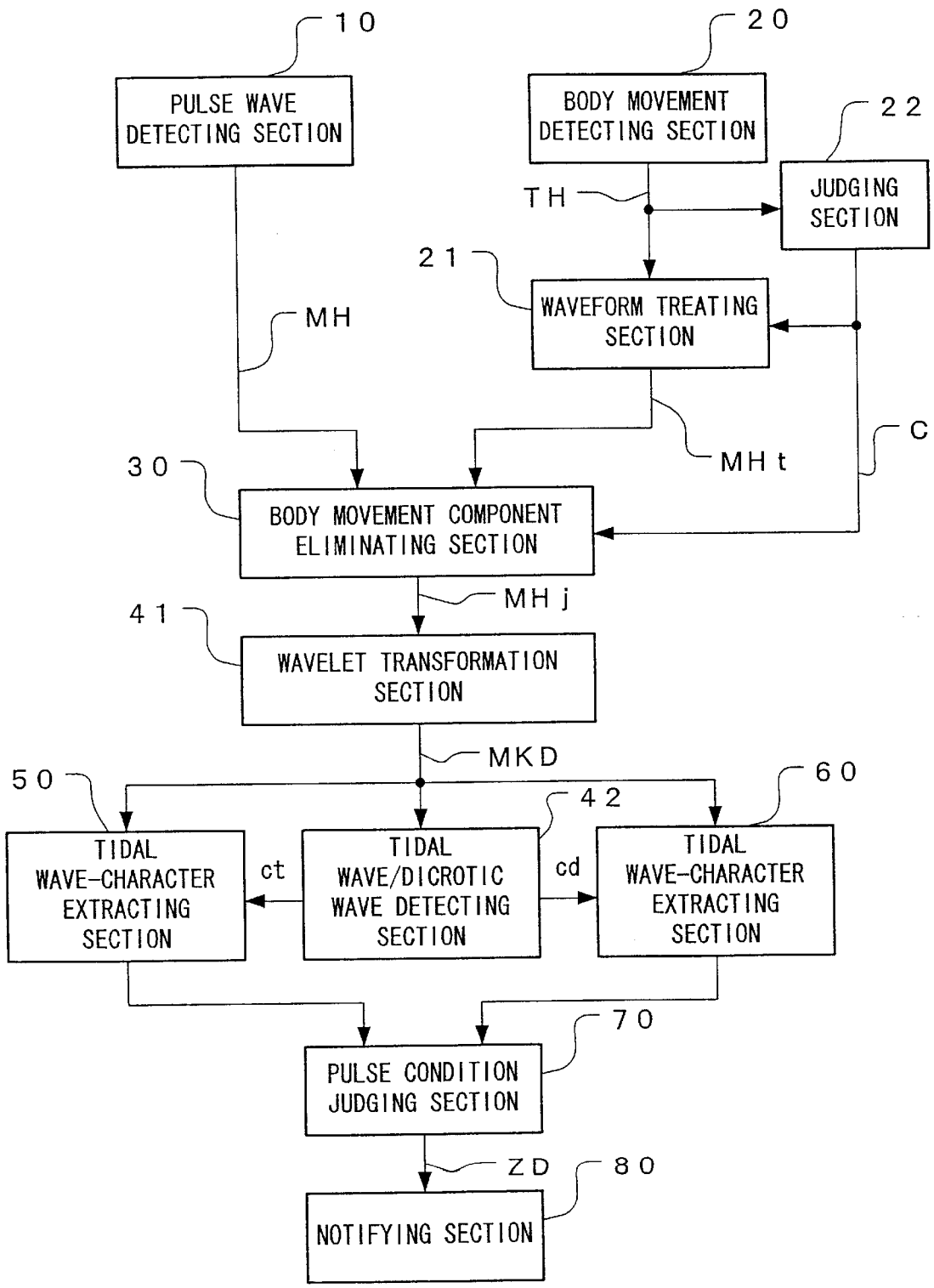
FIG. 3 is a block diagram showing the structure of a pulse wave examination apparatus of a second embodiment.

Next, the structure of the pulse wave examination apparatus according to the second embodiment is shown in FIG. 3. The pulse wave examination apparatus shown in FIG. 3 is the same as the pulse wave examination apparatus shown in FIG. 1 except that a wavelet transformation section 41 is used in place of the FFT treating section 40, a tidal wave/dicrotic wave detecting section 42 which specifies the time positions of the tidal wave and dicrotic wave is installed, and the inner structures of a tidal wave-character extracting section 50, dicrotic wave-character extracting section 60 and pulse condition judging section 70 differ from those used in the first embodiment. The second embodiment will be hereinafter described mainly with respect to the different points between the two embodiments.

2.2 Wavelet Transformation Section

First, the structure of the wavelet transformation section 41 will be described in detail with reference to the drawings.

Generally, in time/frequency analysis which picks up signals in terms of both time and frequency, a wavelet is a unit which cuts out a part of the signal. The wavelet transformation signifies the magnitude of each part of the signal cut out by this unit. As a basic function to define the wavelet transformation, a function ψ(x) localized in terms of time and frequency is introduced as a mother wavelet. Here, the wavelet transformation by the mother wavelet ψ(x) of a function f(x) is defined as follows:

$$(W_\psi f)(b, a) = \int_{-\infty}^{\infty} \frac{1}{\sqrt{a}} \psi\left(\frac{x-b}{a}\right) f(x) dx \qquad (2)$$

where "b" is a parameter used when the mother wavelet ψ(x) is translated and "a" is a parameter when the mother wavelet ψ(x) is scaled (expansion). In the equation (2), the wavelet ψ((x−b)/a) is formed when the mother wavelet ψ(x) is translated by "b" and expanded "a" times. In this case, the width of the mother wavelet ψ(x) is extended in relation to the scale parameter "a". 1/a therefore corresponds to the frequency. The wavelet transformation section 41 is structured so as to calculate the equation (2). The detail of the structure is as shown in FIG. 4.

Figure 4:
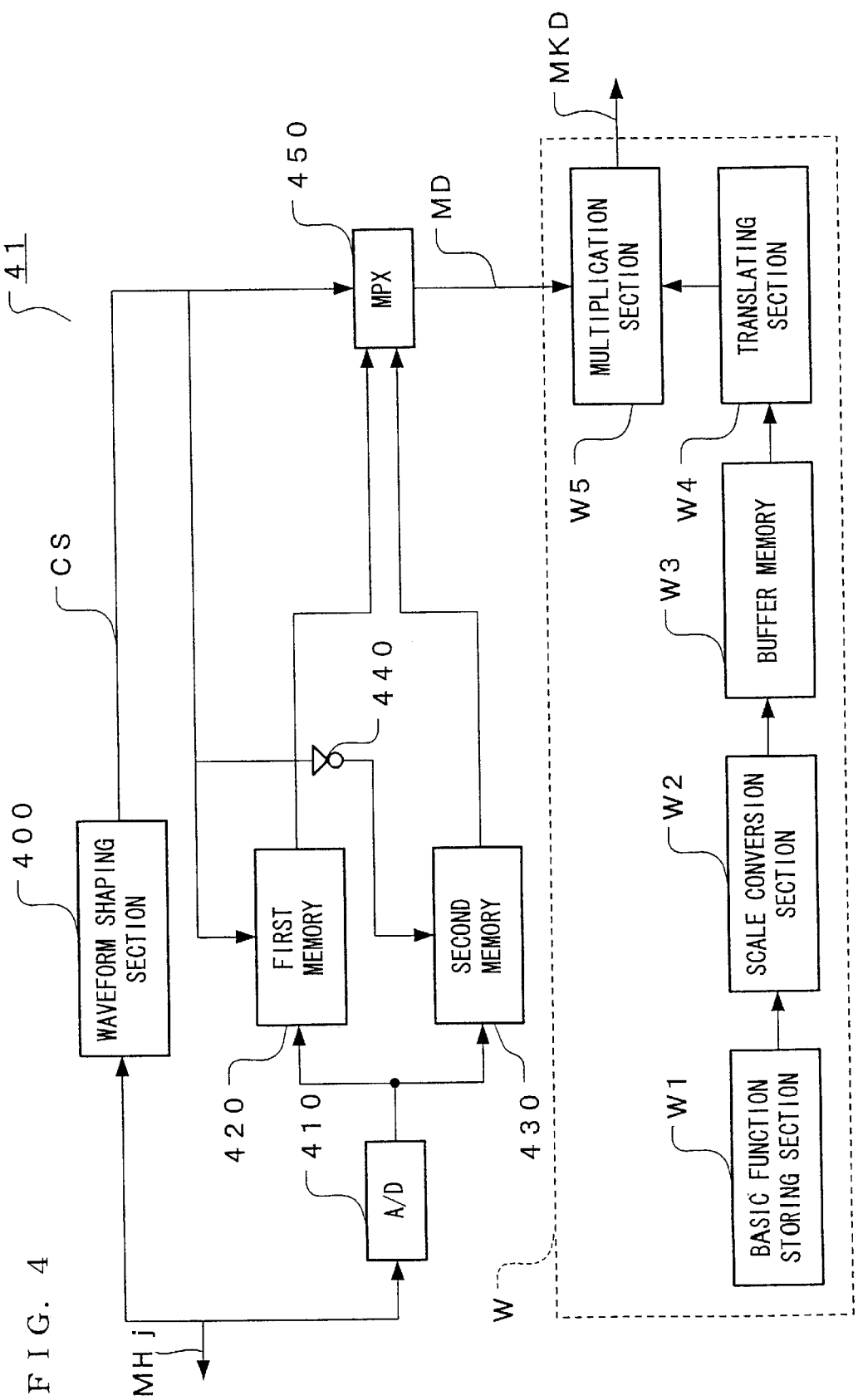
FIG. 4 is a block diagram showing an example of the structure of a wavelet transformation section of the second embodiment.

In FIG. 4, a signal MHj output from a body movement component eliminating section 30 is supplied to a waveform shaping section 400 and an A/D converter 410. The waveform shaping section 400 yields a control signal CS and a clock CK which are synchronized with the pulse waveform MHj.

Figure 5:
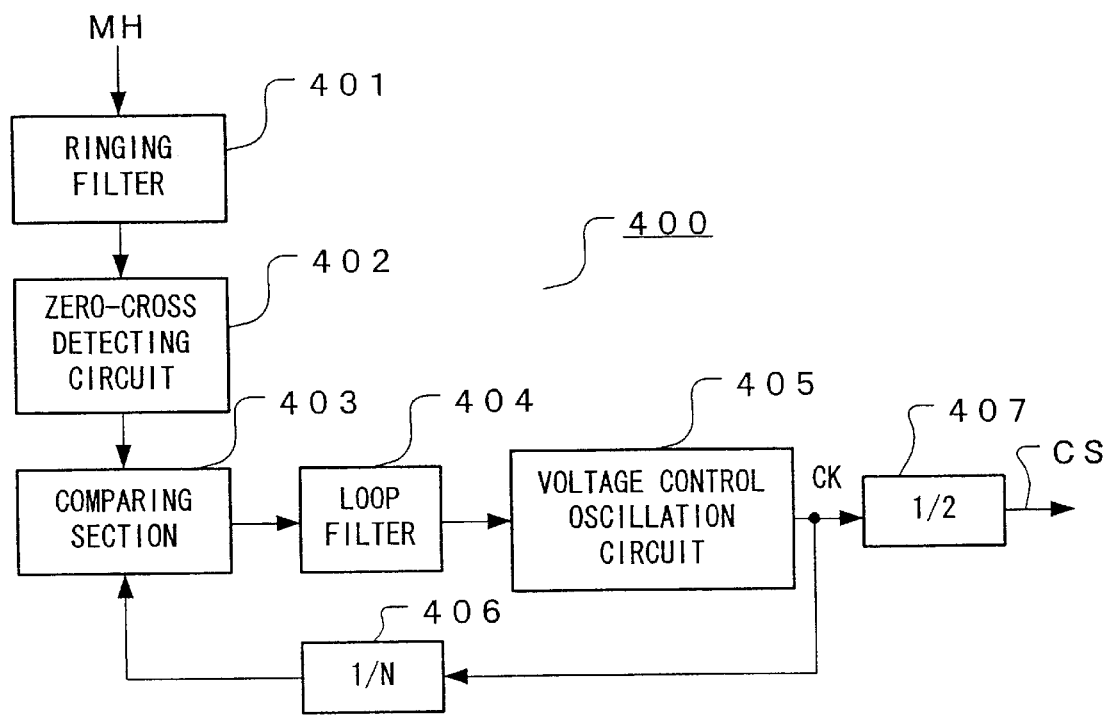
FIG. 5 is a block diagram showing the structure of a waveform shaping section of the second embodiment.
Figure 6:
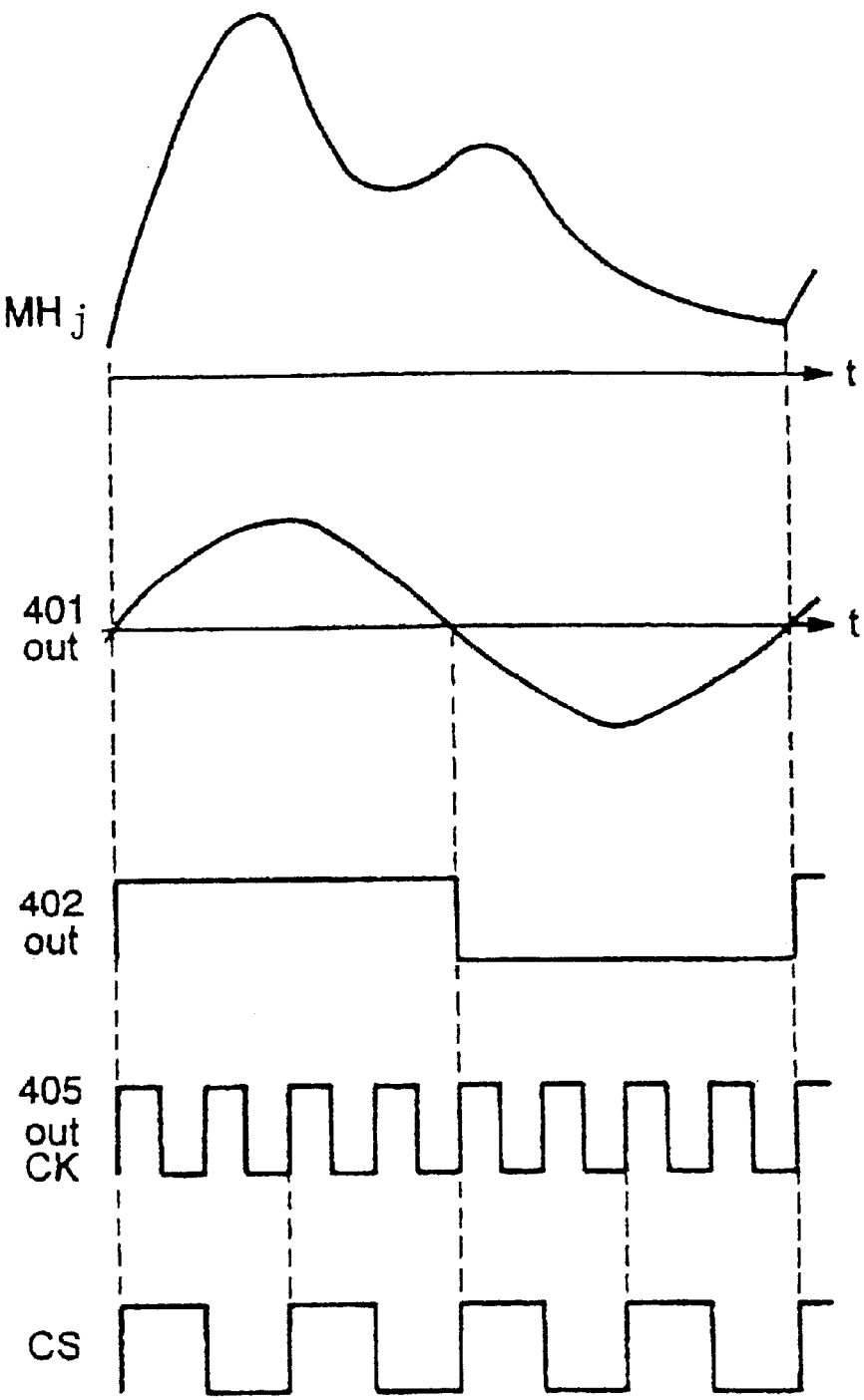
FIG. 6 is a timing chart showing the action of the waveform shaping section of the second embodiment.

Here, a block diagram of the waveform shaping section 400 is shown in FIG. 5. In FIG. 5, a ringing filter 401 is a filter with a high Q value with the center frequency being 2.2 Hz and the passing band being 0.8 Hz to 3.5 Hz. Since the fundamental wave component of the pulse waveform is generally in a range between 0.8 Hz and 3.5 Hz, the fundamental wave component is extracted when the pulse waveform MHj passes through the ringing filter 401. For instance, as shown in FIG. 6, when the pulse waveform MHj is input to the ringing filter 401, its output is that shown as 401 out in FIG. 6.

Next, a zero-cross detecting circuit 402 comprises a comparator and the like and compares an output signal from the ringing filter 401 with the ground level to yield a rectangular wave. The rectangular wave is synchronized with the pulsation. For instance, if the signal from the ringing filter 401 is that shown as "401 out" in FIG. 6, an output signal from a zero-cross detecting circuit 402 is that shown as "402 out" in the same figure.

Next, a comparing section 403, a loop filter 404, a voltage control oscillation circuit 405, and a frequency divider 406 comprise a phase lock loop. When an output signal from the zero-cross detecting circuit 402 and an output signal from the frequency divider 406 are supplied to one input port and another input port of the comparing section 403 respectively, the comparing section 403 outputs an error signal corresponding to a phase difference between the two output signals. When the error signal is supplied to the voltage control oscillation circuit 405 via the loop filter 404, the voltage control oscillation circuit 405 outputs a clock signal CK. The clock signal CK is divided in 1/N by the frequency divider 406 and is fed back to the other input port of the comparing section 403. For instance, if the dividing ratio is 1/8, the frequency of the clock signal CK becomes 8 times the frequency of the output signal from the zero-cross detecting circuit 402 as shown by "405 out CK" in FIG. 6. The clock signal CK is then divided in half in a frequency divider 407 and output as a control signal CS as shown in FIG. 6.

The pulse waveform MHj is also converted into a digital signal by an A/D converter 410 shown in FIG. 4 and the digital signal is then stored in a first memory 420 and a second memory 430. Here, the control signal CS is supplied directly to a write-enable terminal of the first memory 420. The control signal CS is reversed by an inverter 440 and the reversed signal is supplied to a write-enable terminal of the second memory 430. Hence, the fist and second memories 420, 430 store the pulse waveform MH alternately at intervals of the period.

The symbol 450 represents a multiplexer which selects the pulse wave data MD read out alternately from the first and second memories 420, 430 to output the selected data to a basic function developing section W. In this manner, the pulse wave data MD is read out from the second memory 430 during the writing time of the first memory 420 and the pulse wave data MD is written in the second memory 430 during the reading time of the first memory 420.

Next, the basic function developing section W has a structure enabling the calculation of the foregoing equation (2). The aforementioned clock signal CK is supplied to the basic function developing section W and a calculation process is carried out at intervals of the period. The basic function developing section W comprises a basic function storing section W1 for storing the mother wavelet ψ(x), a scale conversion section W2 for converting the scale parameter a, a buffer memory W3, a translating section W4 for carrying out parallel translation, and a multiplication section W5. It is noted that, as the mother wavelet ψ(x) stored in the basic function storing section W1, a Gabor wavelet, Mexican hut, Haar wavelet, Meyer wavelet, Shannon wavelet or the like may be applied and, in this embodiment, a mother wavelet called symlets 5 is used to advantageously extract the characteristics of the pulse waveform.

First, when the mother wavelet ψ(x) is read out from the basic function storing section W1, the scale conversion section W2 carries out the conversion of the scale parameter "a". Here, the scale parameter "a" corresponds to the period. Hence when "a" is increased, the mother wavelet ψ(x) is expanded on the time axis. In this case, because the data volume of the mother wavelet ψ(x) which is stored in the basic function storing section W1 is fixed, the data volume is reduced if "a" is increased. The scale conversion section W2 performs compensation treatment to compensate the reduction in data and carries out curtailed treatment when "a" is small to yield a function ψ(x/a). This data is stored in the buffer memory W3 once.

Next, the translating section W4 reads out the function ψ(x/a) from the buffer memory W3 with timing corresponding to the translate parameter b to translate the function ψ(x/a) thereby yielding a function ψ((x−b)/a).

Then, a multiplication section W5 multiplies a variable $1/a^{1/2}$, by the function ψ(x−b/a) and by the pulse wave data MD to undergo wavelet transformation at each beat to yield the pulse wave analysis data MKD. In this embodiment, the pulse wave analysis data MKD is divided into frequency zones, for example, 0 Hz–0.5 Hz, 0.5 Hz–1.0 Hz, 1.0 Hz–1.5 Hz, 1.5 Hz–2.0 Hz, 2.0 Hz–2.5 Hz, 2.5 Hz–3.0 Hz, 3.0 Hz–3.5 Hz, and 3.5 Hz–4.0 Hz and output.

2.3 Tidal Wave/dicrotic Wave Detecting Section

Next, a tidal wave/dicrotic wave detecting section 42 compares the pulse wave analysis data MKD in a certain frequency zone with a threshold value to yield control signals ct and cd which specify the time positions of the tidal wave and dicrotic wave respectively.

Figure 7:
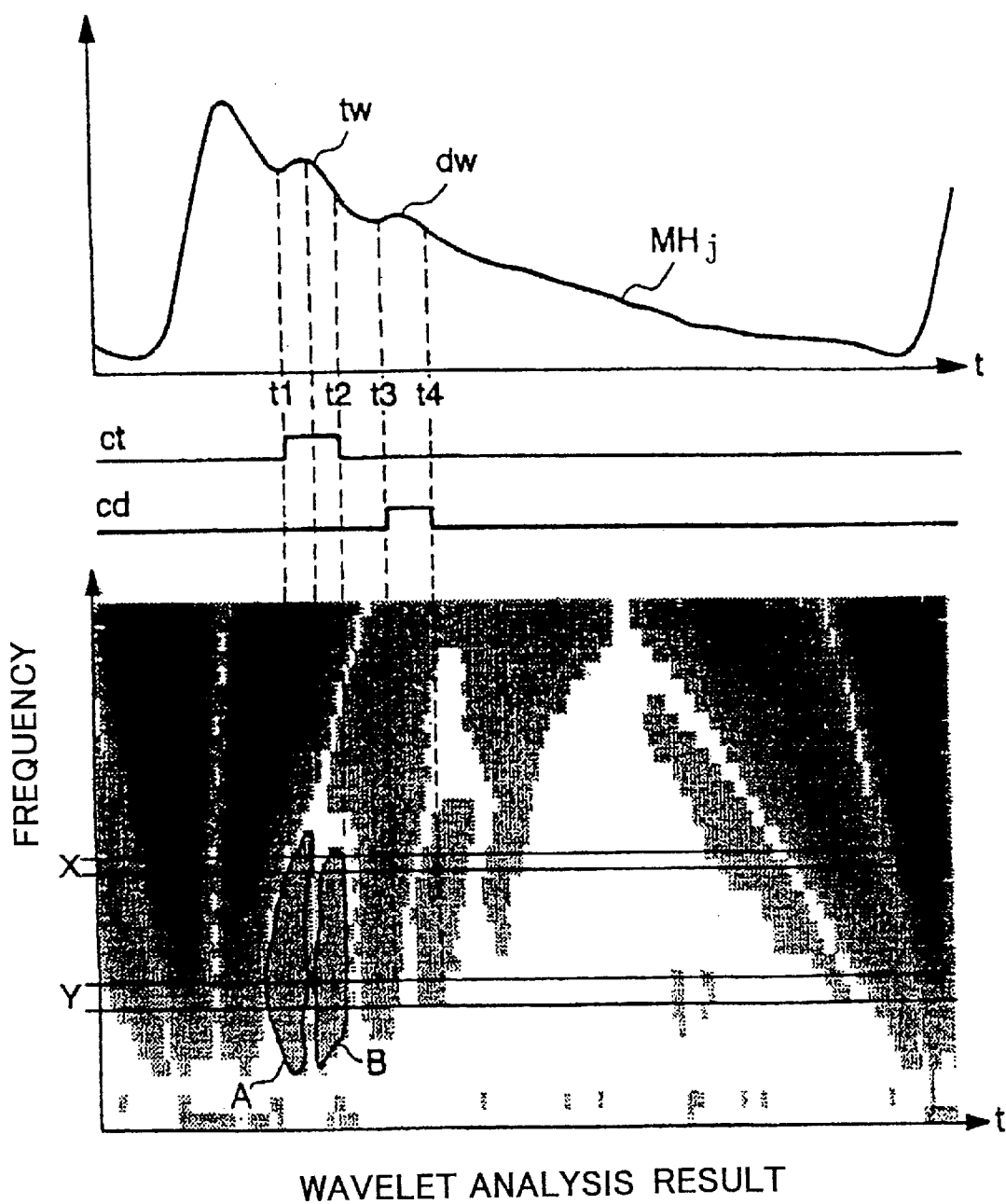
FIG. 7 is a view for describing the action of a tidal wave/dicrotic wave detecting section of the second embodiment.

For instance, in the pulse waveform MHj shown in FIG. 7, the tidal wave and the dicrotic wave are shown by tw and dw respectively. When the wavelet transformation of this pulse waveform MHj is carried out, the result of wavelet analysis as shown in the same figure is obtained. In the result of the analysis, the values of the pulse wave analysis data MKD is expressed by shading. The darker the color of the parts, the larger the values of the pulse wave analysis data MKD, whereas the lighter the color of the parts, the smaller the values of the pulse wave analysis data MKD.

It is seen from the figure that the zones A and B surrounded by the parts (white) with a small value for the pulse wave analysis data MKD are located in a time-domain corresponding to the tidal wave. The part having a small value in terms of the pulse wave analysis data in the direction of the Y or frequency axis shows that the energy of the pulse waveform MHj in its period is at a low level. In this part, the pulse waveform MHj is flat. For instance, the boundary between the zones A and B corresponds to a peak of the tidal wave tw.

If attention is paid to a certain frequency zone, the time position of the tidal wave tw can be detected based on its change. In this embodiment, a comparison of the value of the pulse wave analysis data MKD in a frequency zone X with a threshold value yields a control signal ct specifying the time positions between t1 and t2 of the tidal wave tw as shown in FIG. 7. On the other hand, a comparison of the value of the pulse wave analysis data MKD in a frequency zone Y with a threshold value yields a control signal dw specifying the time positions between t3 and t4 of the tidal wave tw as shown in FIG. 7.

2.4 Tidal Wave-character Extracting Section and Dicrotic Wave-character Extracting Section First, the tidal wave-character extracting section 50 specifies the time position of the tidal wave on the basis of the control signal ct and adds data in a specific frequency zone among the pulse wave analysis data MKD in the specified period.

The wavelet transformation section 41 is, for instance, designed to be formed of a filter bank in which the characteristics of a high frequency filter 1A and low frequency filter 1B are varied by the clock signal CK synchronized with the pulse waveform MHj as will be mentioned later in the section "14 Other embodiments" (6) with reference to FIG. 58. In this case, if the pulse wave analysis data corresponding to the fundamental wave f1 of the pulse waveform MHj is M*1, the parts showing the characteristics of the tidal wave appear on the fifth harmonic f5 to the seventh harmonic f7 and hence the wavelet transformation section 41 adds M*5, M*6 and M*7 to calculate the tidal wave-character extracting data TWD.

Next, the dicrotic wave-character extracting section 60 specifies the time position of the dicrotic wave on the basis of the control signal cd and adds data in a specific frequency zone among the pulse wave analysis data MKD in this period.

If the wavelet transformation section 41 is formed in such a structure, for instance, as in the description of the tidal wave-character extracting section 50, and the pulse wave analysis data corresponding to the fundamental wave f1 of the pulse waveform MHj is M*1, the parts showing the characteristics of the dicrotic wave appear on the second harmonic f2 to the fourth harmonic f4 and hence the wavelet transformation section 41 adds M*2, M*3 and M*4 to calculate the dicrotic wave-character extracting data DWD.

In this manner, the tidal wave-character extracting section 50 and the dicrotic wave-character extracting section 60 extract the characteristics of the tidal wave and dicrotic wave from the aspect of the time-domain as well as the frequency zone by making clever use of the character of the wavelet transformation which can divide the waveform into a frequency zone and a time-domain to carry out waveform analysis. The characteristics can be thereby extracted with high accuracy.

2.5 Pulse Condition Judging Section and Notifying Section

Next, a pulse condition judging section 70 compares the tidal wave-character extracting data TWD and the dicrotic wave-character extracting data DWD with each threshold value to judge the pulse condition, such as a Ping mai, Hua mai, or Xuan mai, to yield a pulse condition data ZD. A notifying section 80 notifies the subject or a third party, e.g., a doctor, of the pulse condition data ZD by a display, voice or the like in the same way as in the first embodiment.

According to the pulse wave examination apparatus of the second embodiment, as outlined above, the frequency component can be analyzed in a limited period in which the tidal wave and the dicrotic wave appear by undergoing wavelet transformation of the pulse waveform detected from the subject. As a result, the characteristics of the tidal wave and dicrotic wave can be extracted with accuracy to thereby make an exact judgment of the pulse condition.

3. Third embodiment 3.1 Principle of the Third Embodiment

The pulse waveform expresses pulsation when the flow of blood pumped out to an aorta by the contraction of the heart is propagated through an artery and hence has a certain period synchronized with the beat of the heart. Analyzing technics for analyzing a periodic waveform to extract its characteristics include a spectrum analysis represented by FFT (Fast Fourier Transformation). The inventors of the present invention, however, remarked an autocorrelation function which can be dealt with by a simple calculation.

If an irregular variation is represented by x(t) and x(t) has a periodic variation on a period T, x(t) is given by the following equation:

$$x(t)=x(t\pm nT)$$

where n=0, 1, 2, . . . .

A waveform represented by the above equation overlaps the original waveform when it is shifted by an integral multiple of the period. If the irregular variation x(t) is strongly periodical, the wave form becomes similar to the original waveform when it is shifted on the time axis by integral multiple of the period. The similarity of a waveform, shifted by a certain time τ, to the original waveform is investigated and the correlation between x(t) and x(t+τ) is desirably calculated to discriminate a periodic component in the variations. When the irregular variation as a function of time is expressed by x(t), the autocorrelation function is defined as the average value of the product of two variations which are separated from each other by an interval of τ (time) and is given by the following equation:

$$C(\tau)=E[x(t)x(t+\tau)]$$

where E is an ensemble average but may be replaced by the time average in a stationary stochastic process. Thus, the autocorrelation function C(τr) can be expressed as:

$$C(\tau) = \lim_{T \to \infty} \frac{1}{T} \int_{-T/2}^{T/2} x(t)x(t+\tau)dt \quad (3)$$

Also, a value normalized by dividing the autocorrelation function C(τ) by its value calculated when τ=0 is called an autocorrelation function coefficient R(τ) which is given by the following equation:

$$R(\tau)=C(\tau)/C(0)=E[x(t)x(t+\tau)]/E[x^2(t)]$$

Figure 16:
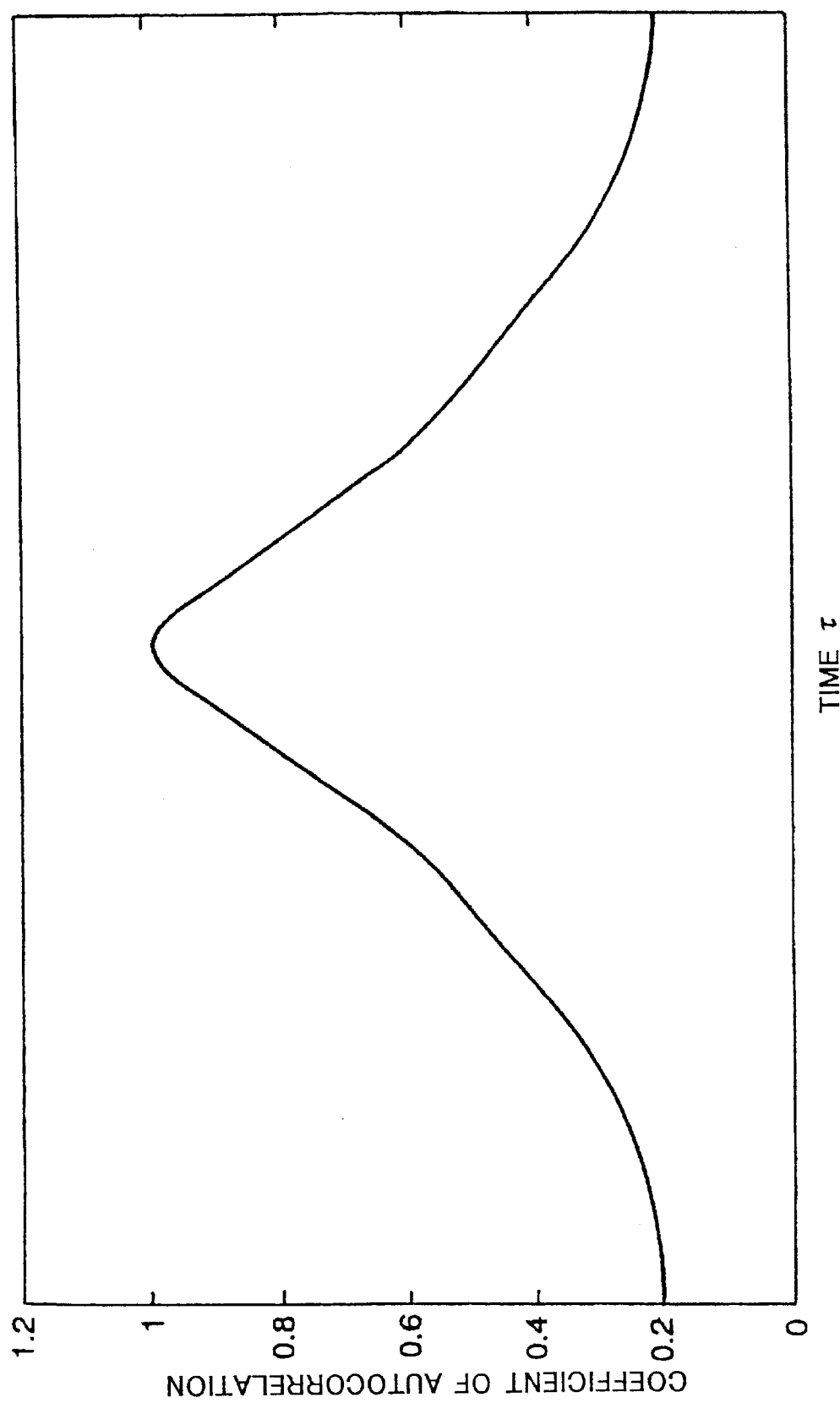
FIG. 16 is a view showing a coefficient of autocorrelation of a Xuan mai.
Figure 17:
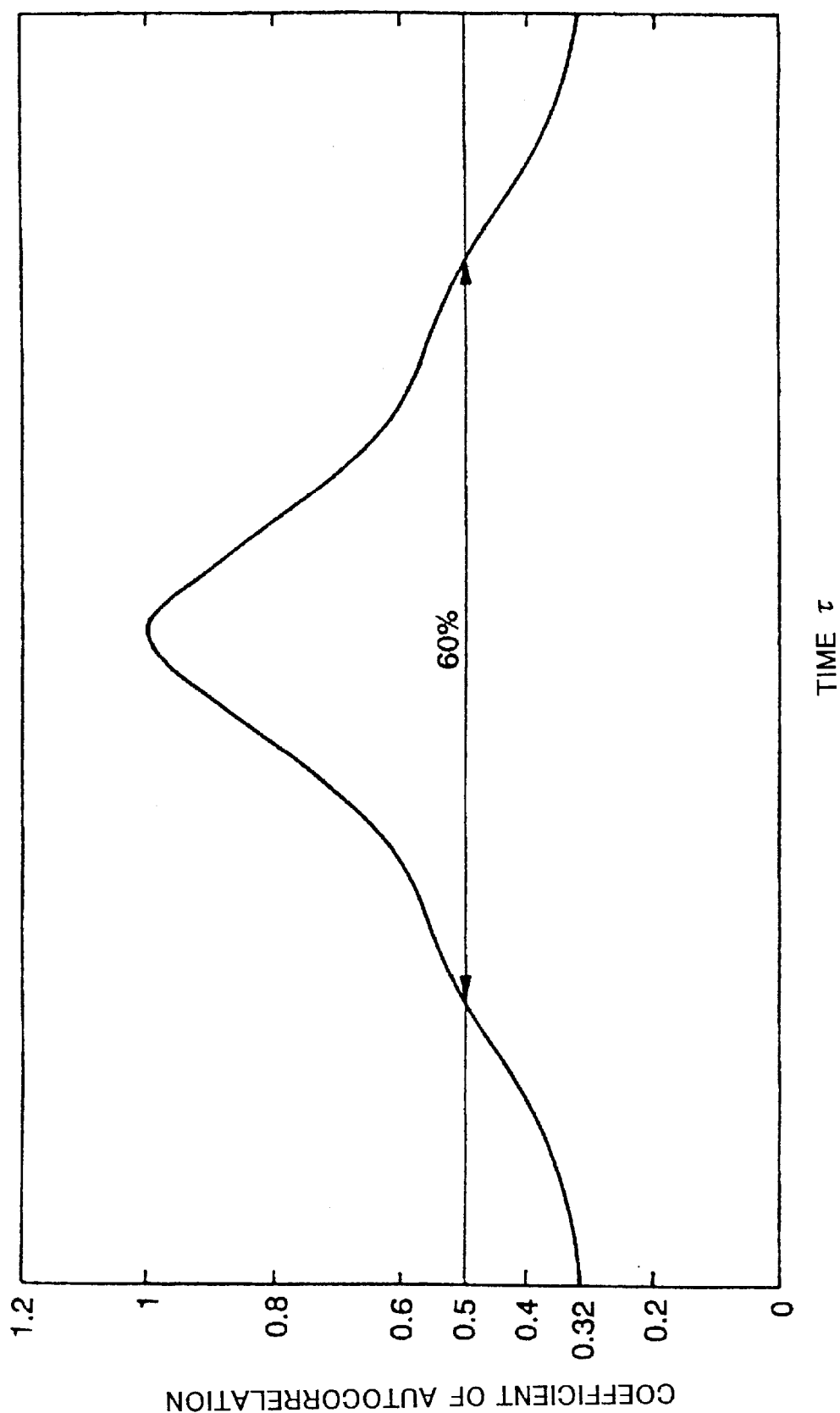
FIG. 17 is a view showing a coefficient of autocorrelation of a Ping mai.
Figure 18:
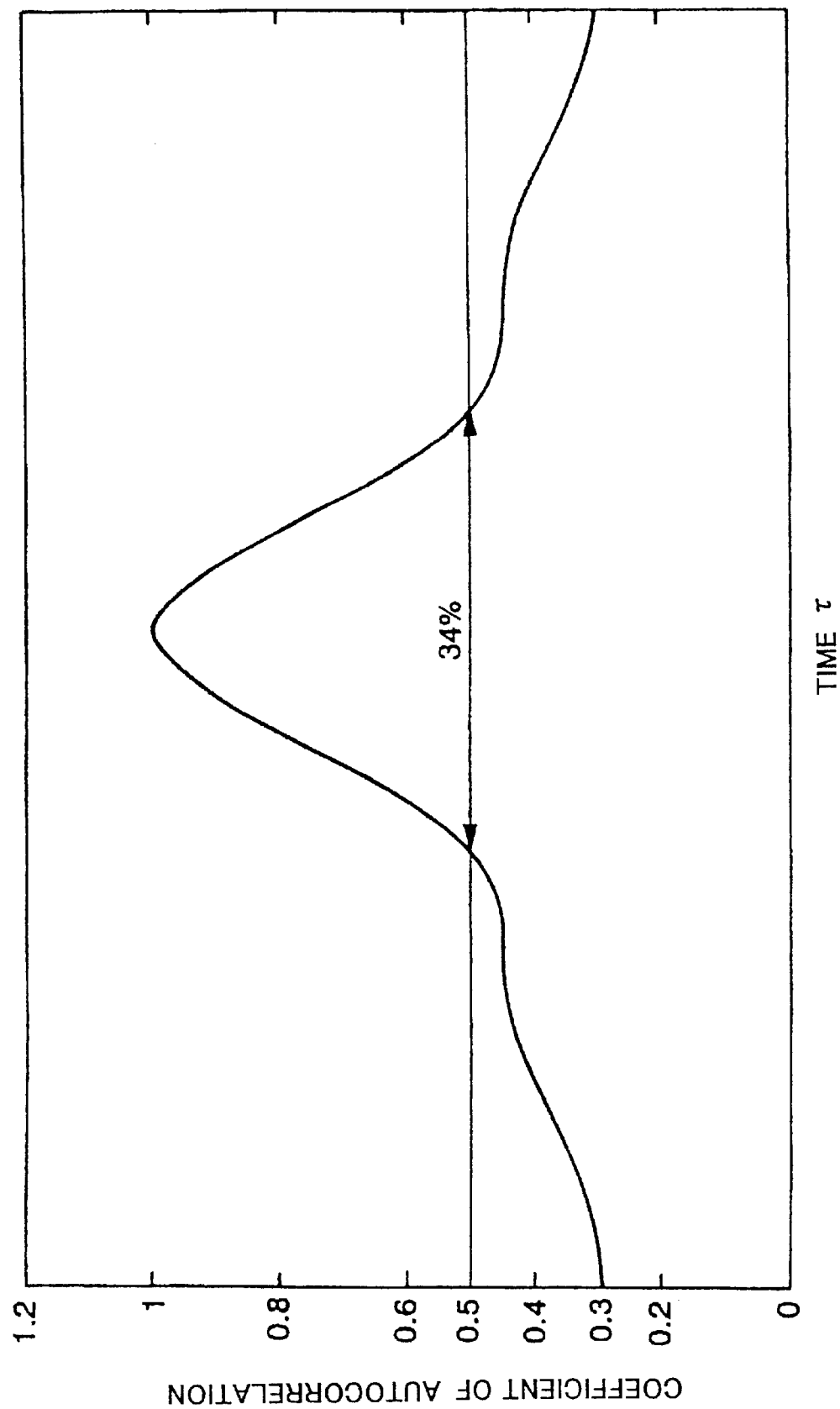
FIG. 18 is a view showing a coefficient of autocorrelation of a Hua mai.

FIGS. 16 to 18 show the autocorrelation function coefficients of a Xuan mai shown in FIG. 45C, a Ping mai shown in FIG. 45A, and a Hua mai shown in FIG. 45B respectively. Comparing these figures, a waviness becomes visible in the waveform of the autocorrelation coefficient R(τ) as the pulse condition changes from a Xuan mai to a Hua mai via a Ping mai. This corresponds to the fact that a Xuan mai has a smooth waveform, a Ping mai includes three peaks but these peaks are small in size and a Hua mai include two large peaks. Stated in another way, the characteristics of each waveform are reflected in the autocorrelation coefficient R(τ). Moreover, the waveform of the autocorrelation coefficient R(τ) is obtained based on a pulse waveform formed over a relatively long period and hence the characteristics of the pulse waveform can be extracted with accuracy.

The instantaneous magnitude of the autocorrelation coefficient $R(\tau)$ is, unlike the instantaneous magnitude of the pulse waveform, given as the time average. Therefore even if the SN ratio of the pulse waveform detected from a living body is somewhat impaired, noises are averaged with the result that the SN ratio is improved. Furthermore, the autocorrelation coefficient $R(\tau)$ is formed by normalizing the autocorrelation function $C(\tau)$ and is hence convenient for analysis by comparing pulse waveforms having different amplitudes.

From the aforementioned reason, the inventors of the present invention determined a criteria specifying the pulse condition by making clever use of the character of the autocorrelation coefficient $R(\tau)$ and have found a pulse wave examination apparatus which judges the pulse condition of the living body according to the criteria.

3.2 Electrical Structure of the Pulse Wave Examination Apparatus

Figure 19:
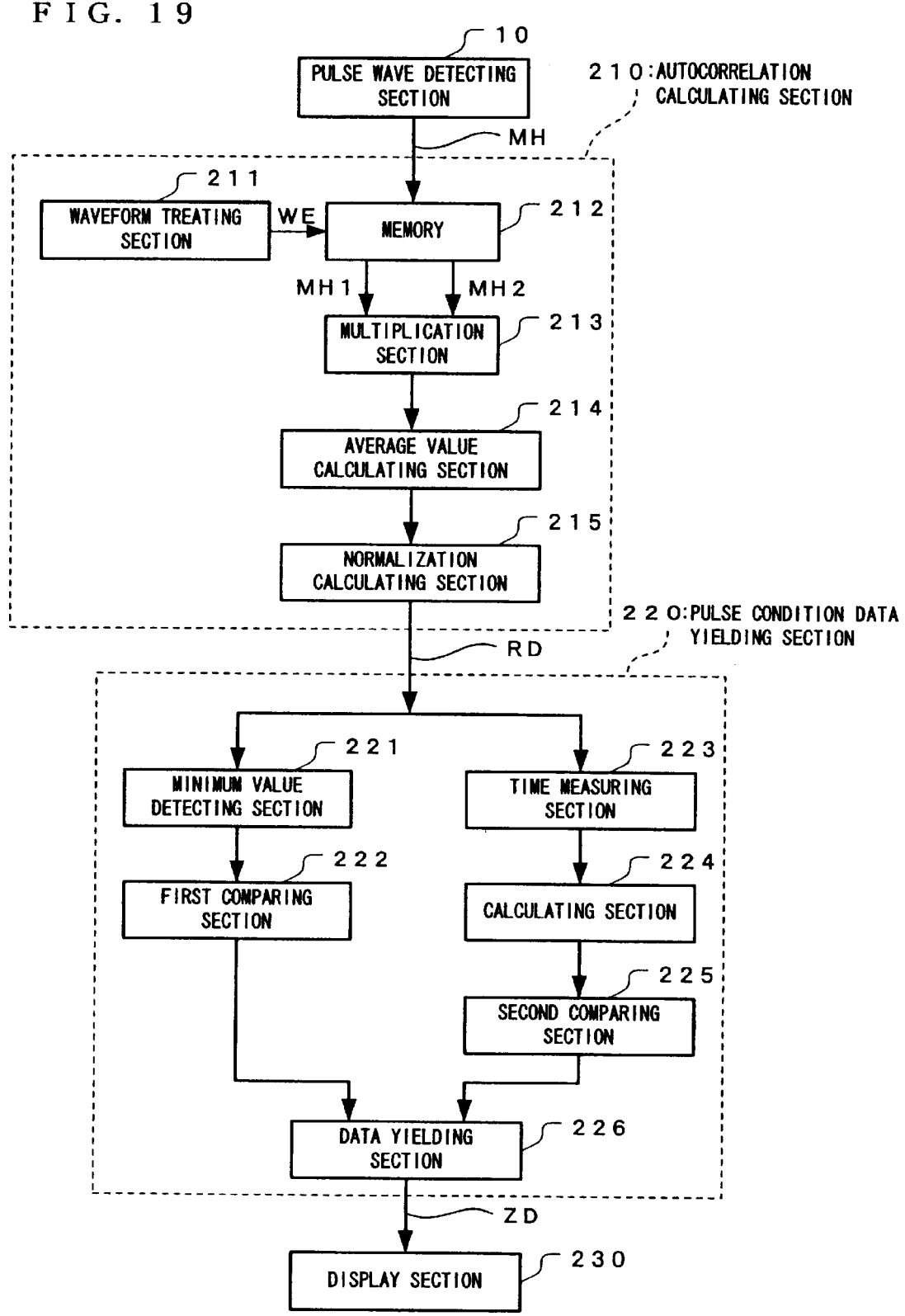
FIG. 19 is a block diagram showing the electrical structure of a pulse wave examination apparatus of a third embodiment.

Next, the electrical structure of the pulse wave examination apparatus will be described with reference to FIG. 19. FIG. 19 is a block diagram showing the electrical structure of the pulse wave examination apparatus.

The pulse wave examination apparatus 1 comprises the pulse wave detecting section 10 for detecting the pulse waveform MH, an autocorrelation calculating section 210 for calculating autocorrelation data RD on the basis of the pulse waveform MH, a pulse condition data yielding section 220 for yielding the pulse condition data ZD on the basis of the autocorrelation RD and a display section 230.

First, the autocorrelation calculating section 210 comprises a waveform treating section 211, a memory 212, a multiplication section 213, an average value calculating section 214 and a normalization calculating section 215. The memory 212 stores the pulse waveform MH in a period of at least one beat. Meanwhile, when it is intended to calculate the autocorrelation function $C(\tau)$ according to the equation (3), it is necessary to integrate $x(t)x(t+\tau)$ from $-T/2$ to $T/2$ (T is infinite). But, considering the fact that $x(t)$ in this embodiment is the pulse waveform MH synchronized with the beat period, the calculation may be made based on the pulse waveform MH in a period of at least one beat. In this embodiment, therefore, the waveform shaping of the pulse waveform MH is carried out by the waveform treating section 211, the shaped waveform is converted into a rectangular wave synchronized with the pulse wave period, and a write control signal WE for controlling the write action of the memory 212 is yielded based on the rectangular wave. For instance, the pulse waveform MH in four periods is written in the memory 212 by the write control signal WE.

Next, the multiplication section 213 read out a pulse waveform MH1 corresponding to $x(t)$ and a pulse waveform MH2 corresponding to $x(t+\tau)$, multiplies the two and outputs the result of the multiplication. The average value calculating section 214 calculates the ensemble average of MH1·MH2 corresponding to the ensemble average of $x(t)x(t+\tau)$ and outputs the result of the calculation.

Next, the normalization calculating section 215 normalizes the result, calculated by the average value calculating section 214, by the autocorrelation function $C(0)$ to yield the autocorrelation data RD. More specifically, the normalization is made by the ensemble average of $X^2(t)$, namely, $MH1^2$. As a result, the autocorrelation data RD shows the autocorrelation coefficient $R(\tau)$ of the pulse waveform MH.

Here, the autocorrelation coefficient RD is examined for the pulse waveform MH of each pulse condition shown in FIGS. 45A to 45C. First, as shown in FIG. 16, the minimum value of the autocorrelation coefficient $R(\tau)$ is 0.2 in a Xuan mai. On the other hand, as shown in FIGS. 17 and 18, the minimum values of the autocorrelation coefficient $R(\tau)$ are 0.32 and 0.3 in a Ping mai and in a Hua mai respectively. The pulse condition is therefore judged to be a Xuan mai when the minimum value of the autocorrelation coefficient is less than 0.25.

Next, the ratio of a period, in which the autocorrelation $R(\tau)$ is greater than 0.5, to a period of one beat is 60% or more in a Ping mai (see FIG. 17) and 34% in a Hua mai (see FIG. 18). Therefore, the pulse condition may be judged to be a Ping mai when this ratio exceeds 47% and to be a Hua mai when the ratio is less than 47%.

The pulse condition data yielding section 220 judges the pulse condition on the basis of the above judging criteria. The pulse condition data yielding section 220 comprises a minimum value detecting section 221 and a first comparing section 222 for detecting a pulse condition of a Xuan mai, a time measuring section 223, a calculating section 224 and a second comparing section 225 for detecting a pulse condition of a Ping mai or Hua mai and a data yielding section 226 for yielding the pulse condition data ZD.

First, the minimum value detecting section 221 detects the minimum value of the autocorrelation data RD in a period corresponding to a period of one beat. The first comparing section 222 determines whether the detected minimum value is less than 0.25 or not and outputs the result of the judgment to the data yielding section 226.

Then, the time measuring section 223 compares the autocorrelation data RD with a prescribed threshold value (0.5) and measures a time interval in which the autocorrelation data RD exceeds the threshold value (0.5). The calculating section 224 calculates the ratio of the measured time interval to a period of one beat. Incidentally, the period of one beat is designed to be supplied from the aforementioned waveform treating section 211. The second comparing section 225 determines whether the calculated result exceeds a prescribed threshold value (47%).

Next, the data yielding section 226 yields the pulse condition data ZD on the basis of each result determined in the first and second comparing sections 222 and 225. First, when the minimum value is judged to be less than 0.25 in the first comparing section 222, the pulse condition data ZD1 showing a Xuan mai is yielded. When the period in which the autocorrelation data RD exceeds 0.5 is judged to exceed 47% in the second comparing section 225, the pulse condition data ZD2 showing a Ping mai results whereas when its period is judged to be less than 47%, the pulse condition data ZD3 showing a Hua mai is obtained.

Next, the display section 230 comprises a ROM, a control circuit, a liquid crystal display device and the like. When the pulse condition data ZD is supplied to the display section 230, the control circuit detects this, reads out characters stored in the ROM and displays these characters on the liquid crystal display. As the characters, specific symbols or icon as well as the characters "Ping mai", "Xuan mai" and "Hua mai" may be used. The display section 230 makes it possible to notify the user or a doctor of the physical condition.

The function of the pulse wave examination apparatus 1 can be described in this manner. In the apparatus used in practice, the autocorrelation calculating section 210 and the pulse condition data yielding section 220 are constituted of CPUs, memories and the like. In this case, the CPU undergoes various calculating processes and comparing processes on the basis of control programs stored in part of the memories to yield the pulse condition data ZD.

3.3 Action of the Pulse Wave Examination Apparatus

Figure 20:
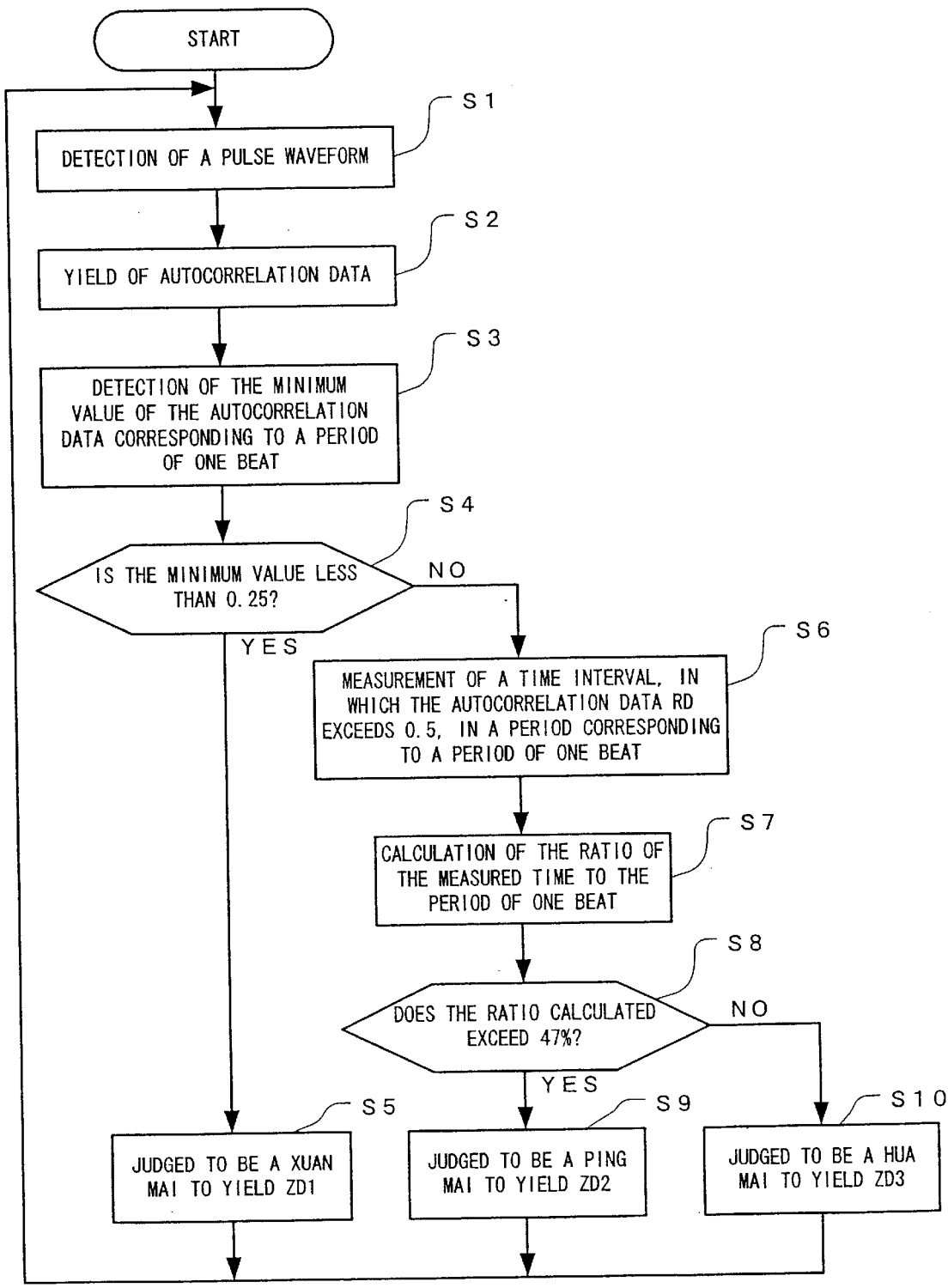
FIG. 20 is a flow chart showing the action of the pulse wave apparatus of the third embodiment.

Next, the action of the pulse wave examination apparatus according to the third embodiment of the present invention will be described with reference to the drawings. FIG. 20 is a flow chart showing the action of the pulse wave examination apparatus.

First, the pulse wave detecting section 10 detects the pulse waveform MH (Step S1).

When the pulse waveform MH is supplied to the autocorrelation calculating section 210, the pulse waveform MH is written in the memory 212 and read out in a fixed period later. An autocorrelation function is calculated based on the read pulse waveform MH and the calculated result is normalized to yield the autocorrelation data RD showing the autocorrelation coefficient R($\tau$) (Step S2).

After that, the pulse condition yielding section 220 yields the pulse condition data ZD on the basis of the autocorrelation data RD in the manner described below. First, when the minimum value of the autocorrelation data RD corresponding to a period of one heartbeat is detected in the minimum value detecting section 221 (Step S3), the first comparing section 222 determines whether the minimum value is less than 0.25 or not (Step S4). When the minimum value is less than 0.25, the result of the determination is expressed as YES and the stage is forwarded to the next step (Step S5) in which the pulse condition is judged to be a Xuan mai to yield the pulse condition data ZD1 in the data yielding section 226.

When the minimum value is 0.25 or more on the contrary, the result of the determination is expressed as NO and a judgment on whether the pulse condition is a Ping mai or a Hua mai is made. In this case, the time measuring section 223 measures a time interval in which the autocorrelation data RD exceeds 0.5, in a period corresponding to a period of one heartbeat (Step S6) and the calculating section 224 calculates the ratio of the measured time to the period of one beat.

Then, the second comparing section 225 determines whether the result calculated in the calculating section 224 exceeds 47% or not (Step S8). When this result exceeds 47%, the stage is forwarded to the next step (Step S9) in which the pulse condition is judged to be a Ping mai which allows the data yielding section 226 to yield the pulse condition data ZD2. On the other hand, when the result calculated in the calculating section 224 does not exceed 47%, the stage is forwarded to the next step (Step S10) in which the pulse condition is judged to be a Hua mai to yield the pulse condition data ZD3 in the data yielding section 226.

As stated above, the pulse wave examination apparatus 1 according to the third embodiment judges the pulse condition on the basis of the autocorrelation data RD of the pulse waveform MH and hence the subject and a doctor can know the living condition from the detected result of the pulse wave.

3.4 Modification of the Third Embodiment (1) In the forgoing third embodiment, the minimum value detecting section 221 calculates the autocorrelation data RD in a period of one heartbeat. However, the minimum value detecting section 221 can be arranged so that the minimum values of the autocorrelation data RD detected in each of plural heartbeat periods are averaged to determine the average of the minimum values. In this case, because the minimum values are averaged, variations in the minimum values caused by noise can be restrained. This can improve the accuracy in making a determination as to whether or not the pulse condition is a Hua mai.

(2) In the third embodiment mentioned above, although the calculating section 224 calculates the ratio of the measured time to the period of one heartbeat, it may calculate the average of the ratios detected in each of plural heartbeat periods to output the average ratio. This can improve the accuracy in determining whether the pulse condition is a Ping mai or Hua mai because the ratios are averaged to thereby restrain variations caused by noise.

(3) Comparing the autocorrelation coefficients R($\tau$) of a typical Ping mai and Hua mai (see FIGS. 17 and 18), a difference can be observed in width between the autocorrelation coefficients R($\tau$) within the range between 0.4 and 0.8. Because of this, the time measuring section 223 may measure a time interval in which the autocorrelation coefficient exceeds a threshold value prescribed within a range between 0.4 and 0.8, and the second comparing section 225 may determine whether the pulse condition is a Ping mai or a Hua mai on the basis of the time interval corresponding to this threshold value.

4. Fourth Embodiment

Next, a pulse wave examination apparatus of a fourth embodiment of the present invention will be described.

4.1 Electrical Structure of the Pulse Wave Examination Apparatus

The electrical structure of the pulse wave examination apparatus of the fourth embodiment is the same as that of the third embodiment except for the structure of a pulse condition data yielding section 220.

Figure 21:
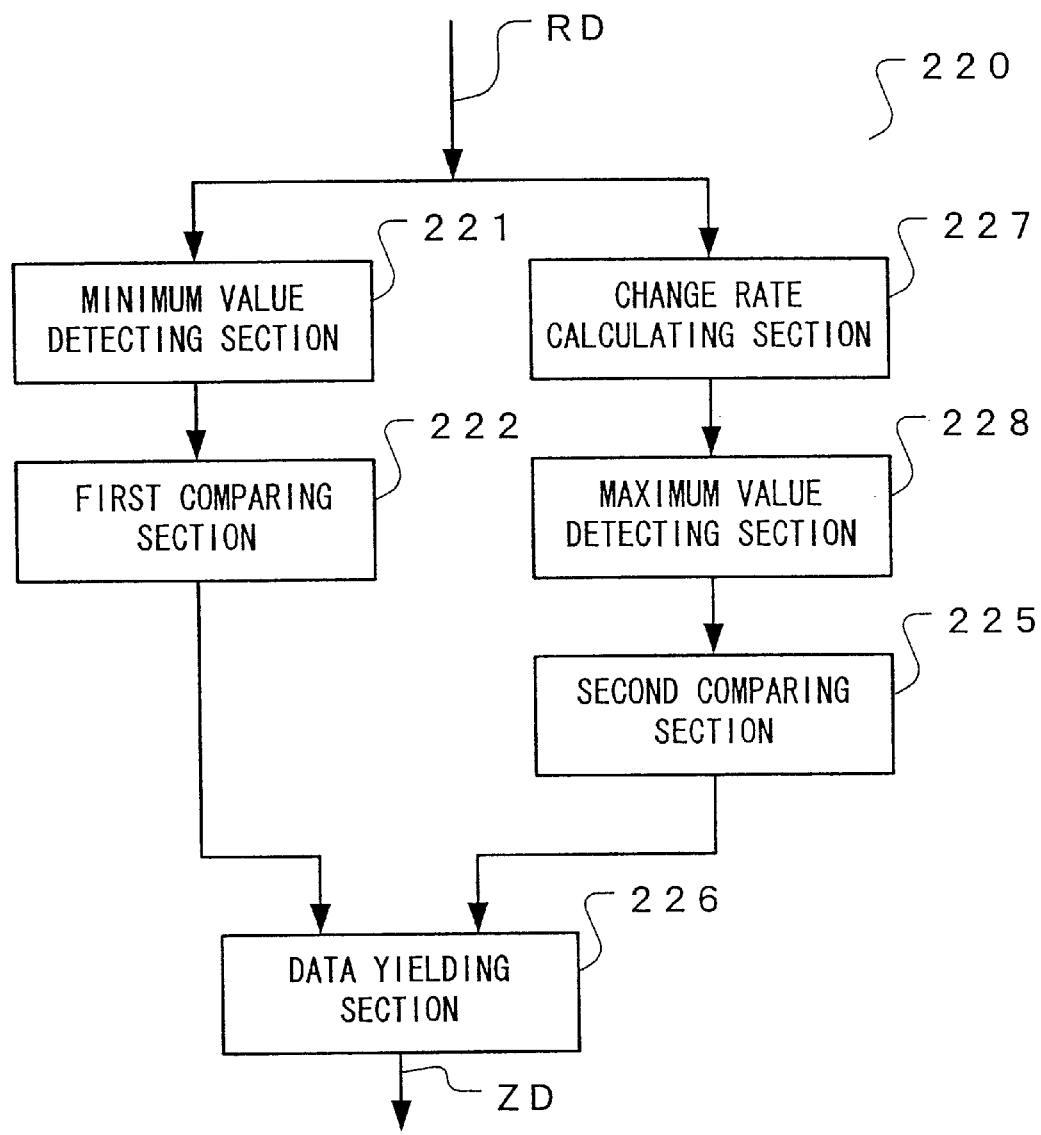
FIG. 21 is a block diagram of a pulse condition data yielding section according to a fourth embodiment.

The electrical structure of the pulse condition data yielding section 220 according to the fourth embodiment will be described as follows. FIG. 21 is a block diagram of the pulse condition data yielding section 220 according to the fourth embodiment.

The pulse condition data yielding section 220 in this embodiment comprises a minimum value detecting section 221 and a first comparing section 222 for determining whether the pulse condition is a Xuan mai or not, a change rate calculating section 227, a maximum value detecting section 228 and a second comparing section 225 for determining whether the pulse condition is a Ping mai or a Hua mai, and a data yielding section 226 for yielding a pulse condition data ZD on the basis of these determined results.

First, the first comparing section 222 determines whether the pulse condition is a Xuan mai or not based on whether the minimum value of the autocorrelation data RD detected by the minimum value detecting section 221 exceeds 0.25 or not as in the third embodiment.

Figure 22:
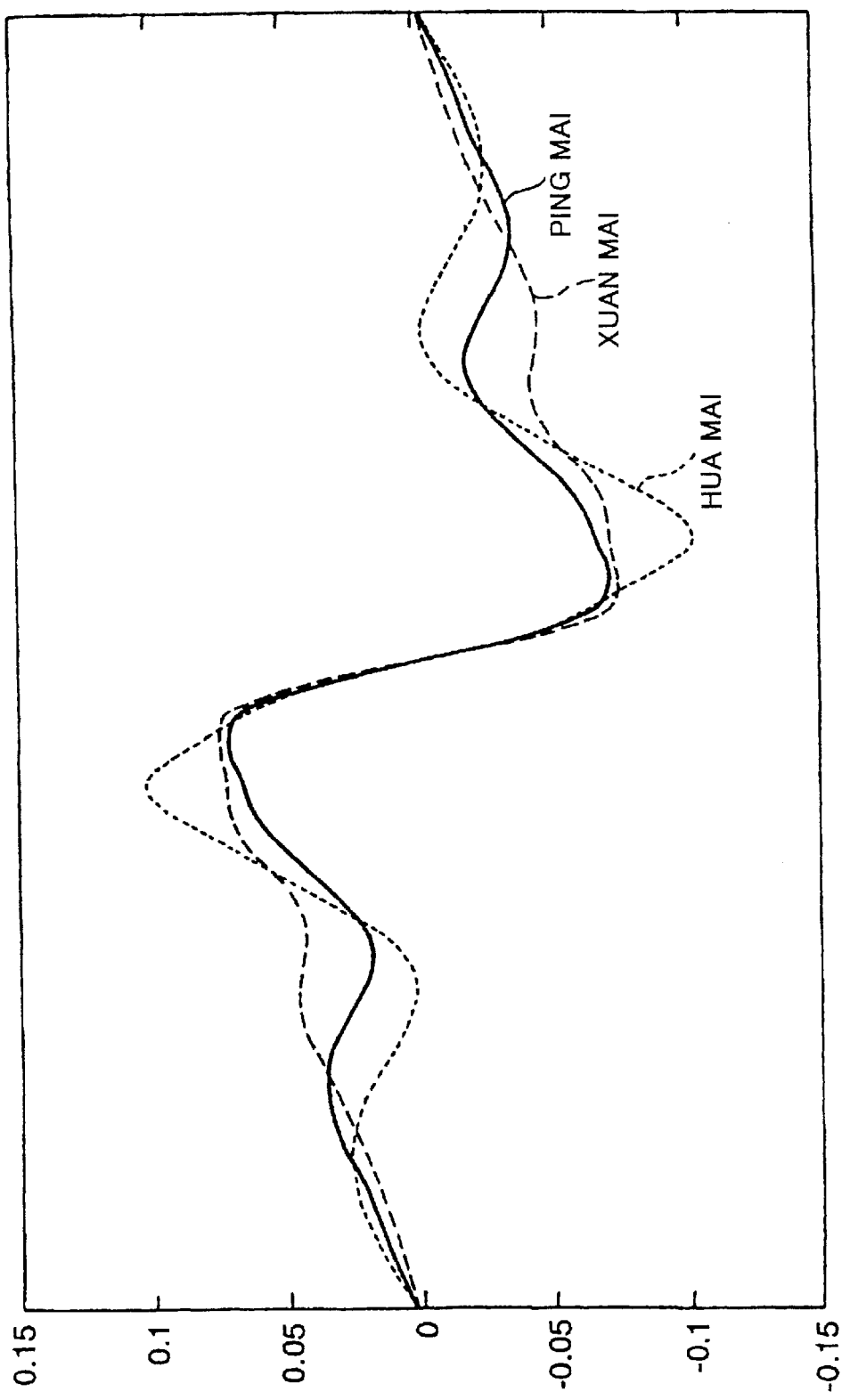
FIG. 22 is a view showing the rate of variation in autocorrelation data of a typical pulse waveform.

Next, the change rate calculating section 227 calculates the change rate RDd of the autocorrelation data RD. If the autocorrelation data RD is as shown in FIGS. 16 to 18, each change rate RDd of a Xuan mai, Ping mai and Hua mai is as shown in FIG. 22. It is seen from this figure that the maximum value of the change rate RDd is about 0.1 in a Hua mai whereas it is 0.072 in a Ping mai. This corresponds to the fact that the waviness of the pulse waveform MH of a Ping mai is greater than that of the pulse waveform of a Hua mai. It is therefore possible to determine whether the pulse condition is a Ping mai or a Hua mai by the maximum value of the change rate RDd. When the maximum value of the change rate RDd exceeds 0.085, the pulse condition may be judged to be a Hua mai whereas, when it does not exceeds 0.085, the pulse condition may be judged to be a Ping mai accordingly.

Then, the maximum value detecting section 228 detects the maximum of the change rate RDd within a prescribed period of time longer than a period of one beat. The second comparing section 225 compares the maximum value of the change rate with a prescribed threshold value (0.85) to determine whether the maximum value of the change rate RDd exceeds the threshold value or not.

The data yielding section 226 yields a pulse condition data ZD on the basis of each result determined by the first and second comparing sections 222 and 225. First, when the minimum value is judged to be less than 0.25 in the first comparing section 222, a pulse condition ZD1 showing a Hua mai is obtained. Then, when the maximum value of the change rate RDd is judged to be less than 0.85 in the second comparing section 225, pulse condition data ZD2 showing a Ping mai is obtained whereas, when it is judged to exceed 0.85, a pulse condition data ZD3 showing a Hua mai results.

4.2 Action of the Pulse Wave Examination Apparatus

Figure 23:
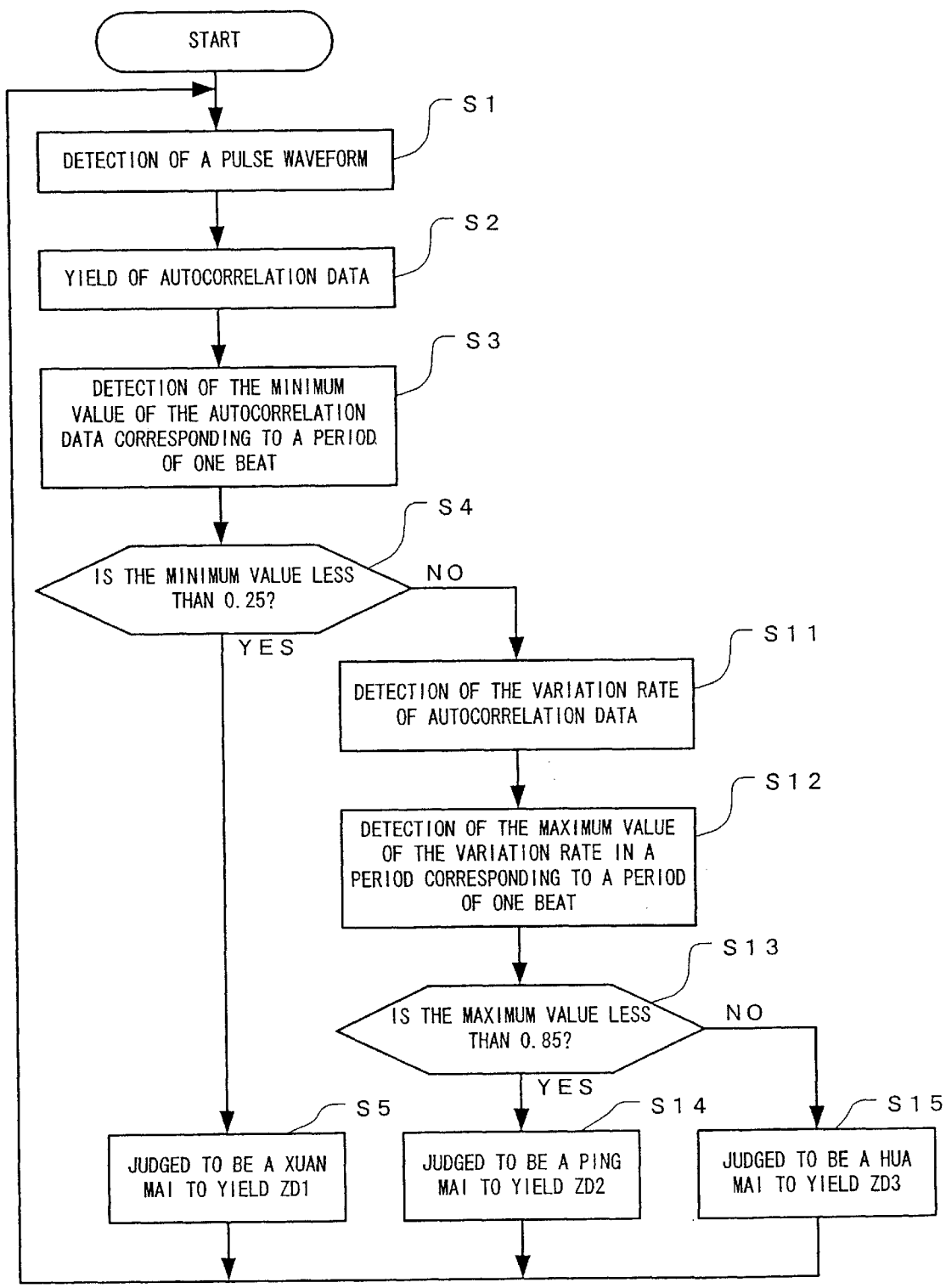
FIG. 23 is a flow chart showing the action of a pulse wave examination apparatus of the fourth embodiment.

Next, the action of the pulse wave examination apparatus of the fourth embodiment will be described. FIG. 23 is a flow chart showing the action of the pulse wave examination apparatus. The actions from Step S1 to Step S5 are the same as those of the pulse wave examination apparatus of the third embodiment described with reference to FIG. 20 and hence description of these steps is omitted.

In Step S11, when the change rate calculating section 227 detects the change rate RDd of the autocorrelation data RD, the maximum value detecting section 228 detects the maximum value of the change rate RDd in a period corresponding to a period of one beat (Step S12). For instance, if the calculated change rate RDd is that of a Hua mai shown in FIG. 22, a value of about 0.1 is detected as the maximum value.

Then, the second comparing section 225 determines whether or not the maximum value exceeds 0.85. When the maximum value is found to be less than 0.85, the stage is forwarded to Step S14 in which the pulse condition is judged to be a Ping mai and the data yielding section 226 yields pulse condition data ZD2. On the other hand, when the maximum value is found to exceed 0.85, the stage is forwarded to Step S15 in which the pulse condition is judged to be a Hua mai and the data yielding section 226 produces pulse condition data ZD3.

In the fourth embodiment, as stated above, attention is given to the point that there is a difference between a Ping mai and a Hua mai in the maximum value of the change rate RDd of the autocorrelation data RD. The maximum value of the change rate RDd is compared with the threshold value to determine whether the pulse condition is a Ping mai or a Hua mai. Thus, even a person having no knowledge of pulse detection can find the exact pulse condition.

5. Fifth Embodiment

In the pulse wave examination apparatus 1 according to the third and fourth embodiments, the autocorrelation data RD is obtained based on the pulse waveform MH output from the pulse wave detecting section 10 to judge the pulse condition. However, when a subject walks and goes about daily life, the body movement causes the blood flow of the subject to fluctuate. Because of this, a component due to the body movement is superimposed on the pulse waveform MH output from the pulse wave detecting section 10. The magnitude of the body movement component depends on the degree of movement. When the quantity of the movement is large, the body movement component superimposed on the pulse waveform MH increases, causing difficulty in making an exact judgment of the pulse condition. Hence, in the fifth embodiment of the present invention, the body movement component is eliminated from the pulse waveform MH and the pulse condition is judged based on the resulting pulse waveform.

5.1 Electrical Structure of the Pulse Wave Examination Apparatus

Figure 24:
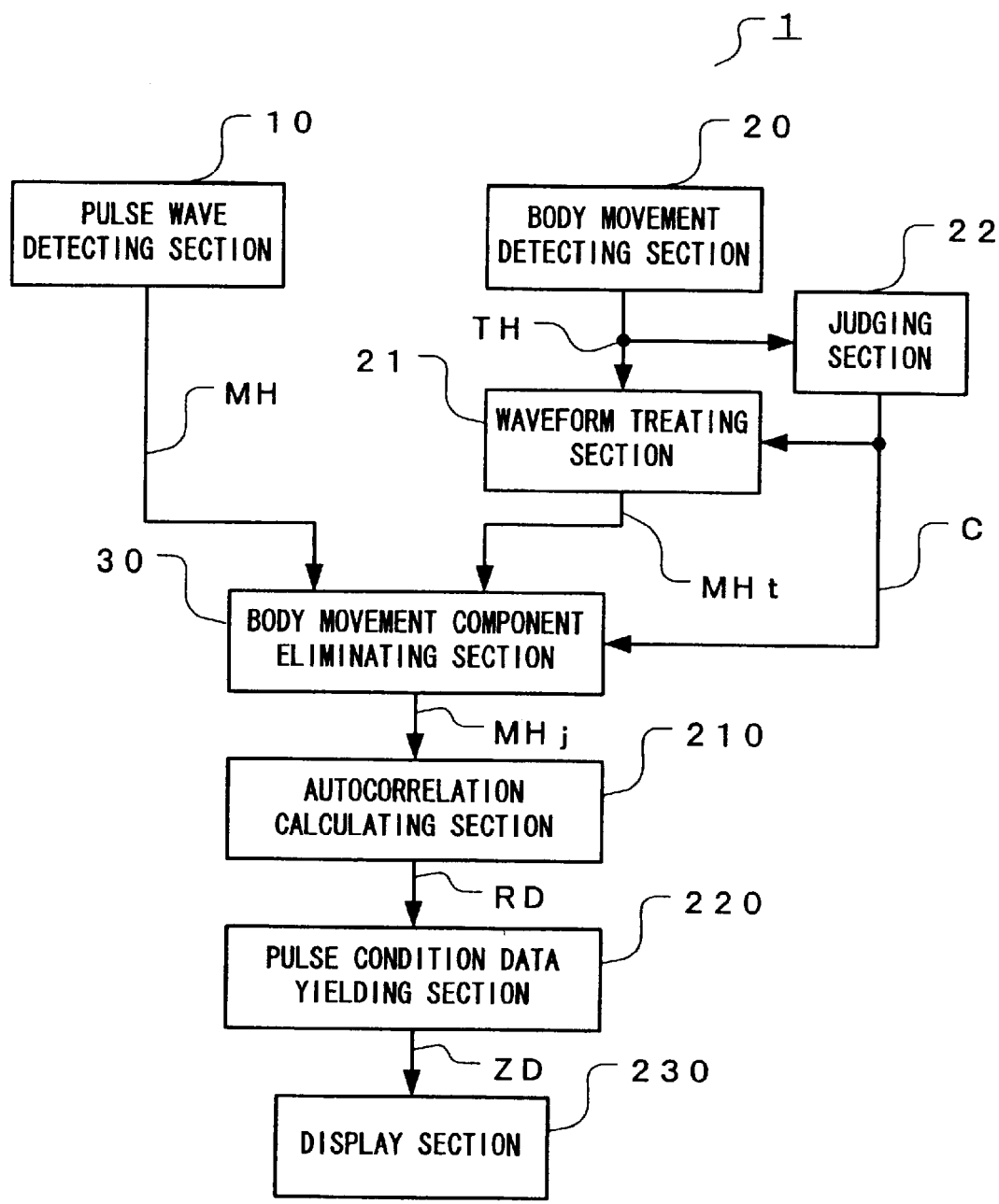
FIG. 24 is a block diagram showing the electrical structure of a pulse wave examination apparatus of a fifth embodiment.

FIG. 24 is a block diagram showing the electrical structure of the pulse wave examination apparatus according to the fifth embodiment of the present invention. Each structure of the autocorrelation calculating section 210, pulse condition data yielding section 220 and display section 230 in this embodiment is the same as described in the third and fourth embodiments, therefore further description of these sections is omitted. Also, a body movement eliminating section 30 and sections prior to this section, namely, a pulse wave detecting section 10, a body movement detecting section 20, a judging section 22, and a waveform treating section 21 are the same as those described in the first embodiment. Therefore, further description of these sections is omitted.

The pulse wave examination apparatus of this embodiment provides a body movement-eliminated pulse waveform MHj owing to the above structure. The autocorrelation calculating section 210 can yield the autocorrelation data RD on the basis of the body movement-eliminated pulse waveform MHj. According to the pulse wave examination apparatus 1 of this embodiment, the pulse condition can be specified in a condition free of the influence of body movement.

6. Sixth Embodiment

Next, a pulse wave examination apparatus 1 according to a sixth embodiment of the present invention will be described.

Figure 25:
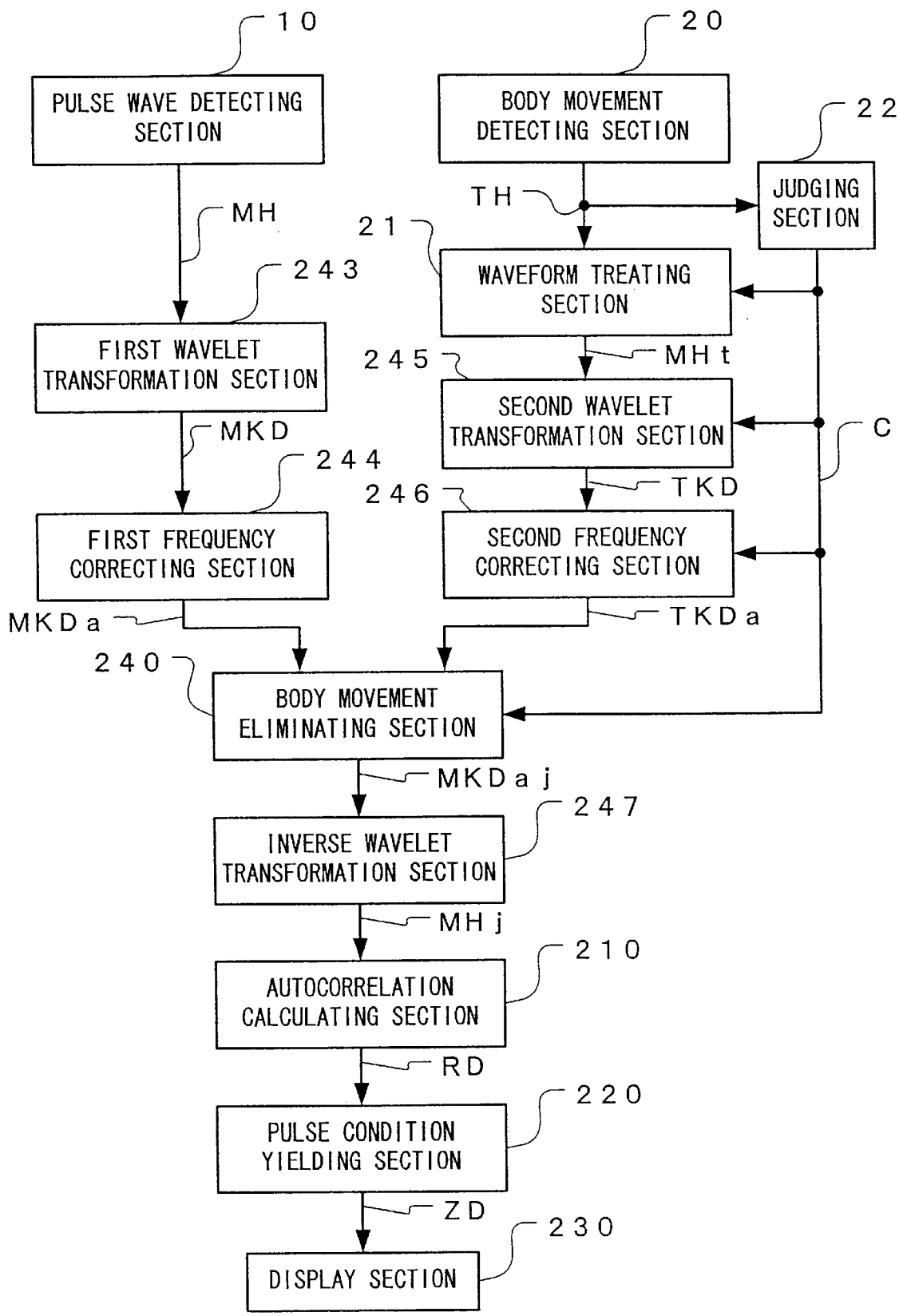
FIG. 25 is a block diagram showing the electrical structure of a pulse wave examination apparatus of a sixth embodiment.

FIG. 25 is a block diagram of a pulse wave examination apparatus 1 according to the sixth embodiment. In the sixth embodiment, though a body movement component TH is detected using a body movement detecting section 20 and a waveform treating section 21, as in the fifth embodiment, the sixth embodiment differs from the fifth embodiment in that the elimination of body movement mentioned in the fifth embodiment is made using wavelet transformation.

6.1 First and Second Wavelet Transformation Sections and First and Second Frequency Correcting Section In FIG. 25, a first wavelet transformation section 243 undergoes a well-known wavelet transformation of a pulse waveform MH output from the pulse wave detecting section 10 to yield a pulse wave analysis data MKD. Then, the second wavelet transformation section 245 undergoes a well-known wavelet transformation of a body movement waveform TH output from the body movement detecting section 20 to yield a body movement analysis data TKD. These first and second wavelet transformation sections 243 and 245 have the same structures as those described in the second embodiment.

Figure 26:
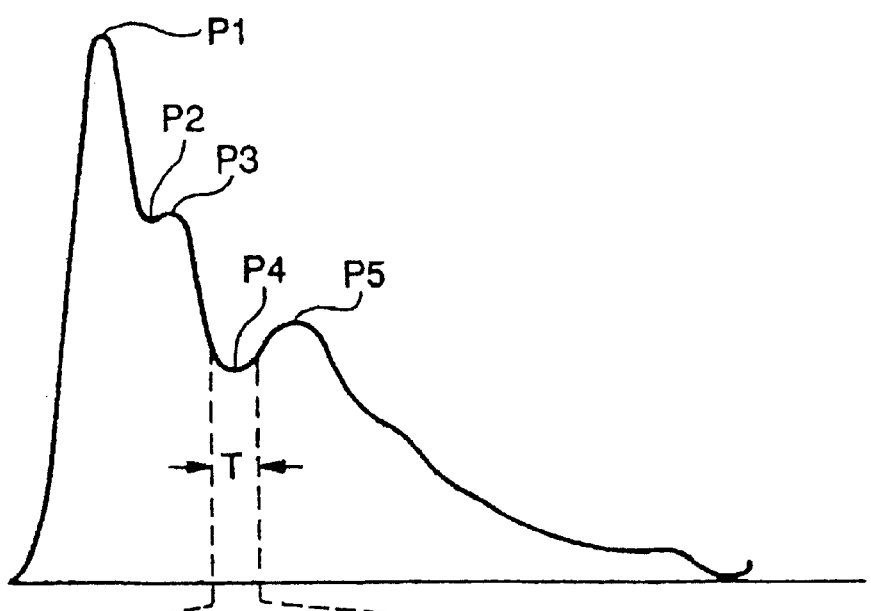
FIG. 26 is a view showing pulse wave analysis data during a partial period in a pulse waveform.

FIG. 26 shows the pulse wave analysis data MKD in part of the period of the pulse waveform MH. In the figure, a period T is close to a peak P4 and the pulse wave analysis data MKD is obtained at time intervals set by dividing the period T into 8 parts. Meanwhile, in the wavelet transformation, the frequency resolution and the time resolution is in tradeoff relation. Hence, if the frequency resolution is sacrificed, the pulse wave analysis data can be obtained at more reduced intervals.

The first frequency correcting section 244 makes frequency corrections of the pulse analysis data MKD. In the aforementioned equation (2), the term "$1/a^{1/2}$" corresponding to the frequency is present. The effect of this term must be corrected when data is compared between different frequency zones. A first frequency correcting section 244 is therefore provided and multiplies a wavelet data WD by a factor $a^{1/2}$ to yield pulse wave-corrected data MKDa. This enables a correction on the basis of each corresponding frequency so as to obtain a constant power density per frequency. Moreover, the second frequency correcting section 246 makes the frequency correction of the body movement analysis data TKD in the same manner as in the case of the first frequency correcting section 244 to produce a body movement-corrected data TKDa from the body movement analysis data TKD.

6.2 Body Movement Component Eliminating Section

Figure 27:
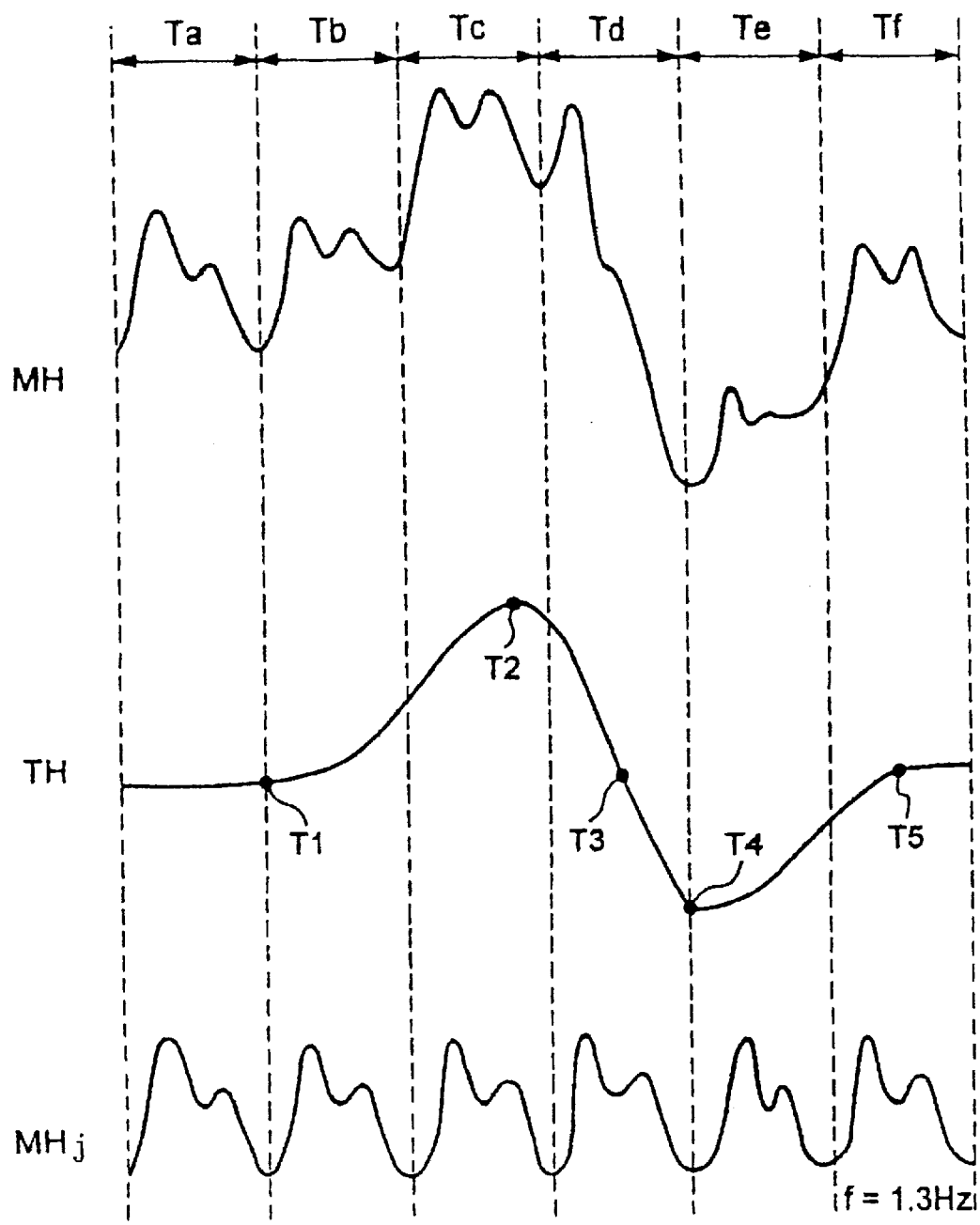
FIG. 27 is a timing chart for describing the action of a body movement eliminating section according to the sixth embodiment.

Next, a body movement component eliminating section 240 subtracts the body movement-corrected data TKDa from the pulse wave-corrected data MKDa to yield a body movement-eliminated pulse wave data MKDaj. This will be described in detail. Incidentally, in the following description, the body movement is analyzed on the assumption that the subject lifts a cup with his hand and then puts it back in the original location. In this case, the pulse waveform MH shown in FIG. 27 is detected by the pulse wave detecting section 10 and, at the same time, the body waveform TH is detected by the the body movement detecting section 20.

Here, the body waveform TH starts to increase from time T1, reaches a positive peak at time T2, decreases gradually, passes a level 0 at time T3, reaches a negative peak at time T4 and returns to a level 0 at time T5. The body movement waveform TH is detected by the body movement detecting section 20 using an acceleration sensor. The time T3 corresponds to the time at which the subject has lifted the cup to the maximum height, the time T1 corresponds to the time at which the lifting starts, and the time T4 corresponds to the time at which the lifting has finished. Accordingly the period between the time T1 and the time T4 is the period in which body movement is present. The pulse waveform MHj shown in FIG. 27 is a pulse waveform formed on the assumption that no body movement is present. In this embodiment also, the frequency of the fundamental wave of the pulse waveform MH is 1.3 Hz.

FIG. 28 shows the pulse wave-corrected data MKDa in a period Tc (see FIG. 27) and FIG. 29 shows the body movement-corrected data TKDa in the period Tc. It is seen from this figure that frequency components with a relatively large level are present in a frequency zone between 0.0 Hz and 1.0 Hz in the body movement waveform TH. When the pulse wave-corrected data MKDa and the body movement-corrected data TKDa are supplied to the body movement eliminating section 240, the body movement eliminating section 240 subtracts the body movement-corrected data TKDa from the pulse wave-corrected data MKDa to yield a body movement-eliminated pulse wave data MKDaj excluding the body movement component as shown in FIG. 30. This makes it possible to eliminate the effect of body movement even if body movement is present.

6.3 Judging Section

Next, the judging section 22 compares the body movement waveform TH with a prescribed threshold value to yield a control signal C showing the presence or absence of body movement, and supplies this signal to the waveform treating section 21, the second wavelet converting section 245, and the second frequency correcting section 246. This ensures that each operation of the waveform treating section 21, the second wavelet converting section 245, and the second frequency correcting section 246 is suspended when there is no body movement, thereby reducing calculation time and power consumption and improving the SN ratio.

6.4 Inverse Wavelet Transformation Section

Next, an inverse wavelet transformation section 247 undergoes the inverse wavelet transformation of the body movement-eliminated pulse wave data MKDaj to yield a body movement-eliminated pulse waveform MHj. In this case, the inverse wavelet transformation section 247 undergoes the inverse wavelet transformation based on the equation (4) to reconstruct the waveform.

$$f(x) = \frac{1}{C_\psi} \int \int_{\mathcal{R}^2} (W_\psi f)(b, a) \frac{1}{\sqrt{a}} \psi\left(\frac{x-b}{a}\right) \frac{dadb}{a^2} \tag{4}$$

Then, as in the fifth embodiment, the autocorrelation calculating section 210 produces autocorrelation data RD on the basis of the body movement-eliminated pulse waveform MHj.

After that, the pulse condition data yielding section 220 yields pulse condition data ZD on the basis of the autocorrelation RD and the display section 230 then displays such characters as "Ping mai", "Xuan mai" and "Hua mai" indicated by the pulse condition data ZD, or characters corresponding to each pulse condition. The display section 230 ensures that the subject or a doctor can find the pulse condition.

As stated above, the sixth embodiment is designed so that the autocorrelation data RD is yielded based on the body movement-eliminated pulse waveform MHj excluding a body movement component, hence the subject can detect his pulse condition continuously in his daily life.

7. Seventh Embodiment

In the fifth and sixth embodiments, the body movement waveform TH is detected by the body movement detecting section 20, the pulse waveform MH is compared with the body movement waveform TH, a body movement component included in the frequency component of the pulse waveform MH is eliminated to calculate the autocorrelation data RD thereby specifying the pulse condition. The above structure, however, requires the body movement section 20 and the waveform treating section 21, causing the structure to be complicated. A seventh embodiment of the present invention is developed in view of this situation and provides a pulse wave examination apparatus which has a simple structure and can detect a pulse condition exactly even if body movement exists.

Figure 31:
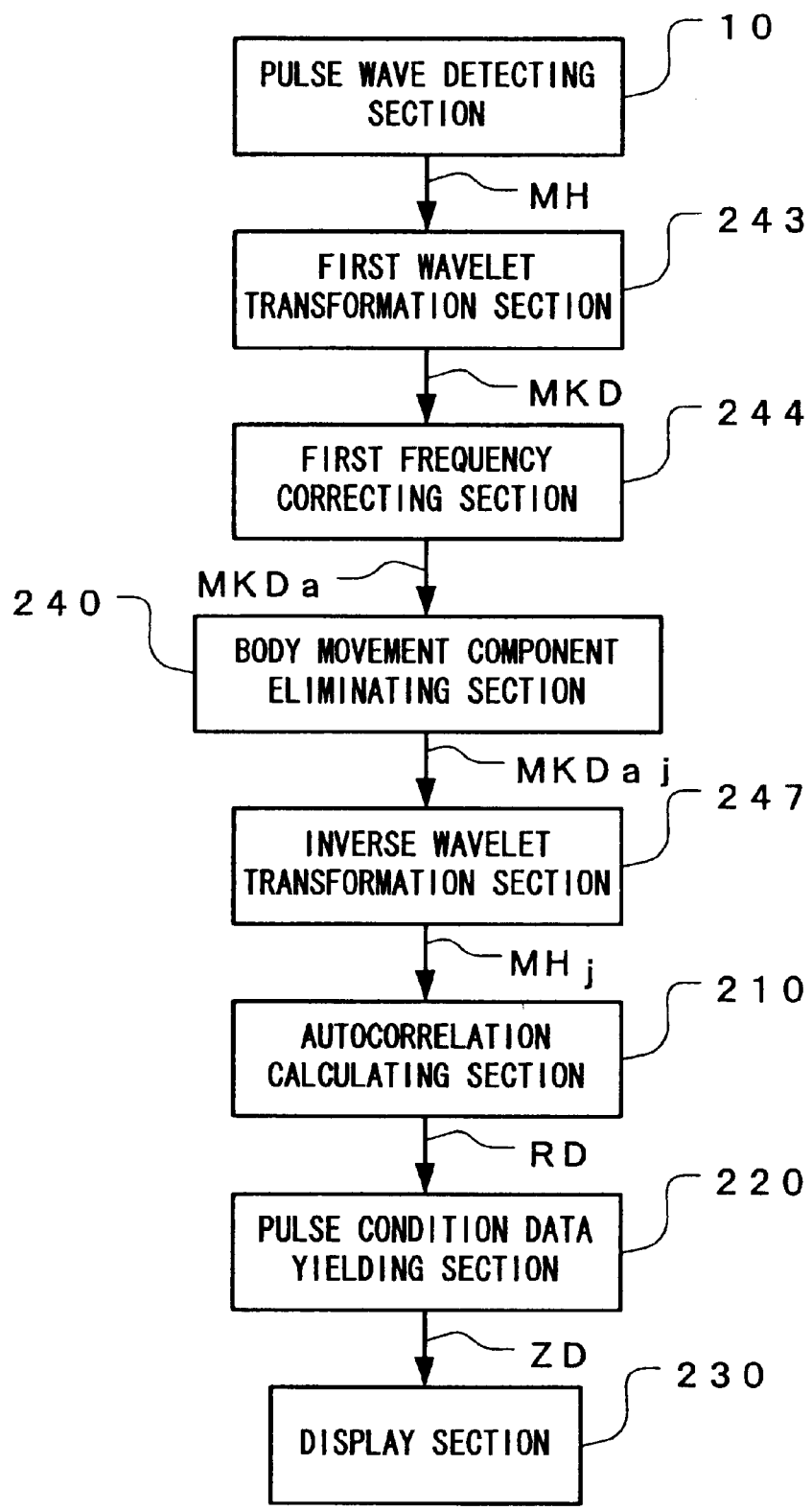
FIG. 31 is a block diagram showing the electrical structure of a pulse wave examination apparatus of a seventh embodiment.

FIG. 31 is a block diagram of the pulse wave examination apparatus according to the seventh embodiment, which is the same as the pulse wave examination apparatus according to the sixth embodiment shown in FIG. 25 except that the body movement detecting section 20, the waveform treating section 21, the second wavelet transformation section 245 and the second frequency correcting section 246 are omitted and except for the inner structure of the body movement component eliminating section 240. The following is a description of the difference between the two embodiments.

A body movement component eliminating section 240 separates and removes a body movement component from the pulse wave-corrected data MKDa to yield body movement-eliminated pulse wave data MKDaj. Here, the body movement component eliminating section 240 makes use of the property of body movement as will be mentioned below.

The body movement is caused by the up-and-down motion of an arm or the swing of an arm. However, there are few chances of experiencing instant motion of the living body in daily life. The frequency component of the body movement waveform TH is not very high and is usually in a range between 0 Hz and 1 Hz in daily life. In this case, most of the frequency of the fundamental wave of the pulse waveform is in a range between 1 Hz and 2 Hz. In daily life, therefore, the frequency component of the body movement waveform TH is in a frequency zone lower than the fundamental frequency of the pulse waveform MH.

On the other hand, while engaging in a sport, e.g., jogging, the frequency component of the body movement waveform TH is slightly increased by the effect of the swing of an arm and the like. However, the number of beats increases in relation to the quantity of movement and the frequency of the fundamental wave of the pulse waveform MH is thereby increased at the same time. Therefore, even during a sport, the frequency component of the body movement waveform TH is in a frequency zone lower than the fundamental frequency of the pulse waveform MH, in general.

The body movement component eliminating section 240 separates a body movement component taking the above fact into consideration. specifically, it is structured so as to neglect a frequency zone lower than that of the fundamental wave component of the pulse waveform MH. In this case, if the body movement component is present in a frequency zone higher than that of the fundamental wave component of the pulse waveform MH, the accuracy in the detection of a cardiac function is reduced. However, as aforementioned, the probability that the body movement component is in a frequency zone lower than that of the component of the fundamental wave of the pulse waveform MH is high. The pulse condition can be diagnosed with high accuracy accordingly.

Figures 32, 33:
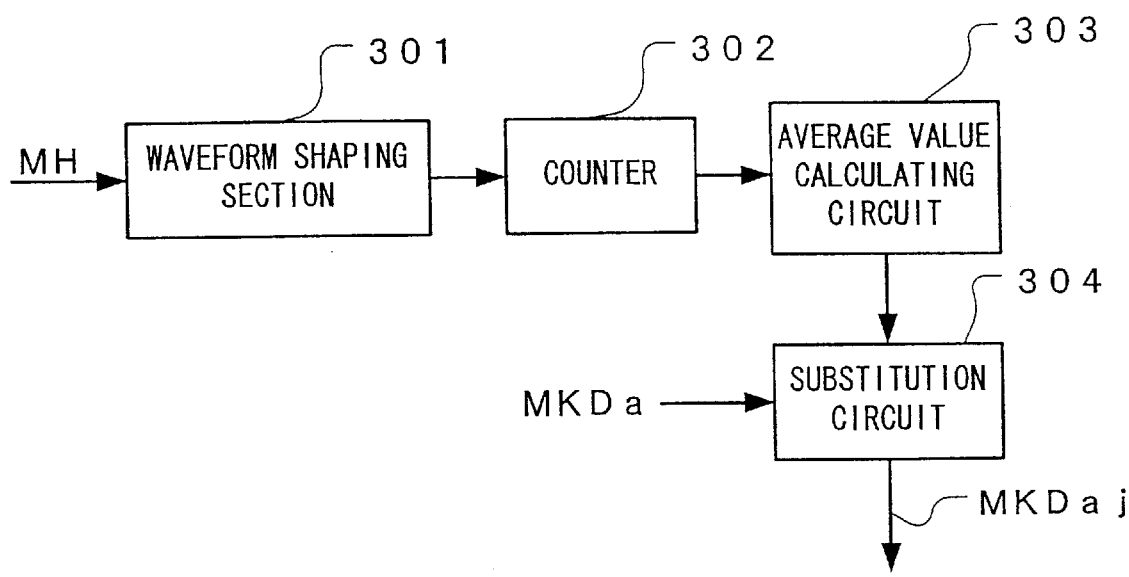
FIG. 32 is a block diagram of a body movement eliminating section of the seventh embodiment.
FIG. 33 is a view showing an example of body movement-eliminated pulse wave data of the seventh embodiment.

FIG. 32 is a block diagram of the body movement eliminating section 240. A waveform shaping section 301 provides the pulse waveform MH with waveform shaping and yields a reset pulse synchronized with the pulse waveform MH. A counter 302 measures the number of clock pulses though not shown. The count number of the counter 302 is reset by the above reset pulse. An average value calculating circuit 303 calculates the average value of the count number of the counter 302. In this case, the average value calculated by the average value calculating circuit 303 corresponds to the mean period of the pulse waveform MH. The frequency of the fundamental wave of the pulse waveform MH can be detected with reference to the average value.

Next, a substitution circuit 304 specifies a frequency region including the frequency of the fundamental wave of the pulse waveform MH on the basis of the aforementioned average value. For instance, when the average value shows 0.71 seconds, the frequency of the fundamental wave becomes 1.4 Hz. The frequency region to be specified becomes 1 Hz to 1.5 Hz. Then, the substitution circuit 304 replaces the pulse wave-corrected data MKDa with 0 in a frequency region less than a specified frequency region to yield the body movement-eliminated pulse wave data MKDaj. A component of a frequency region less than the frequency of the fundamental wave of the pulse waveform MH is thereby neglected. In this case, a pulse wave component as well as a body movement component are replaced with 0. However, because the characteristic portion of the pulse waveform MH exists in a frequency zone higher than the frequency of the fundamental wave of the pulse waveform MH, the replacement of the pulse wave component with 0 has almost no effect on the pulse waveform.

If, for instance, the pulse waveform MH (the frequency of its fundamental wave: 1.3 Hz) shown in FIG. 27 is detected by the pulse wave detecting section 10, the pulse wave-corrected data MKDa in the period Tc is as shown in FIG. 28.

In this case, the frequency zone specified by the substitution circuit 304 is in a range between 1.0 Hz and 1.5 Hz and hence the frequency zone subjected to the substitution is in ranges between 0.5 Hz and 1.0 Hz and between 0 Hz and 0.5 Hz. Data in a frequency range between 0 and 1 Hz in the pulse wave-corrected data MKDa is replaced with 0 and the body movement-eliminated pulse wave data MKDaj shown in FIG. 33 is obtained.

When the body movement-eliminated pulse wave data MKDaj obtained in this manner is transformed into the body movement-eliminated waveform MHj by the inverse wavelet transformation section 247, the autocorrelation calculating section 210 yields autocorrelation data RD on the basis of the body movement-eliminated pulse wave form MHj as in the fifth embodiment. Then, based on the autocorrelation data RD, the pulse condition data yielding section 220 yields pulse condition data ZD and the display section 230 then displays such characters as "Ping mai", 37 Xuan mai" and "Hua mai" indicated by the pulse condition data ZD, or characters corresponding to each pulse condition. The display section 230 ensures that the subject or a third party, e.g., a doctor can find the pulse condition.

As described above, the seventh embodiment is designed to yield the autocorrelation data RD on the basis of the body movement-eliminated pulse wave MHj excluding a body movement component. So the subject can find his pulse condition continuously in his daily life.

The seventh embodiment also makes clever use of the characteristics of a body movement in which the possibility that a component of body movement exists in a frequency zone less than that of the frequency component of the fundamental wave of the pulse waveform MH is high, to thereby remove the body movement component. In this embodiment, therefore, components such as the body movement detecting section 20 and the waveform treating section 21 that are required in the third and fourth embodiments may be omitted and the pulse condition can be exactly detected even if a body movement exists.

8. Eighth Embodiment

The autocorrelation data RD is obtained based on the pulse waveform MH in the third and fourth embodiments and on the body movement-eliminated pulse waveform MHj in the fifth to seventh embodiments. In the aforementioned wavelet transformation, analysis data can be obtained at each frequency zone which is periodically divided. Here, the characteristic portions of the pulse waveform MH and body movement-eliminated pulse waveform MHj are in the positive or negative peak. Also, when these peaks appear, the value of the analysis data resulting from wavelet transformation increases in a relatively high frequency zone. If attention is focused on a certain frequency zone and autocorrelation data RD with respect to the analysis data in the focused frequency zone is obtained, it is therefore possible to specify the pulse condition on the basis of the autocorrelation data RD. The eighth embodiment of the present invention is developed in the light of the above point.

Figure 34:
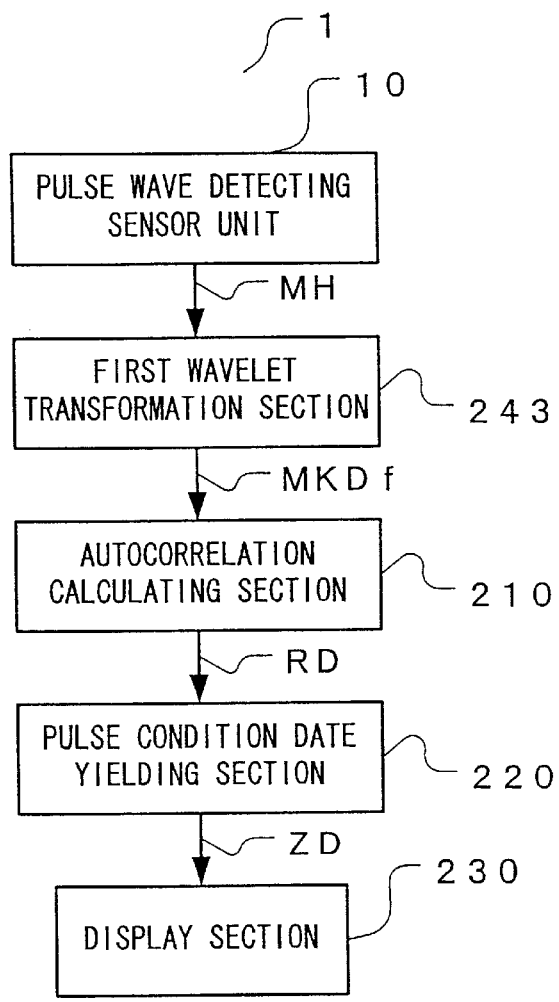
FIG. 34 is a block diagram showing the electrical structure of a pulse wave examination apparatus of an eighth embodiment.

FIG. 34 shows a block diagram of the pulse wave examination apparatus according to the eighth embodiment. In the figure, when a pulse waveform MH is detected by a pulse wave detecting section 10, a first wavelet transformation section 243 undergoes the wavelet transformation of the pulse waveform MH to yield a pulse wave analysis data MKDf corresponding to a specific frequency zone. For instance, as shown in FIG. 26, if, in the wavelet transformation, the frequency zone is divided into eight zones and the focused frequency zone is in a range between 3.0 Hz and 2.5 Hz, M16 to M86 are output as the pulse wave analysis data MKDf.

Figure 35:
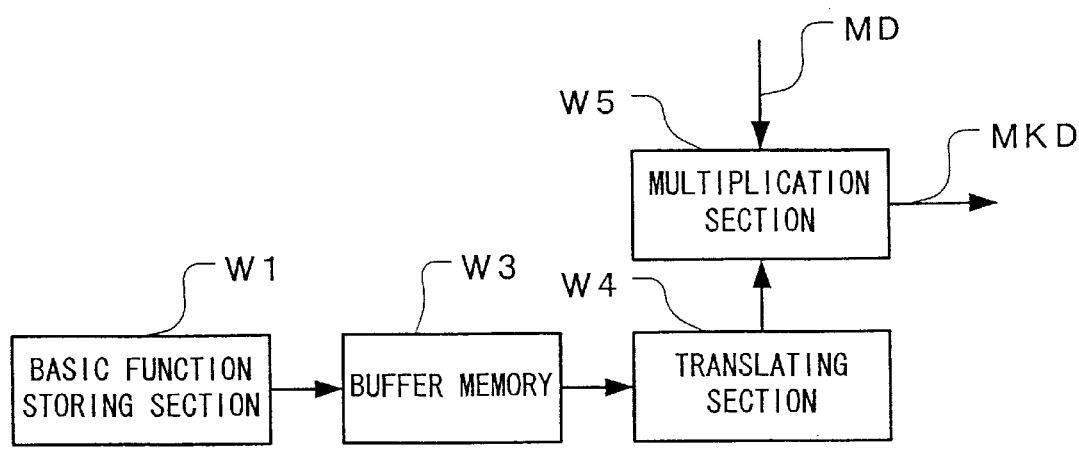
FIG. 35 is a block diagram of a first wavelet conversion section of the eighth embodiment.

In this case, the first wavelet transformation section 243 is structured as shown in FIG. 35. Comparing FIG. 35 with FIG. 4, it is seen that the scale conversion section W2 is omitted. The reason is that the scale conversion section W2 is a type converting the scale parameter "a" corresponding to the period, hence this function may be attained only by storing a mother wavelet corresponding to the focused frequency zone in the basic function storing section W1.

The pulse wave analysis data MKDf obtained in this manner shows a variation of the characteristic portion of the pulse waveform MH with time. Hence the pulse waveform MH can be analyzed efficiently by calculating the autocorrelation coefficient of the pulse wave analysis data MKDf. So an autocorrelation calculating section 210 in this embodiment provides autocorrelation data RD showing the autocorrelation coefficient of the pulse wave analysis data MKDf.

Next, a pulse condition data yielding section 220 produces pulse condition data ZD on the basis of the autocorrelation data RD. In this case, the pulse condition data yielding section 220 treats the autocorrelation data RD arithmetically and compares the calculated result with a threshold value designed to identify the pulse condition to yield the pulse condition data ZD. When the pulse condition data ZD is supplied to a display section 230, the display section 230 displays the characters "Xuan mai", "Ping mai", and "Hua mai" and the like. This ensures that the subject or a third party, e.g., a doctor, can find the pulse condition.

9. Ninth Embodiment

A ninth embodiment of the present invention is structured by applying a technique using wavelets for removing a body movement component to the pulse wave examination apparatus 1 of the eight embodiment.

Figure 36:
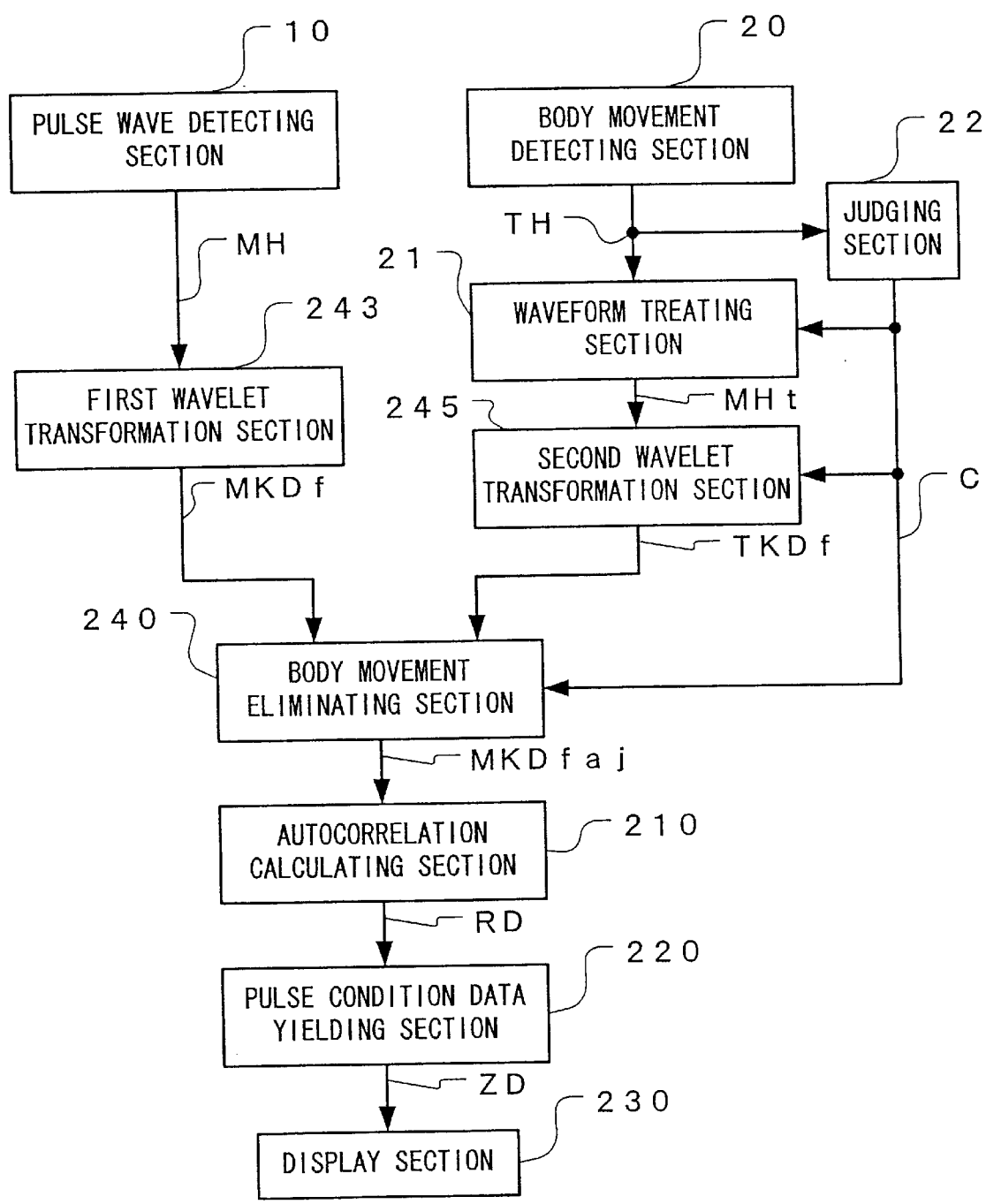
FIG. 36 is a block diagram showing the electrical structure of a pulse wave examination apparatus of a ninth embodiment.

FIG. 36 is a block diagram of a pulse wave examination apparatus 1 according to the ninth embodiment. In this embodiment, a first wavelet transformation section 243 and a second wavelet transformation section 245 are structured as shown in FIG. 35, as in the aforementioned eighth embodiment. The first and second wavelet transformation 243 and 245 provide pulse wave analysis data MKDf and body movement analysis data TKDf respectively, corresponding to a focused frequency zone. A body movement component eliminating section 240 subtracts the body movement analysis data TKDf from the pulse wave analysis data MKDf to yield a body movement-eliminated analysis data MKDfaj.

When the body movement-eliminated analysis data MKDfaj is produced, an autocorrelation calculating section 210 provides autocorrelation data RD showing the autocorrelation coefficient on the basis of the body movement-eliminated analysis data MKDfaj, as in the eighth embodiment. Next, a pulse condition data yielding section 220 produces pulse condition data ZD on the basis of the autocorrelation data RD. In this case, the pulse condition data yielding section 220 treats the autocorrelation data RD arithmetically and compares the calculated result with a threshold value designed to identify the pulse condition to yield pulse condition data ZD. When the pulse condition data ZD is supplied to a display section 230, the display section 230 displays the characters "Xuan mai", "Ping mai", and "Hua mai" and the like. This ensures that the subject or a third party, e.g., a doctor can find the pulse condition.

As stated above, in the ninth embodiment, attention is focused on a certain frequency zone and wavelet transformation is carried out to eliminate a body movement component. It is therefore unnecessary to compare the results of wavelet transformation between different frequency zones. Therefore, the first and second frequency correcting sections 244 and 246 may be omitted. Furthermore, the autocorrelation data RD is yielded directly from the body movement-eliminated analysis data MKDfaj so that the inverse wavelet transformation section 247 may be omitted.

10. External Structure of the Aforementioned Embodiments

Next, some instances of the external structures of pulse wave examination apparatuses according to the aforementioned first to ninth embodiments of the present invention will be described.

10.1 Wrist Watch Type A

First, an instance of the structure of a wrist watch-type pulse wave examination apparatus 1 according to the above embodiments will be described with reference to FIGS. 37A to 37C.

Figure 37A:
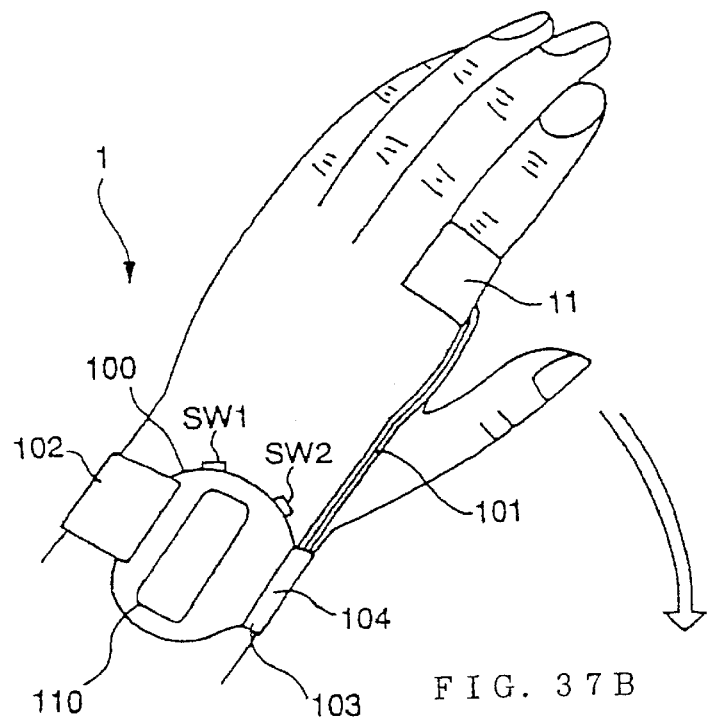
FIG. 37A is a view showing the condition of a wrist watch-type pulse wave examination apparatus which is installed.
Figure 37B:
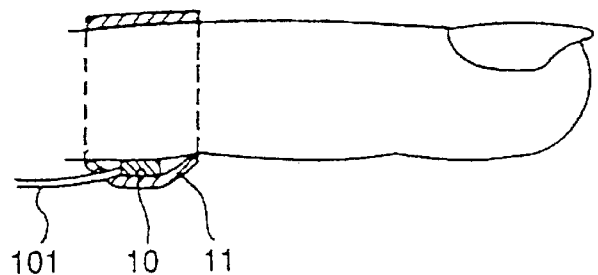
FIG. 37B is a view showing a pulse wave detecting section of a wrist watch-type pulse wave examination apparatus.

As shown in FIGS. 37A and 37B, the pulse wave examination apparatus 1 comprises mainly a device body 100 having a wrist watch structure, a cable 101 connected to the device body 100, and a pulse wave detecting section 10 arranged on the side of the end of the cable 101.

A wrist band 102 is attached to the device body 100 among these parts. Specifically, the wrist band 102 is wound around the left arm of a subject from the direction of 12 o'clock of the device body 100 and the other end is secured to a position in the direction of 6 o'clock of the device body 100.

Also, a connector section 103 is arranged at a position in the direction of 6 o'clock of the device body 100. A connector piece 104 which forms the end of the cable 101 is attached in an unrestricted manner to the connector section 103.

Figure 37C:
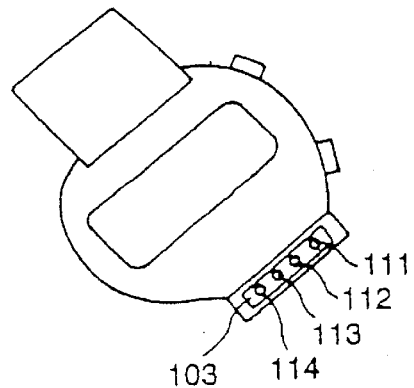
FIG. 37C is a view showing a connector section assembled in the body section of a wrist watch-type pulse wave examination apparatus.

When the connector piece 104 is removed, it is seen that the connector section 103 is provided with an LED 113 for transferring data, and a phototransistor 114, as well as contact pins 111, 112 for connection with the cable 101 as shown in FIG. 37C.

On the other hand, the pulse wave detecting section 10 is, as shown in FIG. 37B, mounted on the root of a finger so that it is shielded from light by a sensor securing band 11. When the pulse wave detecting section 10 is mounted on the root of a finger in this manner, the cable 101 can be short, hence the pulse detecting section 10 causes no obstruction even if it is mounted. Also, when the distribution of body temperature from the palm to the root of a finger is measured, the temperature of the fingertip is significantly reduced on a cold day whereas the temperature at the root of the finger is not relatively reduced as the result of a stable blood flow rate. Hence, if the pulse wave detecting section 10 is mounted on the root of a finger, a pulse waveform can be detected with accuracy even when the subject goes out on a cold day.

On the side of the surface of the device body 100, a display section 110 formed of a liquid crystal panel is arranged. The display section 110 has a segment display zone, a dot display zone and the like and displays the current time, the content of diagnosis, and the like: the display section 110 corresponds to the notifying section 80 or the display section 230 in each embodiment.

On the inside of the device body 100, an acceleration sensor, though not shown, is incorporated and detects body movement caused by the swing of an arm and the up-anddown motion of the body. The acceleration sensor corresponds to the body movement detecting section 20 in each embodiment.

Furthermore, on the inside of the device body 100, a CPU controlling various calculations and transformations is arranged (not shown) and button switches SW1 and SW2 for various manipulation and indication are disposed on the periphery of the device body 100.

10.1.1 Detailed Structure of the Pulse Wave Detecting Section

Next, the structure of the pulse wave detecting section 10 will be described with reference to FIG. 38.

Figure 38:
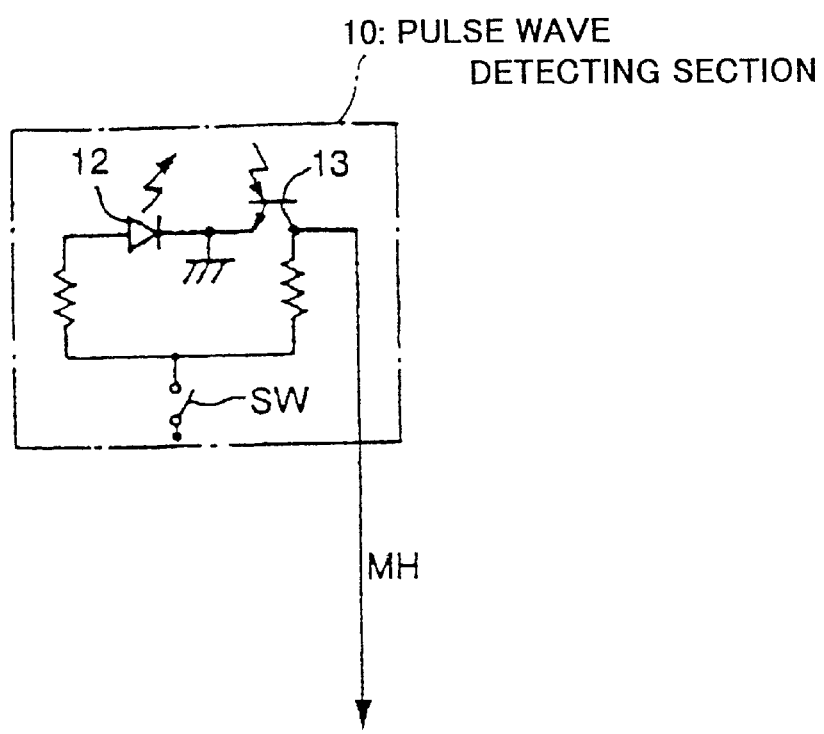
FIG. 38 is a view showing an example of the structure of a pulse wave detecting section.

As shown in FIG. 38, the pulse wave detecting section 10 comprises an LED 12, a phototransistor 13 and the like. When a switch SW is ON and power voltage is applied, light is emitted from the LED 12. The emitted light is reflected by the blood vessel and tissues of the subject and is then received by the phototransistor 13. The voltage converted from the photocurrent of the phototransistor is output as a signal MH from the pulse wave detecting section 10.

Here, as the emission wavelength of the LED 12, a wavelength in the vicinity of an absorption peak of hemoglobin contained in blood is selected. The acceptance level varies depending on the blood flow rate. A pulse waveform is therefore detected by measuring the acceptance level.

As the LED 12, an InGaN-type (indium-gallium-nitrogen-type) blue LED is preferably used. The emission spectrum of the blue LED has its emission peak, for instance, at 450 nm, and its emission wavelength zone is in a range between 350 nm and 600 nm. As the phototransistor 13 corresponding to the LED having such an emission properties, a GaAsP-type (gallium-arsenic-phosphorus-type) is used in this embodiment. As to the acceptance wavelength zone of the phototransistor 13, for instance, the major sensitive zone is in a range between 300 nm and 600 nm. The phototransistor 13 also has a sensitive zone lower than 300 nm.

A combination of such a blue LED and a phototransistor ensures that a pulse wave is detected in a wavelength zone of 300 nm to 600 nm which are the overlapped wavelengths of both with the following advantages.

First, among light included in extraneous light, the light with a wavelength of 700 nm or less tends to transmit through finger tissue with difficulty. Hence if part of a finger which is not covered with the sensor fixing band is irradiated with the extraneous light, the light cannot reach the phototransistor via the finger tissue, and only the light with a wavelength having no effect on the detection reaches the phototransistor 13. On the other hand, light with a wavelength longer than 300 nm is almost absorbed on the surface of the skin and hence a substantial acceptance wavelength zone is in a range between 300 nm and 700 nm even if the acceptance wavelength zone is less than 700 nm. Therefore, the effect of the extraneous light can be restrained even if the finger is not completely covered. Hemoglobin in blood has a large absorption coefficient for light with a wavelength ranging from 300 nm to 700 nm. This absorption coefficient is several to about 100 times larger than that for light with a wavelength of 800 nm. Therefore, when light with a wavelength (300 nm to 700 nm), at which a large absorption coefficient is obtained, is used as the light for detection according to the absorption coefficient of hemoglobin, the detected value varies with high sensitivity corresponding to variation in blood rate. This makes it possible to improve the SN ratio of the pulse waveform MH based on a variation in blood rate.

10.2 Wrist Watch-type B

Next, another instance of the structure of a wrist watch-type pulse wave examination apparatus 1 will be described with reference to FIGS. 39A and 39B. In this structure, the pulse waveform of a subject is not detected photoelectrically using an LED or a phototransistor but detected using a pressure sensor.

Figure 39A:
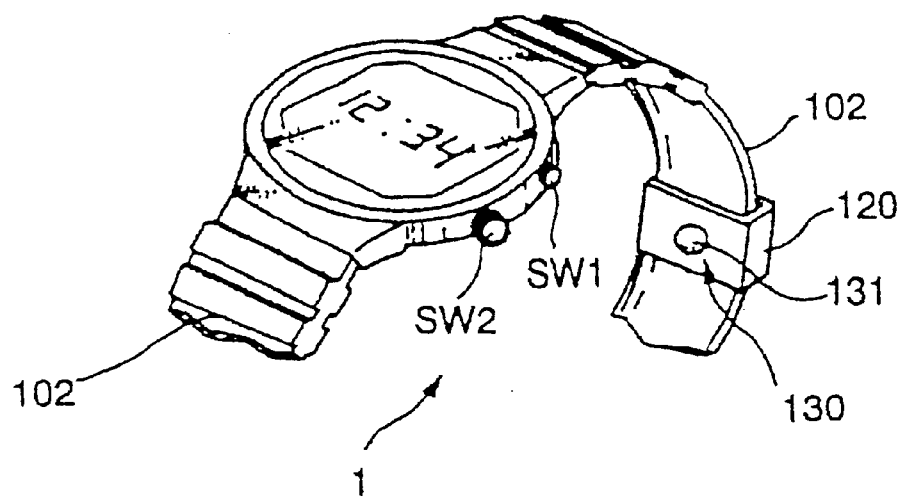
FIG. 39A is a view showing the outward appearance of a pulse wave examination apparatus when it is made into another wrist watch type.

As shown in FIG. 39A, the pulse wave examination apparatus 1 is provided with a pair of bands 102 and a projecting elastic rubber 131 of a pressure sensor 130 is formed at the fastening side of a fastener 120 of one of the bands. The band 102 provided with the fastener 120 has a structure (though its detail is not shown) in which a FPC (Flexible Printed Circuit) substrate is coated with a soft plastic so as to supply a signal detected by the pressure sensor 130.

Figure 39B:
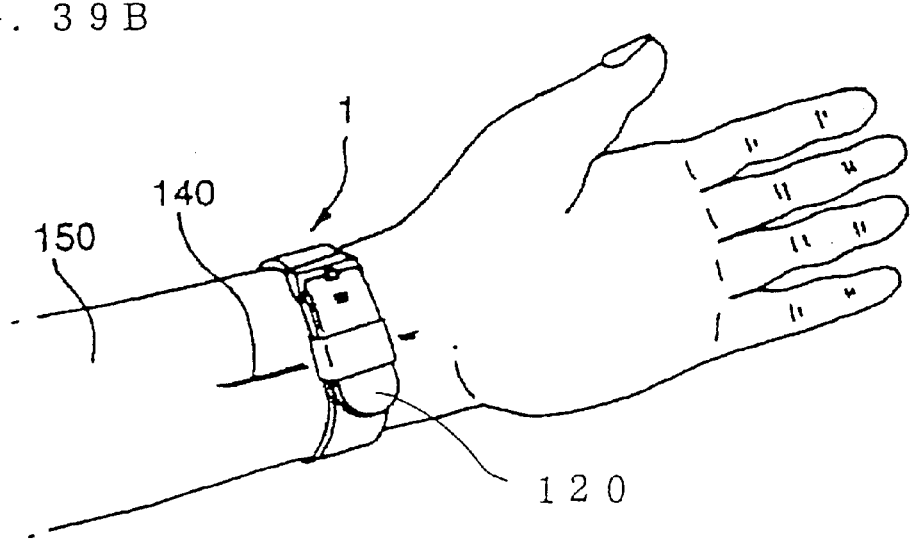
FIG. 39B is a view showing the condition of the installed pulse wave examination apparatus shown in FIG. 39A.

Upon use, as shown in FIG. 39B, the pulse wave examination apparatus 1 with a wrist watch-type structure is wound around the left arm 150 of the subject so that the elastic rubber 131 of the fastener 120 is positioned in the vicinity of a radial artery 140. It is therefore possible to detect the pulse wave constantly. Incidentally, this wound condition is no different from that in the case of using a usual wrist watch.

When the elastic rubber 131 is pushed to the vicinity of the radius artery 140 of the subject, a variation in blood flow (namely pulse wave) is transferred to the pressure sensor 130 via the elastic rubber 131 and is detected as the blood pressure by the pressure sensor 130.

In addition, to mention a further instance of the pulse wave detecting section 10, a cuff band is attached to a fingertip and the harmonic component of the pulse wave is detected while pressure is applied to the cuff band whereby the characteristics of the tidal wave and dicrotic wave may be extracted as described in Japanese Patent Application Laid-Open No. H5-192620.

10.3 Necklace-type

Figure 40:
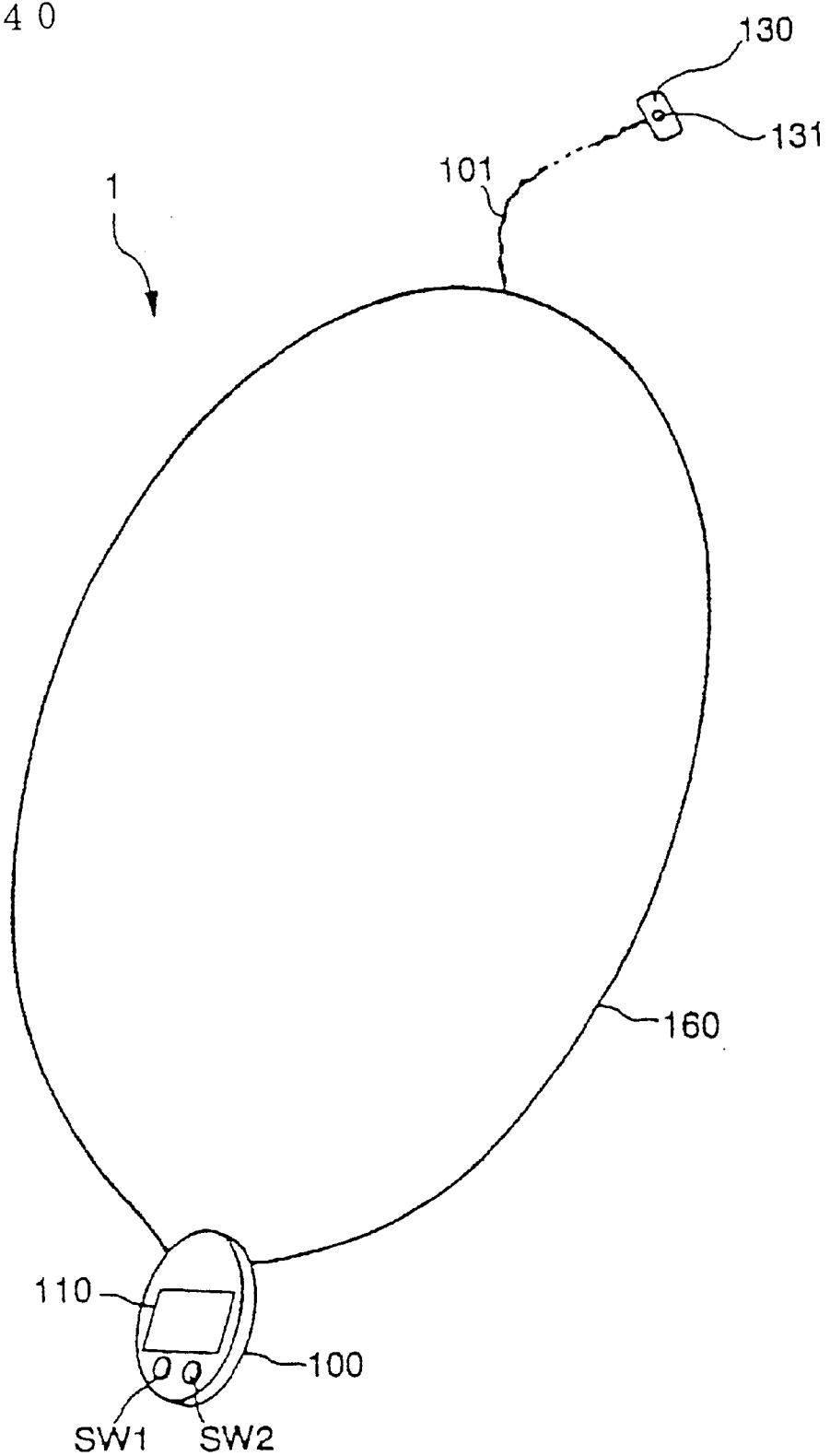
FIG. 40 is a view showing the outward appearance of the structure of the pulse wave examination apparatus when it is made into a necklace type.

It has been suggested that the pulse wave examination apparatus 1 according to each embodiment be made into a necklace-type as shown in FIG. 40.

Figure 41:
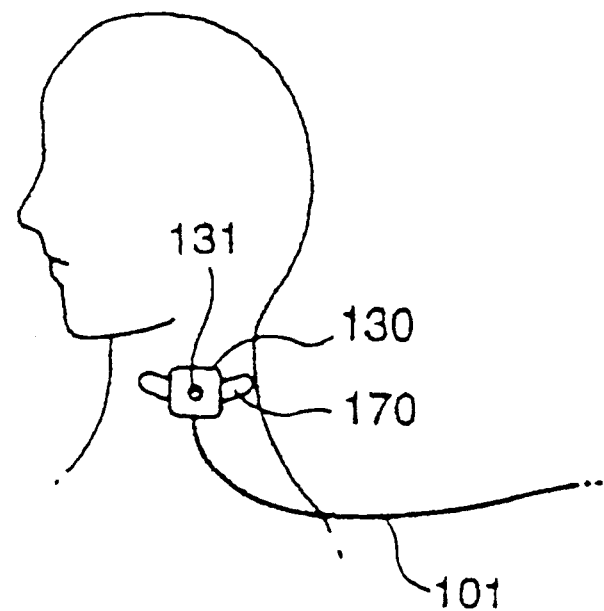
FIG. 41 is a view showing the condition in which a pulse wave detecting section of the pulse wave examination apparatus shown in FIG. 40 is attached around the carotid arteries.

In this figure, a pressure sensor 130 is arranged at the end of a cable 101 and is attached to the vicinity of the carotid artery by using an adhesive tape 170 as shown in FIG. 41. In FIG. 40, the major parts of the apparatus are incorporated into a device body 100 having a brooch-like form and a hollow portion and, on the front surface of the device body, a display section 110 and switches SW1 and SW2 are formed. The cable 101 is partially buried in a chain 160 and is used to supply a signal MH output from the pressure sensor 130 to the device body 100.

10.4 Eyeglass-type

Figure 42:
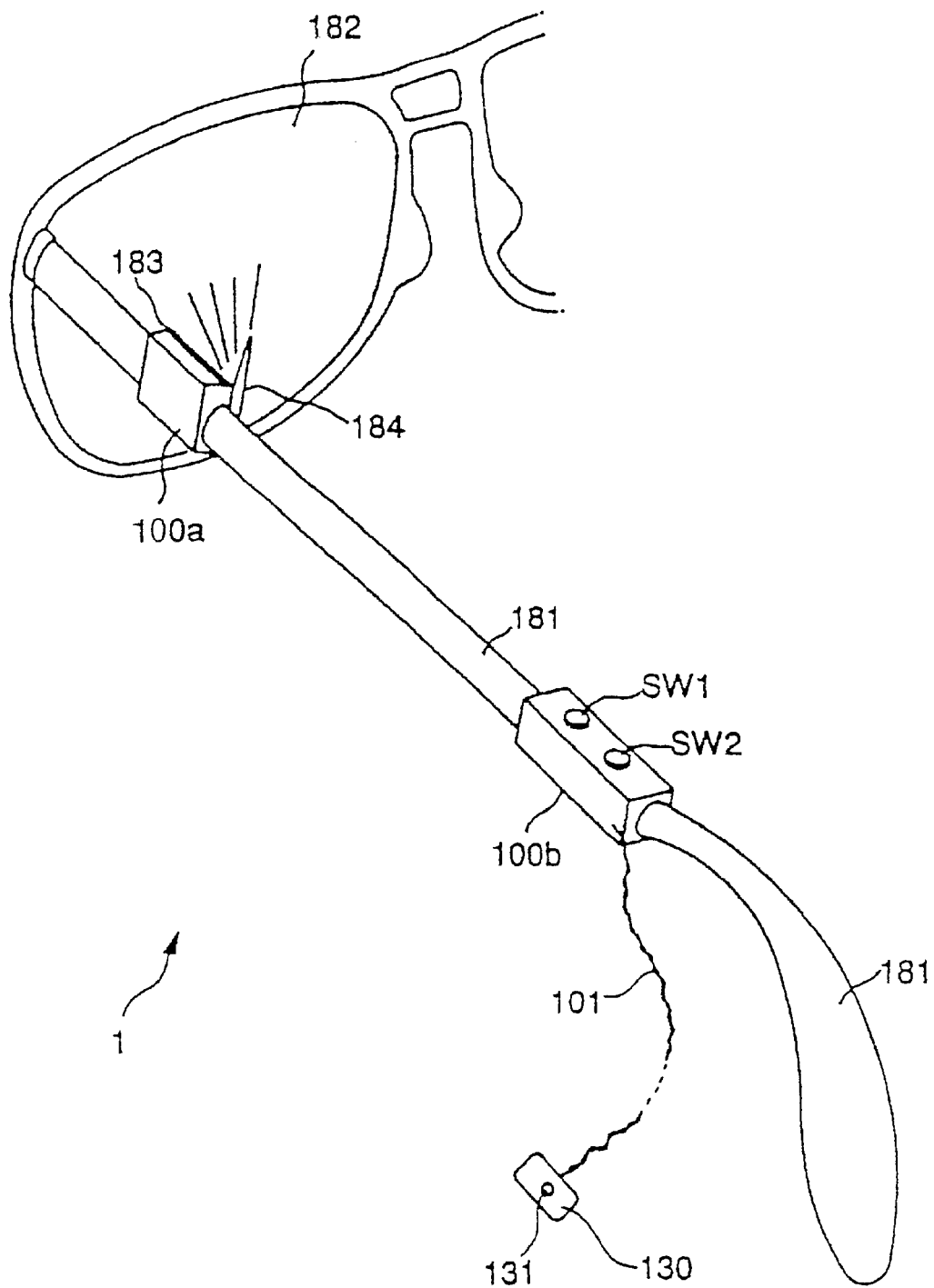
FIG. 42 is a view showing the outward appearance of the structure of a pulse wave examination apparatus when it is made into a eyeglass type.

An eyeglass-type has been considered as an embodiment of the pulse wave examination apparatus 1 according to each embodiment as shown in FIG. 42.

As shown in this figure, a device body is divided into a casing 100*a* and a casing 100*b* which are separately attached to a bow 181 of the eyeglasses. The casings 100*a* and 100*b* are electrically connected via a lead wire embedded in the bow 181. A liquid crystal panel 183 is attached to the side surface of the casing 100*a* on the side of a lens 182 and a mirror 184 is secured to one end of its side surface at a prescribed angle. The casing 100*a* includes a driving circuit for the liquid crystal panel 183 including a power source (not shown) and a circuit for providing display data which circuits constitute a display portion 110. The light emitted from the power source is reflected by the mirror 184 via the liquid crystal panel 183 and is applied to the lens 182. The major parts of the device are incorporated into the casing 100*b* and switches SW1 and SW2 are formed on the casing 100*b* as in the above embodiment.

A pressure sensor 130 is electrically connected to the casing 100b via a cable 101 and applied to the vicinity of the carotid artery as in the case of the necklace. It is noted that the lead wire connecting the casing 100a with the casing 100b may be trained along the bow 181. Also, although in this instance, the device body is divided into the casings 100a and 100b, these casings may be formed into a united casing. Moreover, the mirror 184 may be a mobile type to adjust the angle with the liquid crystal panel 183.

10.5 Card-type

Figure 43:
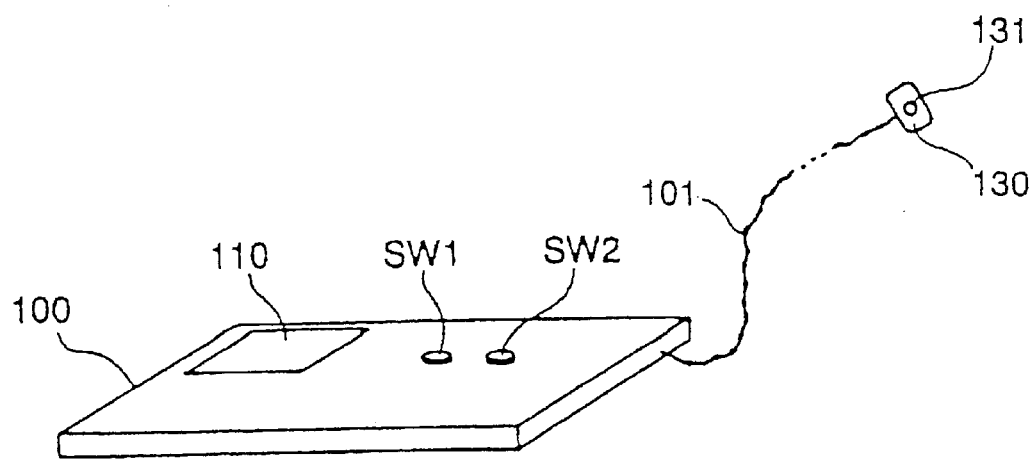
FIG. 43 is a view showing the outward appearance of the structure of a pulse wave examination apparatus when it is made into a card type.

A card-type is considered as another embodiment of the pulse wave examination apparatus 1 according to each embodiment as shown in FIG. 43. A card-type device body 100 is stored in, for instance, the left breast pocket of a subject. A pressure sensor 130 is electrically connected to the device body 100 via a cable 101 and is applied to the vicinity of the carotid artery as in the cases of the necklace and eyeglasses.

10.6 Pedometer-type

Figure 44A:
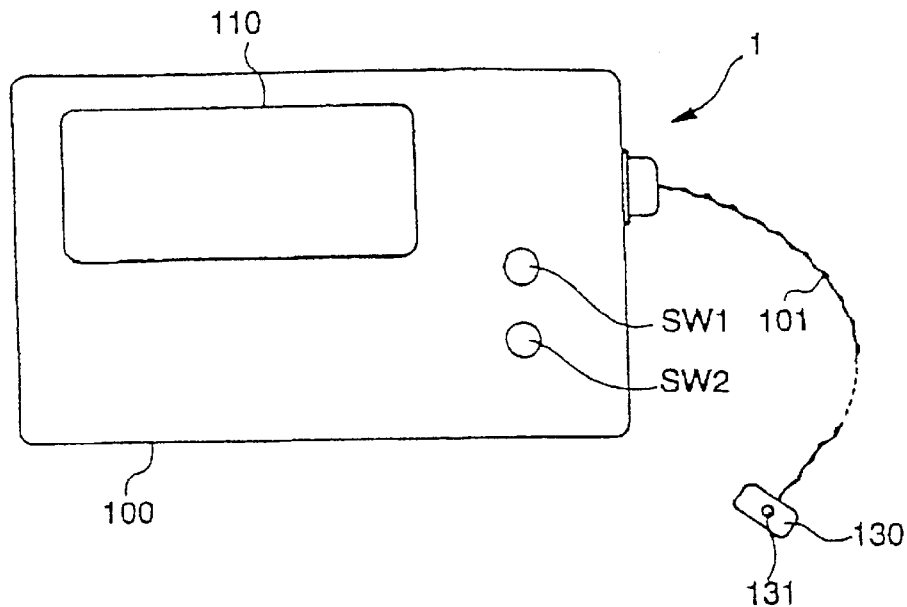
FIG. 44A is a view showing the outward appearance of the structure of a pulse wave examination apparatus when it is made into a passometer type.
Figure 44B:
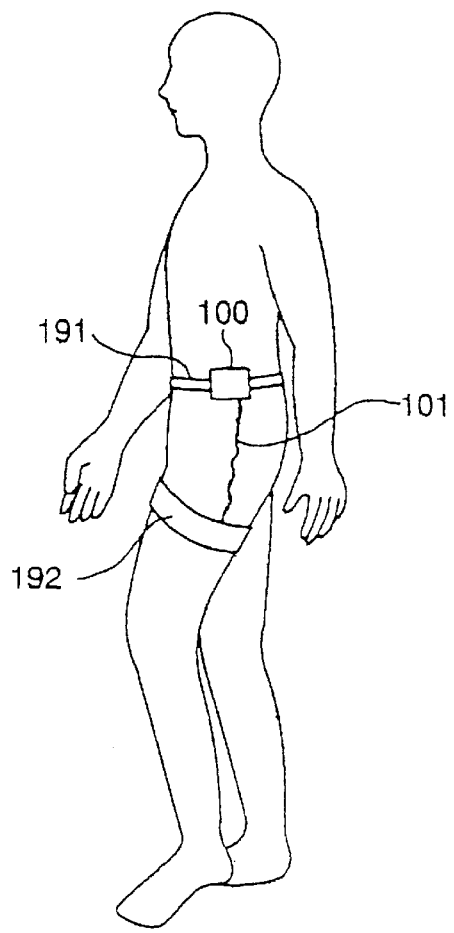
FIG. 44B is a view showing the condition of the installed pulse wave examination apparatus shown in FIG. 44A.
Figure 46:
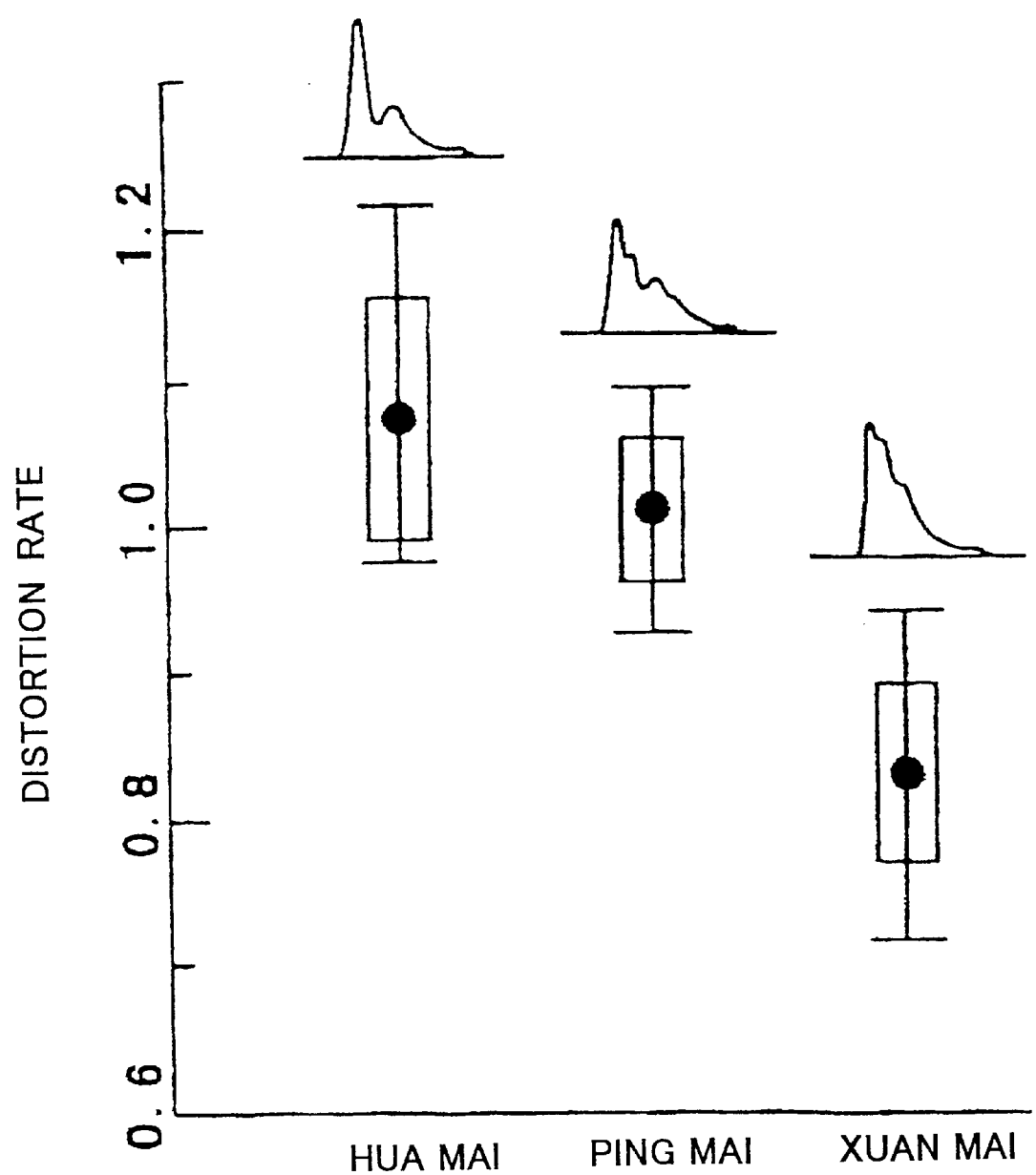
FIG. 46 is a view showing the relationship between distortion rate and the pulse waveform.

A pedometer type as shown in FIG. 44A is considered as a further embodiment of the pulse wave examination apparatus 1 according to each embodiment. As shown in FIG. 44B, a device body 100 of the pedometer type is attached to a waist belt 191. A pressure sensor 130 is electrically connected to the device body 100 via a cable 101, is applied to the vicinity of the femoral artery in the hip joint of a subject by using an adhesive tape, and is protected by a supporter 192. In this case, measures so that the cable 101 is sewed into clothes are desirably taken so that the cable 101 not be a hindrance to the daily life of the subject.

11. Tenth Embodiment 11.1 Theoretical Basis of the Tenth Embodiment

Figure 47:
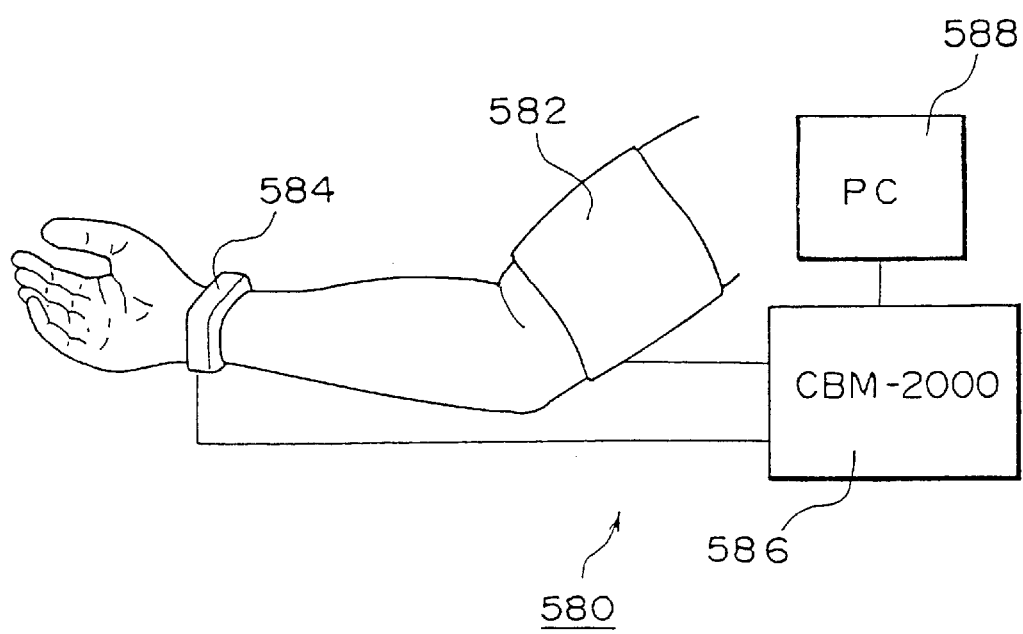
FIG. 47 is an explanatory view showing a structure used to record a waveform of arterial pressure in the arteria radialis to show a theoretical basis for a tenth embodiment.

FIG. 47 shows a structure which the inventors of the present invention use to record a waveform of arterial pressure in the radial artery. A continuous blood pressure monitor 580 (CBM-2000 manufactured by COLIN CORPORATION as shown in FIG. 47 comprises an arm band blood pressure measuring section 582, a radius artery sensor section 584, a control section 586 for controlling these sections, and a personal computer 588 connected to the control section 586.

Figure 48:
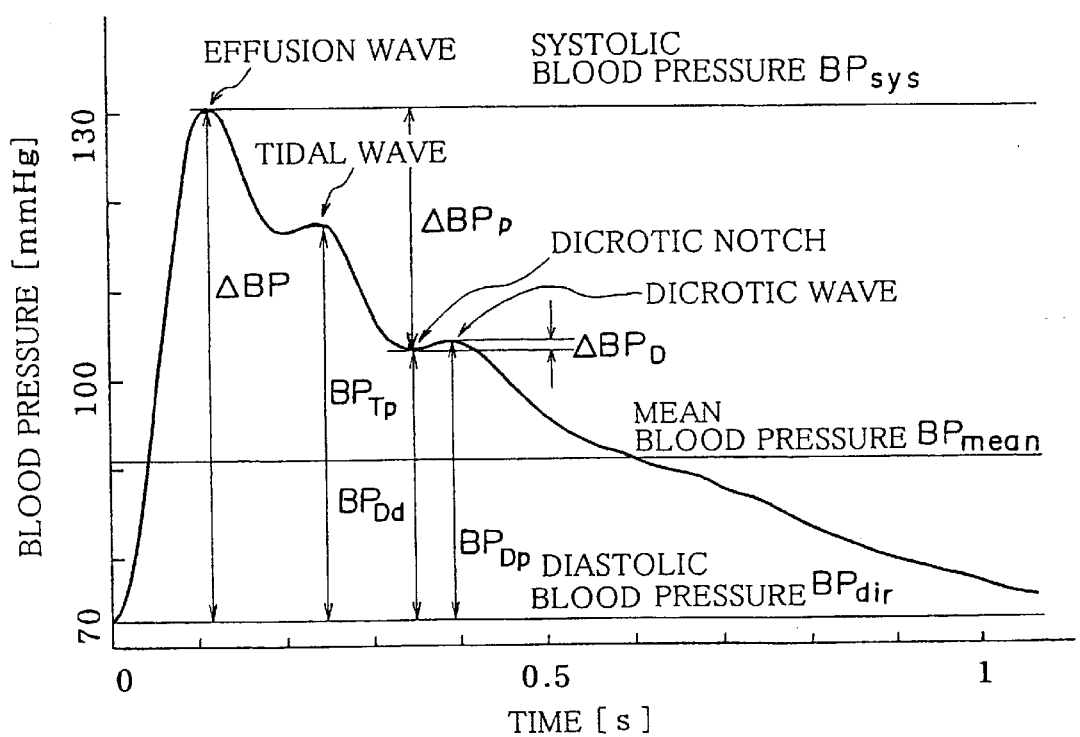
FIG. 48 is a graph showing a typical waveform of arterial pressure.

FIG. 48 is a graph showing a typical waveform of arterial pressure, namely, a waveform of blood pressure in the radial artery, which is measured by such a device as given above. The waveform of blood pressure in the artery is, as shown in FIG. 48 and as mentioned above, generally provided with an ejection wave having the highest peak, a tidal wave having the next peak and a dicrotic wave having the third peak. The peak of the ejection wave corresponds to a systolic blood pressure $BP_{sys}$. The diastolic blood pressure $BP_{dir}$ corresponds to the lowest blood pressure in the blood pressure waveform. A pressure difference between the systolic blood pressure $BP_{sys}$ and the diastolic blood pressure $BP_{dir}$ is called a pulse pressure $\Delta BP$. The mean blood pressure $BP_{mean}$ is obtained by integrating the waveform of blood pressure and calculating the time average of the resulting value.

In the continuous blood pressure monitor 580 shown in FIG. 47, the arm band blood pressure measuring section 582 is used to measure the systolic blood pressure $BP_{sys}$ and the diastolic blood pressure $BP_{dir}$. The radial artery sensor section 584 detects a pulse waveform corresponding to the waveform of blood pressure in the radial artery. This pulse waveform is calibrated by the systolic blood pressure $BP_{sys}$ and the diastolic blood pressure $BP_{dir}$ which are measured by the arm band blood pressure measuring section 582 to obtain a waveform of arterial pressure.

Using the continuous blood pressure monitor 580, the inventors of the present invention measured the waveform of the blood pressure in each radial artery of 74 healthy adults between the ages of 22 and 46 years at a time when they were hungry (09:30–13:30) in a condition where they were seated after resting for 15 minutes.

Figure 49:
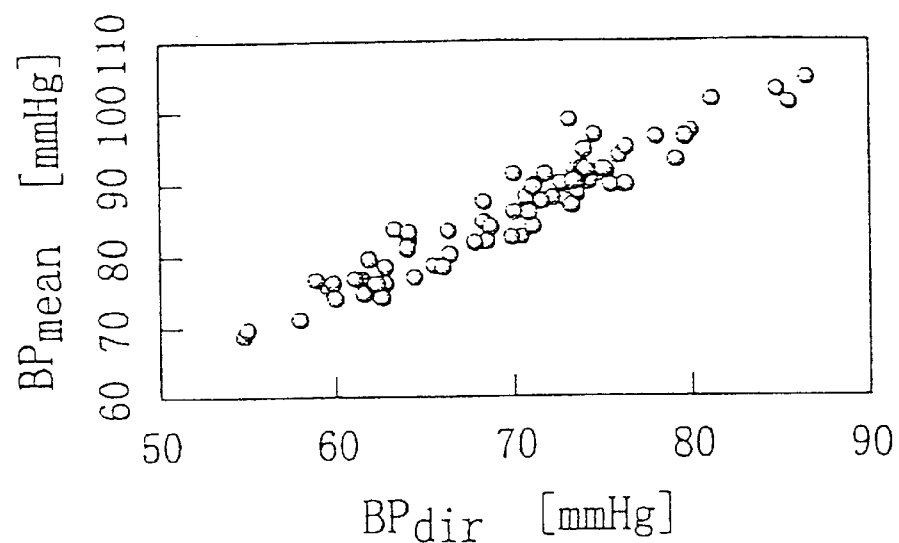
FIG. 49 is a graph of experimental results obtained using the structure shown in FIG. 47, showing the relationship between the mean blood pressure and diastolic blood pressure.
Figure 50:
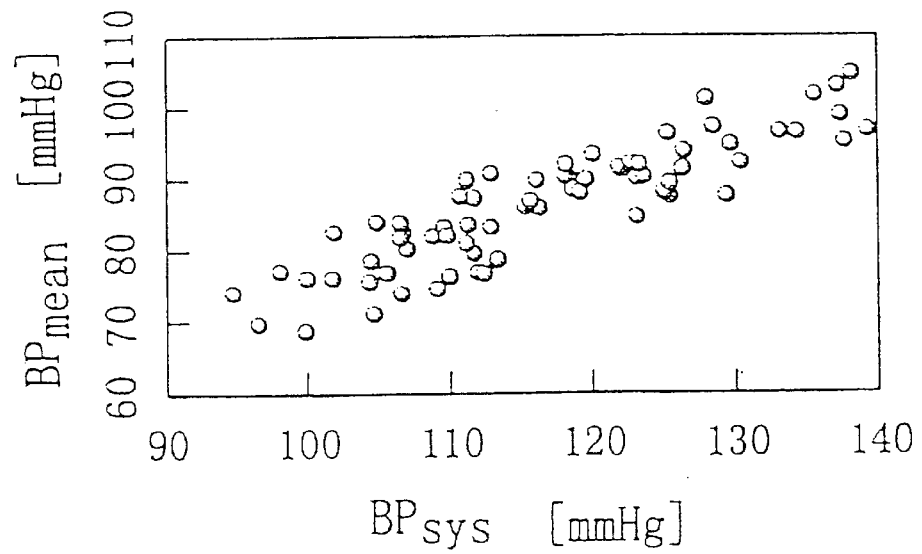
FIG. 50 is a graph of experimental results obtained using the structure shown in FIG. 47, showing the relationship between the mean blood pressure and systolic blood pressure.
Figure 51:
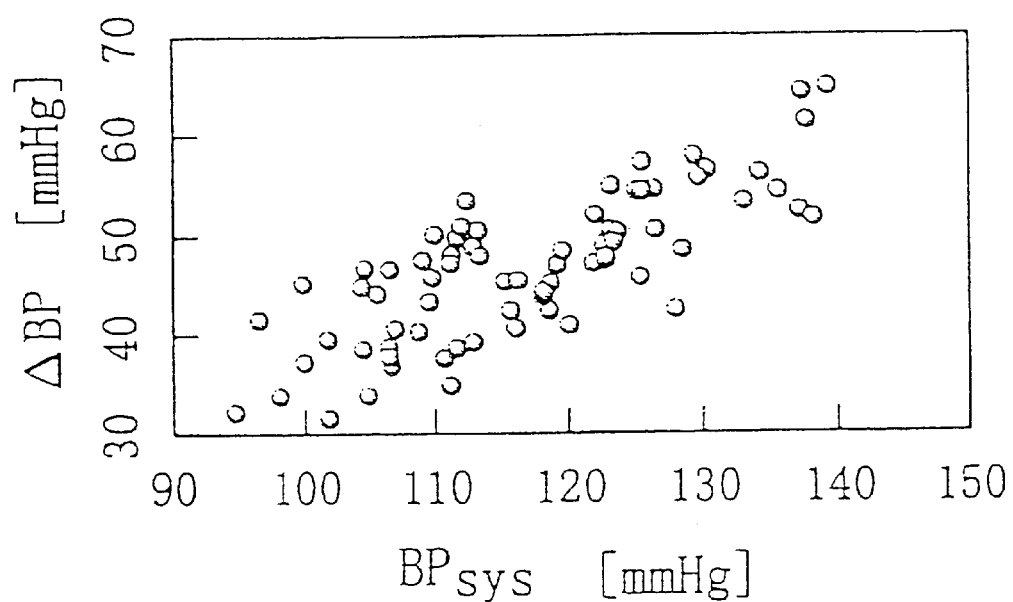
FIG. 51 is a graph of experimental results obtained using the structure shown in FIG. 47, showing the relationship between pulse pressure and systolic blood pressure.

FIGS. 49 to 51 are graphs showing the results plotted for data obtained by such a measurement. FIG. 49 shows that there is a strong linear relationship between the mean blood pressure $BP_{mean}$ and the diastolic blood pressure $BP_{dir}$, having a strong correlation with a correlation coefficient r of 0.95. FIG. 50 shows that there is also a strong linear relationship between the mean blood pressure $BP_{mean}$ and the systolic blood pressure $BP_{sys}$ (correlation coefficient r=0.87). Furthermore, FIG. 51 shows that there is also a strong linear relationship between the pulse pressure $\Delta BP$, which is the pressure difference between the systolic blood pressure $BP_{sys}$ and the diastolic blood pressure $BP_{dir}$, and the systolic blood pressure $BP_{sys}$ (correlation coefficient r=0.76). It is therefore understood that the blood pressure can be expressed by the mean blood pressure $BP_{mean}$ or the pulse pressure $\Delta BP$.

11.2 Structure of the Blood Pressure Monitor

Figure 52:
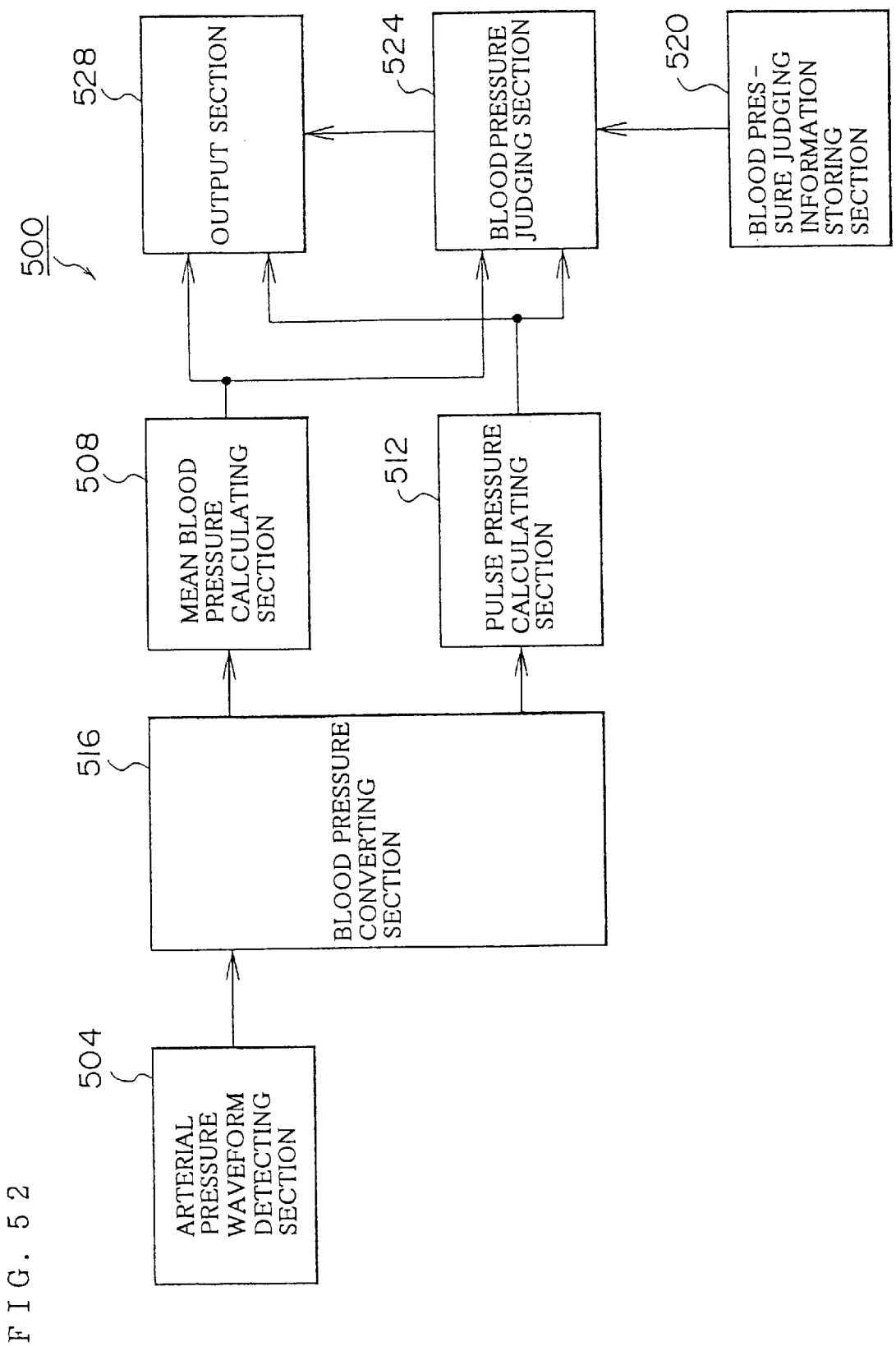
FIG. 52 is a block diagram showing a blood pressure monitor of a tenth embodiment.

FIG. 52 is a block diagram showing the structure of a blood pressure monitor 500 of this embodiment. As shown in this figure, the blood pressure monitor 500 comprises an arterial pressure waveform detecting section 504, a blood pressure converting section 516, a mean blood pressure calculating section 508, a pulse pressure calculating section 512, a blood pressure-judging information storing section 520, a blood pressure judging section 524, and an output section 528.

The arterial pressure waveform detecting section 504 measures blood pressure in an artery continuously to detect a waveform of arterial pressure. The arterial pressure waveform detecting section 504 may be formed including, for instance, a radial arterial sensor section 584 shown in FIG. 47, a pulse wave detecting section 10 shown in FIG. 37B and a pressure sensor 130 shown in FIGS. 39A, 40, 41, 42, 43 and 44A.

The blood pressure converting section 516 converts the waveform of arterial pressure, detected by the arterial pressure waveform detecting section 504, into the waveform of cardiac-position arterial pressure at a position corresponding to the height of the heart. For instance, the blood pressure converting section 516 comprises calibrating the waveform of arterial pressure, detected by the arterial pressure waveform detecting section 504, by using a maximum blood pressure and minimum blood pressure which are detected by an arm band blood pressure gauge.

The mean blood pressure calculating section 508 calculates the mean blood pressure $BP_{mean}$ based on the waveform of arterial pressure or the waveform of cardiac-position arterial pressure.

The pulse pressure calculating section 512 calculates the pulse pressure $\Delta BP$ which is the pressure difference between a maximum pressure (the systolic blood pressure $BP_{sys}$) and a minimum pressure (the diastolic blood pressure $BP_{dir}$) on the basis of the waveform of arterial pressure.

The blood pressure-judging information storing section 520 stores blood pressure-judging information in advance. This blood pressure-judging information includes, for instance, a threshold value of blood pressure, in terms of the mean blood pressure and the pulse pressure, which is a boundary blood pressure between hypertension and normal, and a threshold value of blood pressure which is a boundary blood pressure between hypotension and normal blood pressure. It is needless to say that the mean blood pressure and the pulse pressure have high correlations with systolic blood pressure $BP_{sys}$ (maximum blood pressure) and the diastolic blood pressure $BP_{dir}$ (minimum blood pressure) and can become indexes showing the condition of blood pressure as aforementioned with reference to FIGS. 49–51.

The blood pressure judging section 524 judges the blood pressure on the basis of at least one of the mean blood pressure $BP_{mean}$ and the pulse pressure ΔBP and the blood pressure-judging information stored in the blood pressure-judging information storing section 520. For instance, a judgment as to whether it is hypertension, hypotension, or normal is made based on at least one of the resulting mean blood pressure $BP_{mean}$ and pulse pressure ΔBP and the blood pressure judging information.

The output section 528 outputs at least one piece of information corresponding to the mean blood pressure $BP_{mean}$, the pulse pressure ΔBP and the judgment of the blood pressure. The output section 528 outputs at least one piece of information corresponding to the mean blood pressure, information corresponding to the pulse pressure, and information corresponding to the judgment of the blood pressure either to a liquid crystal display, a CRT, a printer, or the like in the form of, for instance, numerals and graphs or as voltages or digital information corresponding to each piece of information.

11.3 Action of the Blood Pressure Monitor

The action of the blood pressure monitor 500 of this embodiment will be described with reference to FIG. 52.

First, the arterial pressure waveform detecting section 504 measures blood pressure in the artery continuously by using the aforementioned pressure sensor 130 or the like to detect a waveform of arterial pressure.

The waveform of arterial pressure which is detected by the arterial pressure waveform detecting section 504 is converted by the blood pressure converting section 516 into the waveform of cardiac-position arterial pressure which is a waveform of arterial pressure at a position corresponding to the height of the heart.

Next, the mean blood pressure calculating section 508 calculates the mean blood pressure $BP_{mean}$ on the basis of the waveform of arterial pressure or the waveform of the cardiac-position arterial pressure which are output from the arterial pressure waveform detecting section 504 or the blood pressure converting section 516.

At the same time, the pulse pressure calculating section 512 calculates the pulse pressure ΔBP, which is the pressure difference between a maximum blood pressure (systolic blood pressure $BP_{sys}$) and a minimum pressure (diastolic blood pressure $BP_{dir}$), on the basis of the waveform of arterial pressure or the waveform of the cardiac-position arterial pressure which are output from the arterial pressure waveform detecting section 504 or the blood pressure converting section 516.

Then, at least one of the mean blood pressure $BP_{mean}$ and the pulse pressure ΔBP is input into the blood pressure judging section 524. The blood pressure judging section 524 determines whether it is, for instance, hypertension, hypotension, or normal on the basis of the input data and the blood pressure-judging information stored in the blood pressure-judging information storing section 520.

The output section 528 outputs at least one piece of information corresponding to the mean blood pressure $BP_{mean}$, information corresponding to the pulse pressure ΔBP and information corresponding to the judgment of the blood pressure. The output section is provided with, for example, a liquid crystal display, a CRT, a printer, or the like and may output each piece of information in the form of, for instance, numerals and graphs or as voltages or digital information corresponding to each piece of information.

In this manner, the blood pressure monitor 500 of this embodiment can calculate and monitor the mean blood pressure and the pulse pressure on the basis of the waveform of arterial pressure detected by the arterial pressure waveform detecting section 504. The blood pressure monitor 500 can also make a determination as to whether it is hypertension, hypotension, or normal on the basis of at least either one of the resulting mean blood pressure $BP_{mean}$ and the pulse pressure ΔBP, and the blood pressure-judging information stored in advance.

12. Eleventh Embodiment 12.1 Theoretical Basis of the Eleventh Embodiment

The inventors of the present invention further carried out the following experiment by using the data obtained in the experiment described in the section "Theoretical basis of the tenth embodiment".

In detail, the resulting waveforms of radial arterial pressure were classified into those of a Ping mai, Hua mai and Xuan mai whose typical waveforms of arterial pressure are shown in FIGS. 45A, 45B and 45C with reference to the form model of waveforms in Chinese medicine (Kobe Research Institute of Chinese Medicine: Glossoscopy and Sphygmopalpation in Chinese Medicine Diagnosis, Fei Zhaofu (chief editor), Chinese pulse diagnosis research, Shanghai Chinese medical college publishing house (1991)).

Figure 53:
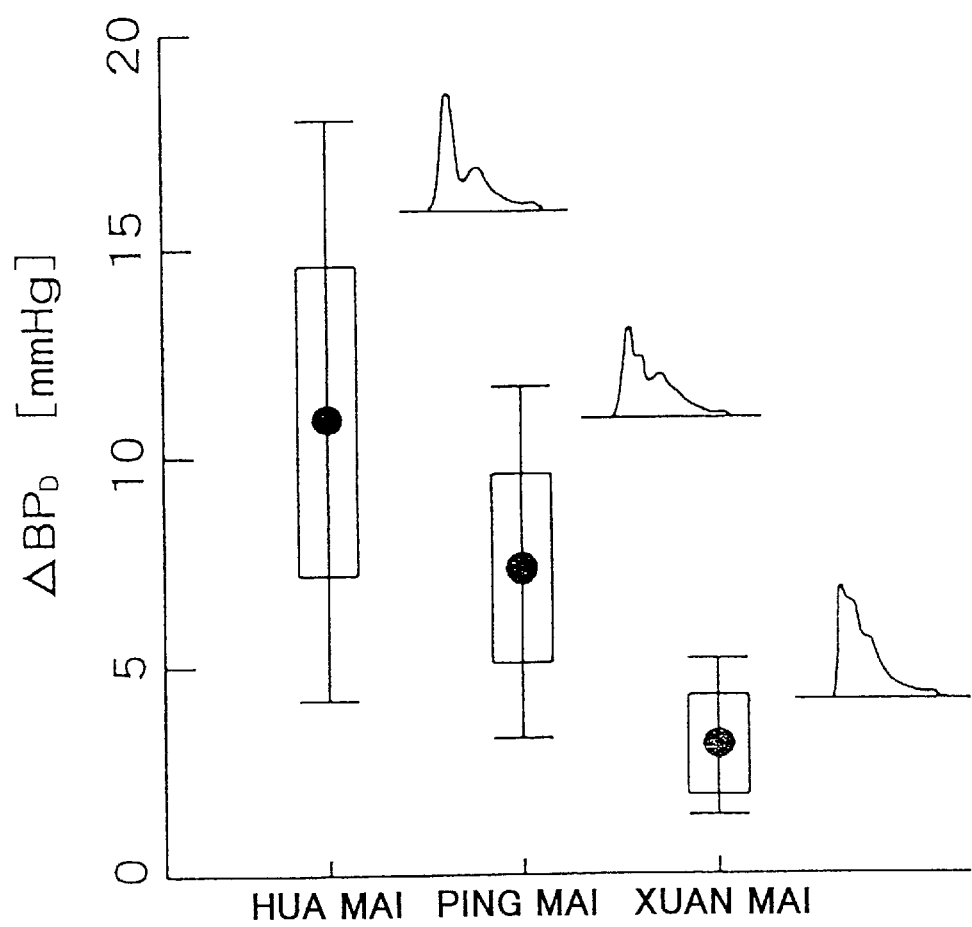
FIG. 53 is a graph showing the distribution of the dicrotic wave height $\Delta BP_D$ for each pulse waveform to show a theoretical basis for an eleventh embodiment.

As a result, it was confirmed that, as shown in FIG. 53, a Hua mai, Ping mai and Xuan mai could be classified significantly by the dicrotic wave height $\Delta BP_D$ (see FIG. 48) which is a difference in blood pressure between the dicrotic notch and a peak of a dicrotic wave. Specifically, the $\Delta BP_D$ of a Hua mai was 11±4 mmHg, the ΔBPD of a Ping mai was 7±2 mmHg and the $\Delta BP_D$ of a Xuan mai was 3±1 mmHg, showing a significant difference between the three groups with a significance level of 1%.

Figure 54:
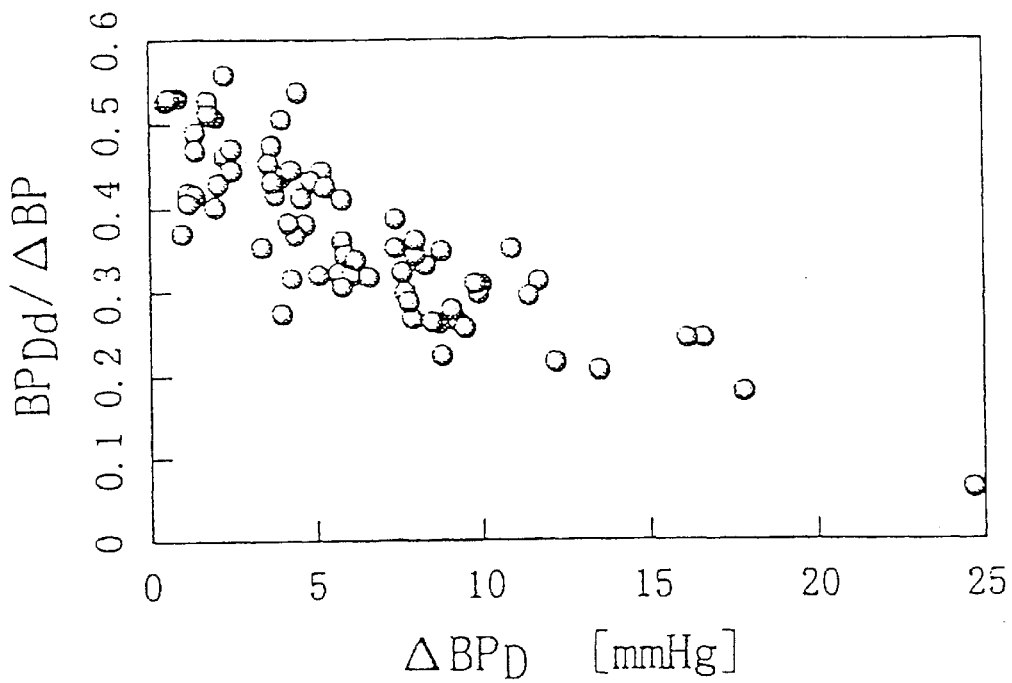
FIG. 54 is a graph showing the relationship between a dicrotic pressure difference ratio $BP_{Dd}/\Delta BP$ and a dicrotic wave height $\Delta BP_D$ to show a theoretical basis for the eleventh embodiment.

FIG. 54 shows that there is a linear relationship between the dicrotic pressure difference ratio $BP_{Dd}/\Delta BP$ and the dicrotic wave height $\Delta BP_D$, the ratio $BP_{Dd}/\Delta BP$ being the ratio of the dicrotic pressure difference $BP_{Dd}$ (see FIG. 48), which is the pressure difference between the blood pressure at a dicrotic notch and the minimum blood pressure, to the pulse pressure ΔBP which is the pressure difference between the maximum blood pressure and the minimum blood pressure. The correlation coefficient between the two is −0.86, which indicates a strong correlation. Therefore, it is understood that the dicrotic pressure difference ratio $BP_{Dd}/\Delta BP$ may be used as an index for the significant classifying of a Hua mai, Ping mai and Xuan mai which are the typical pulse waveforms in sphygmopalpation used in Chinese medicine.

Figure 55:
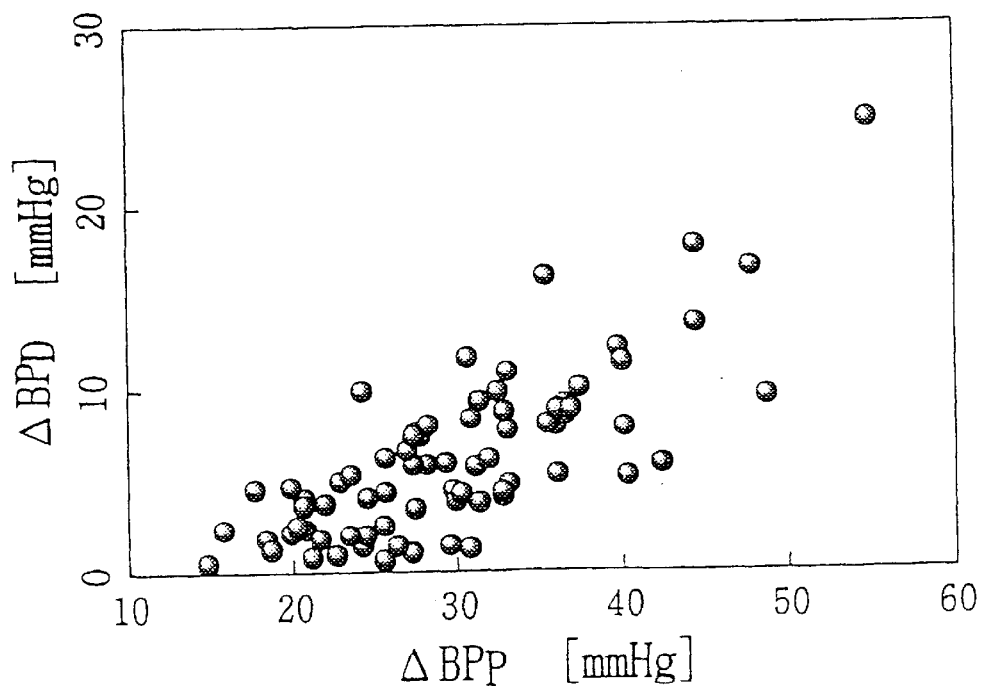
FIG. 55 is a graph showing the relationship between an ejection diastolic pressure $\Delta BP_P$ and a dicrotic wave height $\Delta BP_D$ to show a theoretical basis for the eleventh embodiment.

FIG. 55 shows that there is a linear relationship between the effusion diastolic pressure $\Delta BP_P$, which is the pressure difference between the blood pressure at a dicrotic notch and the maximum blood pressure, and the dicrotic wave height $\Delta BP_D$. The correlation coefficient between them is 0.77 showing a strong correlation. The effusion diastolic pressure $\Delta BP_P$ may also be used as an index for the significant classifying of a Hua mai, Ping mai and Xuan mai which are the typical pulse waveforms in sphygmopalpation used in Chinese medicine.

Moreover, as is clear from FIGS. 45A, 45B and 45C which show typical waveforms of arterial pressure in pulse waveforms classified into a Ping mai, Hua mai and Xuan mai detected by sphygmopalpation used in Chinese medicine, the ratio of the mean blood pressure $B_{mean}$ to the pulse pressure ΔBP, namely the mean blood pressure-pulse pressure ratio $BP_{mean}/\Delta BP$ increases in the order of a Hua mai, Ping mai and Xuan mai. It is therefore possible to classify pulse waveforms, namely a Hua mai, Ping mai and Xuan mai by the mean blood pressure-pulse pressure ratio $BP_{mean}/\Delta BP$.

12.2 Structure of Pulse Waveform Monitor

Figure 56:
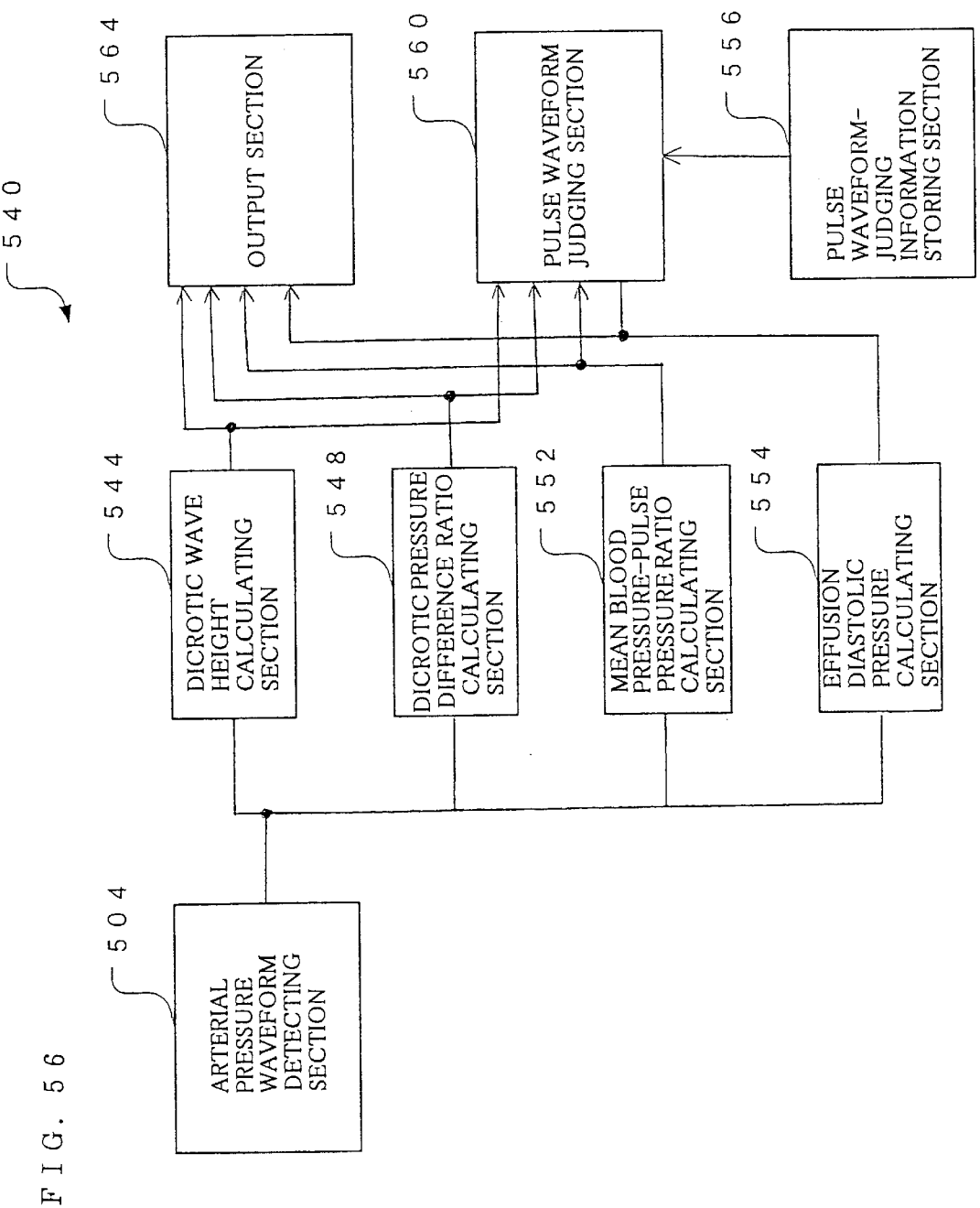
FIG. 56 is a block diagram showing the structure of a pulse waveform monitor of the eleventh embodiment.

FIG. 56 is a block diagram showing the structure of a pulse waveform monitor 540 of this embodiment. As shown in FIG. 56, the pulse waveform monitor 540 comprises an arterial pressure waveform detecting section 504, a dicrotic wave height calculating section 544, a dicrotic pressure difference ratio calculating section 548, a mean blood pressure-pulse pressure ratio calculating section 552, an effusion diastolic pressure calculating section 554, a pulse waveform-judging information storing section 556, a pulse waveform judging section 560 and an output section 564. It is noted that, though not shown in FIG. 56, a blood pressure converting section may be arranged subsequent to the arterial pressure waveform detecting section 504 and preceding the dicrotic wave height calculating section 544, the dicrotic pressure difference ratio calculating section 548 and the mean blood pressure-pulse pressure ratio calculating section 552.

The arterial pressure waveform detecting section 504 measures the blood pressure in the artery continuously to detect a waveform of arterial pressure. The arterial pressure waveform detecting section 504 may be formed comprising a radial artery sensor section 584 as shown in FIG. 47, a pulse wave detecting section 10 as shown in FIG. 37B, and a pressure sensor 130 as shown in FIGS. 39A, 40, 41, 42, 43 and 44A.

The blood pressure converting section converts the waveform of arterial pressure, detected by the arterial pressure waveform detecting section, into the waveform of cardinal-position arterial pressure at a height corresponding to that of the heart.

The dicrotic wave height calculating section 544 calculates the dicrotic wave height $\Delta BP_D$ (see FIG. 48) which is the difference in blood pressure between the dicrotic notch and the peak of a dicrotic wave based on the waveform of arterial pressure or the waveform of cardinal-position arterial pressure.

The dicrotic pressure difference ratio calculating section 548 calculates the dicrotic pressure difference ratio $BP_{Dd}/\Delta BP$ which is the ratio of the dicrotic pressure difference $BP_{Dd}$, which is the pressure difference between the blood pressure at a dicrotic notch and the minimum blood pressure (the diastolic blood pressure $BP_{dir}$), to the pulse pressure $\Delta BP$ which is the pressure difference between the maximum blood pressure and the minimum blood pressure, based on the waveform of arterial pressure or the waveform of cardinal-position arterial pressure.

The mean blood pressure-pulse pressure ratio calculating section 552 calculates the mean blood pressure-pulse pressure ratio $BP_{mean}/\Delta BP$ which is the ratio of the mean blood pressure $BP_{mean}$ to the pulse pressure $\Delta BP$, which is the pressure difference between the maximum blood pressure and the minimum blood pressure, based on the waveform of arterial pressure or the waveform of cardinal-position arterial pressure.

The effusion diastolic pressure $\Delta BP_P$ calculating section 554 calculates the effusion diastolic pressure $\Delta BP_P$ (see FIG. 48) which is the difference between the blood pressure at a dicrotic notch and systolic blood pressure $BP_{sys}$ which are obtained from the pulse wave of arterial pressure or the waveform of cardinal-position arterial pressure.

The pulse waveform-judging information storing section 556 stores pulse waveform-judging information in advance. The pulse waveform-judging information includes, for instance, threshold values for the dicrotic wave height $\Delta BP_D$, the dicrotic pressure difference ratio $BP_{Dd}/\Delta BP$, the mean blood pressure-pulse pressure ratio $BP_{mean}/\Delta BP$, or the effusion diastolic pressure $\Delta BP_P$ to classify pulse waveforms, for instance, a Hua mai, Ping mai, and Xuanmai, which are the typical pulse waveforms in sphygmopalpation used in Chinese medicine, from one another. These pulse waveforms can be sorted by the dicrotic wave height $\Delta BP_D$, the dicrotic pressure difference ratio $BP_{Dd}/\Delta BP$, the mean blood pressure-pulse pressure ratio $BP_{mean}/\Delta BP$, or the effusion diastolic pressure $\Delta BP_P$ as aforementioned with reference to FIGS. 53, 54, 45A, 45B, 45C and 55.

The pulse waveform judging section 560 judges the pulse waveform on the basis of the pulse waveform-judging information and at least one of the dicrotic wave height $\Delta BP_D$, the dicrotic pressure difference ratio $BP_{Dd}/\Delta BP$, the mean blood pressure-pulse pressure ratio $BP_{mean}/\Delta BP$, and the effusion diastolic pressure $\Delta BP_P$. It is therefore possible to judge, for instance, a Hua mai, Ping mai, and Xuan mai showing pulse waveforms in sphygmopalpation used in Chinese medicine by the pulse waveform-judging information stored in advance, and at least one of the dicrotic wave height $\Delta BP_D$, the dicrotic pressure difference ratio $BP_{Dd}/\Delta BP$, the mean blood pressure-pulse pressure ratio $BP_{mean}/\Delta BP$, and the effusion diastolic pressure $\Delta BP_P$.

The output section 564 outputs at least one piece of information corresponding to the dicrotic wave height $\Delta BP_D$, the dicrotic pressure difference ratio $BP_{Dd}/\Delta BP$, the mean blood pressure-pulse pressure ratio $BP_{mean}/\Delta BP$, the effusion diastolic pressure $\Delta BP_P$ and the pulse waveform-judged information. This information may be output either to a liquid crystal display, a CRT or a printer in the form of numerals or graphs, or as voltage or digital information corresponding to the information.

12.3 Action of Pulse Waveform Monitor

The action of the pulse waveform monitor 540 of this embodiment will be described with reference to FIG. 56.

First, the arterial pressure waveform detecting section 504 measures blood pressure in the artery continuously by the aforementioned pressure sensor 130 or the like to detect a waveform of arterial pressure.

Then, the blood pressure converting section converts the waveform of arterial pressure detected by the arterial pressure waveform detecting section 504 into the waveform of cardinal-position arterial pressure at a position corresponding to the height of the heart. It is noted that this step may be omitted in the case where the waveform of arterial pressure is used in the succeeding steps.

Next, the dicrotic wave height calculating section 544 calculates the dicrotic wave height $\Delta BP_D$ (FIG. 48), which is the difference in blood pressure between the dicrotic notch and the peak of a dicrotic wave, based on the waveform of arterial pressure or the waveform of the cardinal-position arterial pressure.

In parallel with the calculations of the dicrotic wave height $\Delta BP_D$ the dicrotic pressure difference ratio calculating section 548 calculates the dicrotic pressure difference ratio $BP_{Dd}/\Delta BP$ which is the ratio of the dicrotic pressure difference $BP_{Dd}$, which is the pressure difference between the blood pressure at a dicrotic notch and the minimum blood pressure (the diastolic blood pressure $BP_{dir}$), to the pulse pressure $\Delta BP$ which is a pressure difference between a maximum blood pressure and a minimum blood pressure, based on the waveform of arterial pressure or the waveform of cardinal-position arterial pressure.

At the same time, the mean blood pressure-pulse pressure ratio calculating section 552 calculates the mean blood pressure-pulse pressure ratio $BP_{mean}/\Delta BP$ which is the ratio of the mean blood pressure $BP_{mean}$ to the pulse pressure $\Delta BP$, which is the pressure difference between the maximum blood pressure and the minimum blood pressure, based on the waveform of arterial pressure or the waveform of cardinal-position arterial pressure.

Also, in parallel with the above calculations, the effusion diastolic pressure calculating section 554 calculates the effusion diastolic pressure $\Delta BP_P$ (see FIG. 48) which is the difference between the blood pressure at a dicrotic notch and the systolic blood pressure $BP_{sys}$ which are obtained from the pulse wave of arterial pressure or the waveform of cardinal-position arterial pressure.

Next, the pulse waveform judging section 560 judges the pulse waveform such as a Hua mai, Ping mai and Xuan mai showing pulse waveforms in sphygmopalpation used in Chinese medicine on the basis of the pulse waveform-judging information and at least one of the dicrotic wave height $\Delta BP_D$, the dicrotic pressure difference ratio $BP_{Dd}/\Delta BP$, the mean blood pressure-pulse pressure ratio $BP_{mean}/\Delta BP$, and the effusion diastolic pressure $\Delta BP_P$.

The output section 564 outputs at least one piece of information corresponding to the dicrotic wave height $\Delta BP_D$, the dicrotic pressure difference ratio $BP_{Dd}/\Delta BP$, the mean blood pressure-pulse pressure ratio $BP_{mean}\Delta BP$, the effusion diastolic pressure $\Delta BP_P$ and the pulse waveform-judged information. This information may be output either to a liquid crystal display, a CRT or a printer in the form of numerals or graphs, or as voltage or digital information corresponding to the information.

In this manner, according to the pulse waveform monitor 540 of this embodiment, at least one of the dicrotic wave height $\Delta BP_D$, the dicrotic pressure difference ratio $BP_{Dd}/\Delta BP$, the mean blood pressure-pulse pressure ratio $BP_{mean}/\Delta BP$, and the effusion diastolic pressure$\Delta BP_P$ can be calculated based on the waveform of arterial pressure detected by the pulse waveform detecting section 504. The pulse waveform monitor 540 can also judge the pulse waveform on the basis of at least one of the dicrotic wave height$\Delta BP_D$, the dicrotic pressure difference ratio $BP_{Dd}/\Delta BP$, the mean blood pressure-pulse pressure ratio $BP_{mean}/\Delta BP$, and the effusion diastolic pressure$\Delta BP$p and on the pulse waveform-judging information. The pulse waveform monitor 540 can further output one piece of information corresponding to the dicrotic wave height $\Delta BP_D$, the dicrotic pressure difference ratio $BP_{Dd}/\Delta BP$, the mean blood pressure-pulse pressure ratio $BP_{mean}/\Delta BP$, the effusion diastolic pressure$\Delta BP_P$ and information relating to the pulse waveform in the form of, for example, numerals, graphs or voltages.

13. Twelfth Embodiment 13.1 Principle

The inventors of the present invention monitored the aforementioned effusion diastolic pressure $\Delta BP_P$, namely, the difference between the blood pressure at a dicrotic notch and the systolic blood pressure which were obtained from the waveform of arterial pressure and the dicrotic wave height $\Delta BP_D$, namely, the difference in blood pressure between the dicrotic notch and the peak of the dicrotic wave by using a pulse waveform monitor having the same structure as that of the pulse waveform monitor used in the eleventh embodiment. As a consequence, it was confirmed that administration of some types of medication, for example, a hypotensive, leads to a change in the effusion diastolic pressure as shown in the following.

Figure 63:
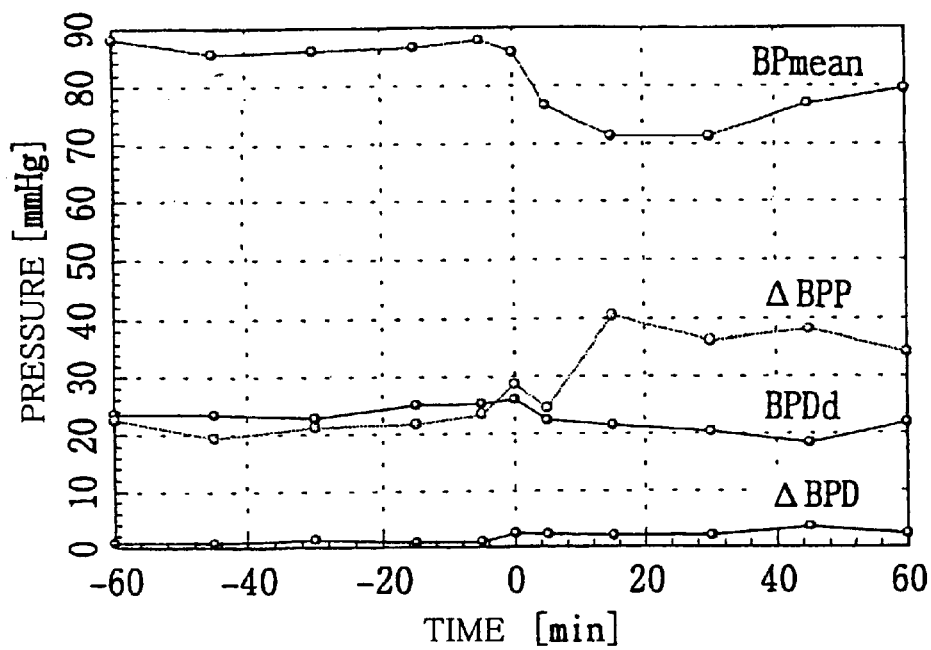
FIG. 63 is a graph showing a variation in the pressure of each portion in arterial pressure waveform with administration of an antihypertensive agent.
Figure 64:
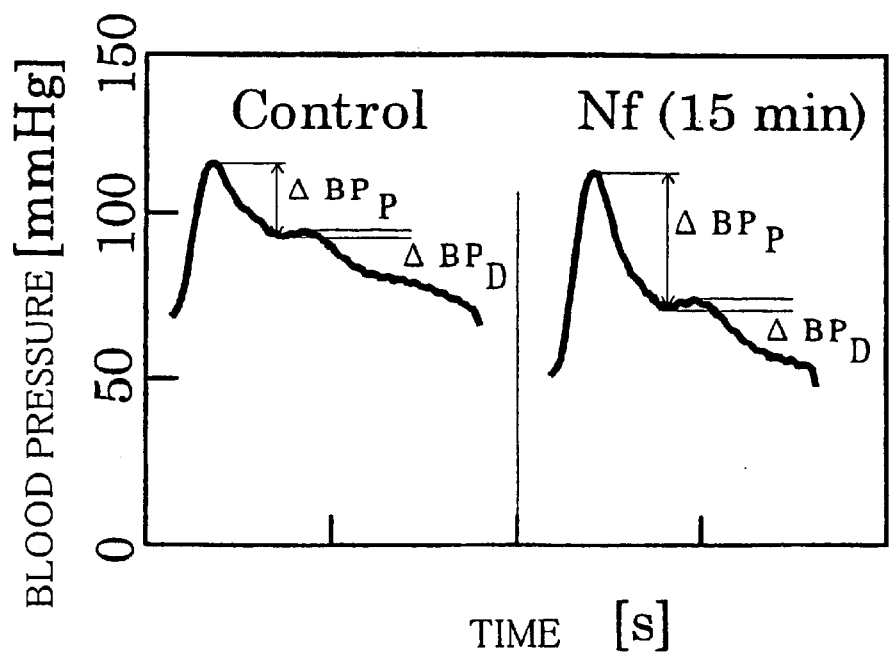
FIG. 64 is a view showing arterial waveforms before and after administration of an antihypertensive agent.

FIG. 63 is a graph showing the results of the mean blood pressure $BP_{mean}$, effusion diastolic pressure $\Delta BP_P$, dicrotic pressure difference $BP_{Dd}$ which is the pressure difference between the blood pressure at a dicrotic notch and the minimum blood pressure and dicrotic wave height $\Delta BP_D$ which is the difference in blood pressure between the dicrotic notch and the peak of the dicrotic wave during a period between 60 minutes before the administration and 60 minutes after the administration when nifezipine is administered as a hypotensive at time 0 (minute). In FIG. 64, the waveform named as "Control" is a waveform of arterial pressure of one beat as an average for 60 minutes before the administration of the hypotensive and the waveform named as "Nf" is a waveform of arterial pressure of one beat as an average for 10 seconds from 15 minutes after the administration of the hypotensive. It is seen clearly from these figures that the administration of the hypotensive leads to a fall in the mean blood pressure $BP_{mean}$, a rise in the effusion diastolic pressure $\Delta BP_P$ and an increase in the dicrotic wave height $\Delta BP_D$. This embodiment relates to a pharmacological action monitor structured on the basis of the result of the observation of such a pharmacological action.

13.2 Structure and Action of the Pharmacological Action Monitor

Figure 57:
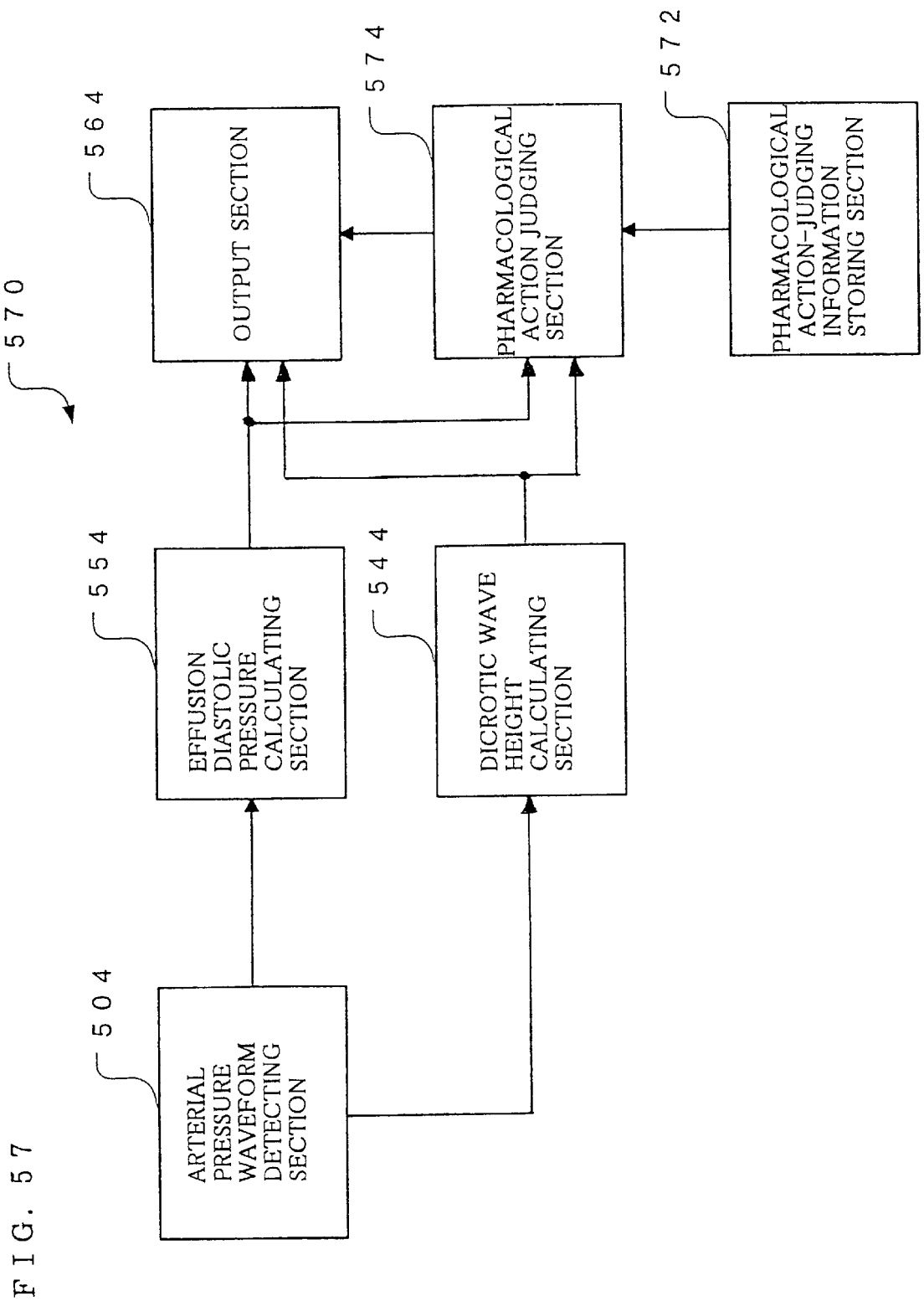
FIG. 57 is a block diagram showing the structure of a pharmacological action monitor of the twelfth embodiment.

A pharmacological action monitor 570, as shown in FIG. 57, is not provided with the dicrotic pressure difference ratio calculating section 548 and the mean blood pressure-pulse pressure ratio calculating section 552 which are provided in the pulse waveform monitor 540 shown in the eleventh embodiment. In the pharmacological action monitor 570, a pharmacological action judging section 574 is used in place of the pulse waveform judging section and a pharmacological action-judging information storing section 572 is used in place of the pulse waveform-judging information storing section. The pharmacological action monitor 570 has the same structure as the pulse waveform monitor 540 of the eleventh embodiment except for the above sections.

In the pharmacological action monitor 570 with such a structure, when the arterial pressure waveform detecting section 504 detects a waveform of arterial pressure, the information from the waveform is input to an effusion diastolic pressure calculating section 554 and a dicrotic wave height calculating section 544. The effusion diastolic pressure calculating section 554 calculates effusion diastolic pressure which is the difference between the systolic blood pressure (maximum blood pressure) and the dicrotic blood pressure and outputs the effusion diastolic pressure to the pharmacological action judging section 574 and to an output section 564. The dicrotic wave height calculating section 544 calculates a dicrotic wave height which is the difference in blood pressure between the dicrotic notch and the peak of a dicrotic wave and outputs the calculated data to the pharmacological action judging section 574 and to the output section 564.

The pharmacological action judging section 574 judges the pharmacological action from the input data of the effusion diastolic pressure and of the dicrotic wave height based on the pharmacological action judging information stored in the pharmacological action-judging information storing section 572 and outputs the result to the output section 564. The output section 564 outputs the values of the effusion diastolic pressure and dicrotic wave height and the result judged by the pharmacological action judging section in, for instance, image information via an LCD, sound information from a speaker and in the form of voltage.

In the pharmacological action monitor 570, a pulse wave detecting section for detecting a pulse waveform which is a wave of blood which is output from the heart and propagates through a blood vessel may be used in place of the arterial pressure waveform detecting section 504. In this case, the effusion diastolic pressure calculating section 554 and the dicrotic wave height calculating section 544 cannot calculate absolute blood pressure. Hence they can be replaced by effusion diastolic pressure ratio calculating section and dicrotic wave height ratio calculating section to calculate an effusion diastolic pressure ratio and a dicrotic wave height ratio which are normalized by pulse pressure, namely, the difference between systolic pressure and diastolic pressure respectively so that a comparison of data can be made exactly.

In this embodiment, the pharmacological action monitor 570 is provided with the effusion diastolic pressure calculating section 554 and the dicrotic wave height calculating section 544. However, a pharmacological action monitor may have a structure in which at least one of the effusion diastolic pressure calculating section 554 and the dicrotic wave height calculating section 544 is used.

14. Other Modifications

Having described embodiments of the present invention, the present invention is not limited to the aforementioned embodiments but various modifications may be made within the scope of the spirit of the invention and within an equivalent scope of the appended claims.

(1) In the foregoing first embodiment, the tidal wave-character extracting section 50 yields the tidal wave-character data TWD by (f2+f3+f4)/f1 and the dicrotic wave-character extracting section 60 yields the dicrotic wave-character data DWD by (f5+f6+f7)/f1. The present invention is not limited to the above and these sections may extract the characteristics of a tidal wave and dicrotic wave on the basis of any harmonic component as far as the harmonic component makes it possible to extract the characteristics of the tidal wave and dicrotic wave.

(2) In the aforementioned second embodiment, the time positions of the tidal wave and dicrotic wave are specified based on the pulse wave analysis data MKD. However, the present invention is not limited to the above but any method may be adopted as far as it can specify each time position. For instance, the signal MHj is differentiated to calculate its zero-cross point thereby determining the peak point of the signal MHj by which the time positions of the tidal wave and dicrotic wave are specified.

(3) In the above second embodiment, the frequency analysis of the signal MHj is made by undergoing wavelet transformation. A method may be adopted in which a window function is used to extract a tidal wave and a dicrotic wave from the signal MHj and the extracted tidal wave and dicrotic wave are each subjected to FFT treatment.

(4) In the first and second embodiments as aforementioned, a frequency analysis by FFT treatment (first embodiment) and a time frequency analysis by wavelet transformation (second embodiment) are made to extract the characteristics of a tidal wave and dicrotic wave. However, the present invention is not limited to the above but any measures may be used as far as these characteristics can be extracted based on the amplitudes of a tidal wave and dicrotic wave. For instance, a method may be adopted in which the signal MHj is subjected to two-step differentiation to intensify the peak of the signal MHj and the amplitudes of the tidal wave and dicrotic wave are calculated based on the resulting signal thereby extracting each of the amplitudes as the characteristics of each wave.

(5) In the sixth and seventh embodiments mentioned above, the first frequency correcting section and the second frequency correcting section are used. However, these structures may be omitted.

(6) The wavelet transformation and the inverse wavelet transformation described in the above embodiments may be carried out using a filter bank. FIG. 58 shows an instance of the structure of a filter bank used in the wavelet transformation. In the figure, the filter bank is structured in three stages and its basic unit consists of a high frequency filter 1A and a decimation filter 1C and a low frequency filter 1B and a decimation filter 1C. The high frequency filter 1A and the low frequency filter 1B divide a given frequency zone to output a high frequency component and a low frequency component respectively. Since it is assumed that the frequency zone of the pulse wave data MD is in the range between 0 Hz and 4 Hz in this embodiment, the pass band of the high frequency filter 1A of the first stage is designed to be in the range between 2 Hz and 4 Hz whereas the pass band of the low frequency filter 1B of the first stage is designed to be in the range between 0 Hz and 2 Hz. The decimation filter 1C thins out data every one sample.

When the data yielded in this manner is supplied to the next stage, the division of the frequency zone and the data-thinning operation are repeated to divide the frequency zone between 0 Hz and 4 Hz into eight zones thereby yielding data M1–M8.

The high frequency filter 1A and the low frequency filter 1B may be constituted of a transversal filter including a delay element (D flip-flop) in the inside thereof. Meanwhile, the human pulse rate is in the range between 40 and 200 and the frequency of the fundamental wave of the pulse waveform MH varies every moment corresponding to the condition of a living body. In this case, if the divided frequency zone is caused to be variable synchronously with the frequency of the fundamental wave, information following the condition of a dynamic living body can be obtained. For this, the divided frequency zone may be varied correspondingly by giving the pules waveform MH as a clock signal supplied to the transversal filter.

Among the pulse wave analysis data MKD, typical frequency components showing the characteristics of the pulse waveform MH are each frequency component of the fundamental wave, second harmonic wave and third harmonic wave. The pulse condition may be determined using part of the data M*1–M*8 output from the filter bank. In this case, if the filter bank is structured so as to synchronize with the pulse waveform MH as above-mentioned, part of the high frequency filter 1A, low. frequency filter 1B and decimation filter 1C may be omitted so that the structure can be simplified.

Figure 59:
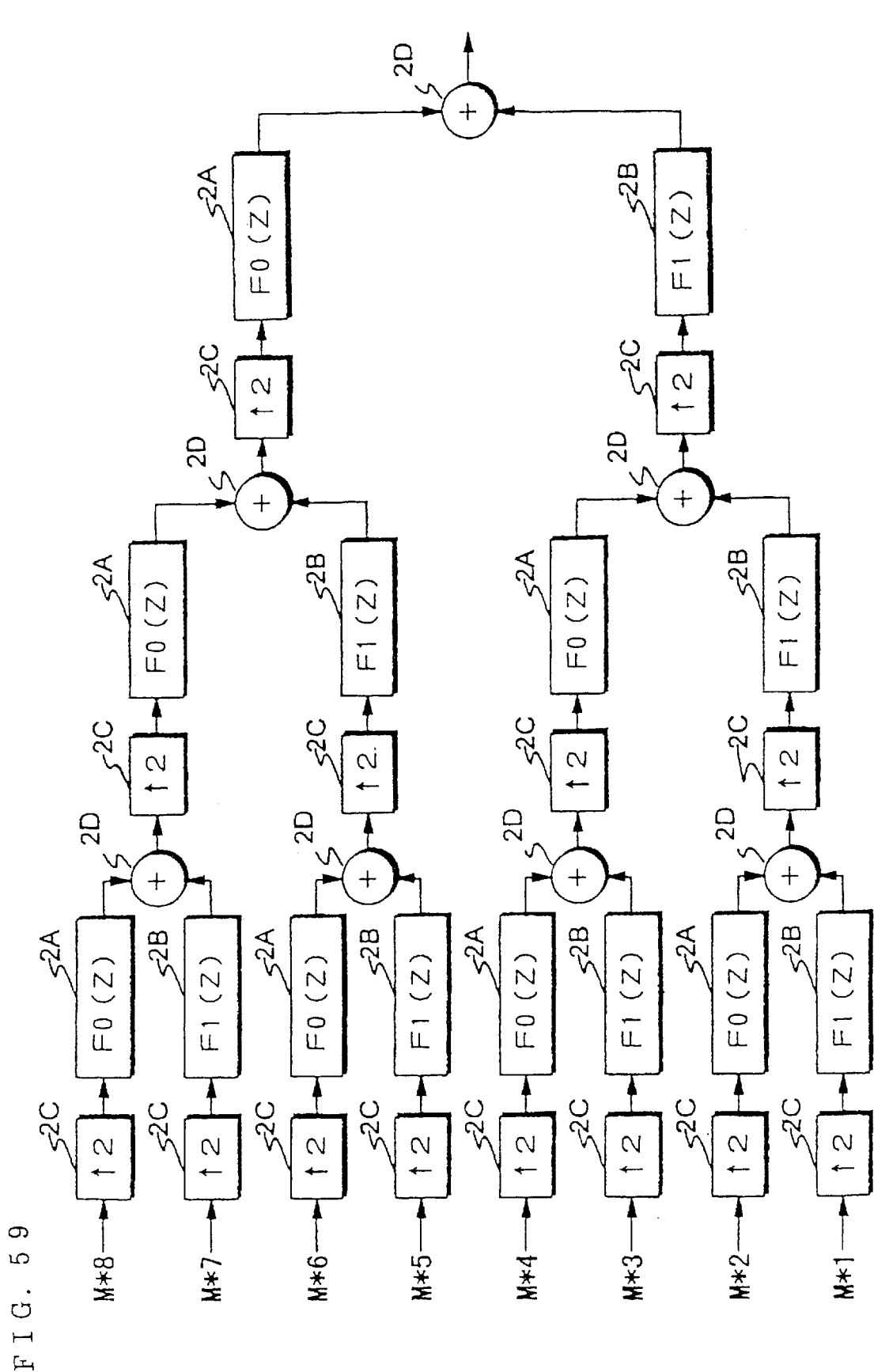
FIG. 59 is a block diagram showing a modification in which an inverse wavelet transformation section comprises a filter bank.

Next, FIG. 59 shows an instance of the structure of an inverse filter bank used to carry out the inverse wavelet transformation. In the figure, the filter bank has a three-stage structure with the basic unit consisting of a high frequency filter 2A and an interpolating filter 2C, a low frequency filter 2B and an interpolating filter 2C, and an adder 2D. The high frequency filter 2A and the low frequency filter 2B respectively divide a prescribed frequency zone to output a high frequency component and a low frequency component respectively. The interpolating filter 2C interpolates one sample for every two samples.

Figure 58:
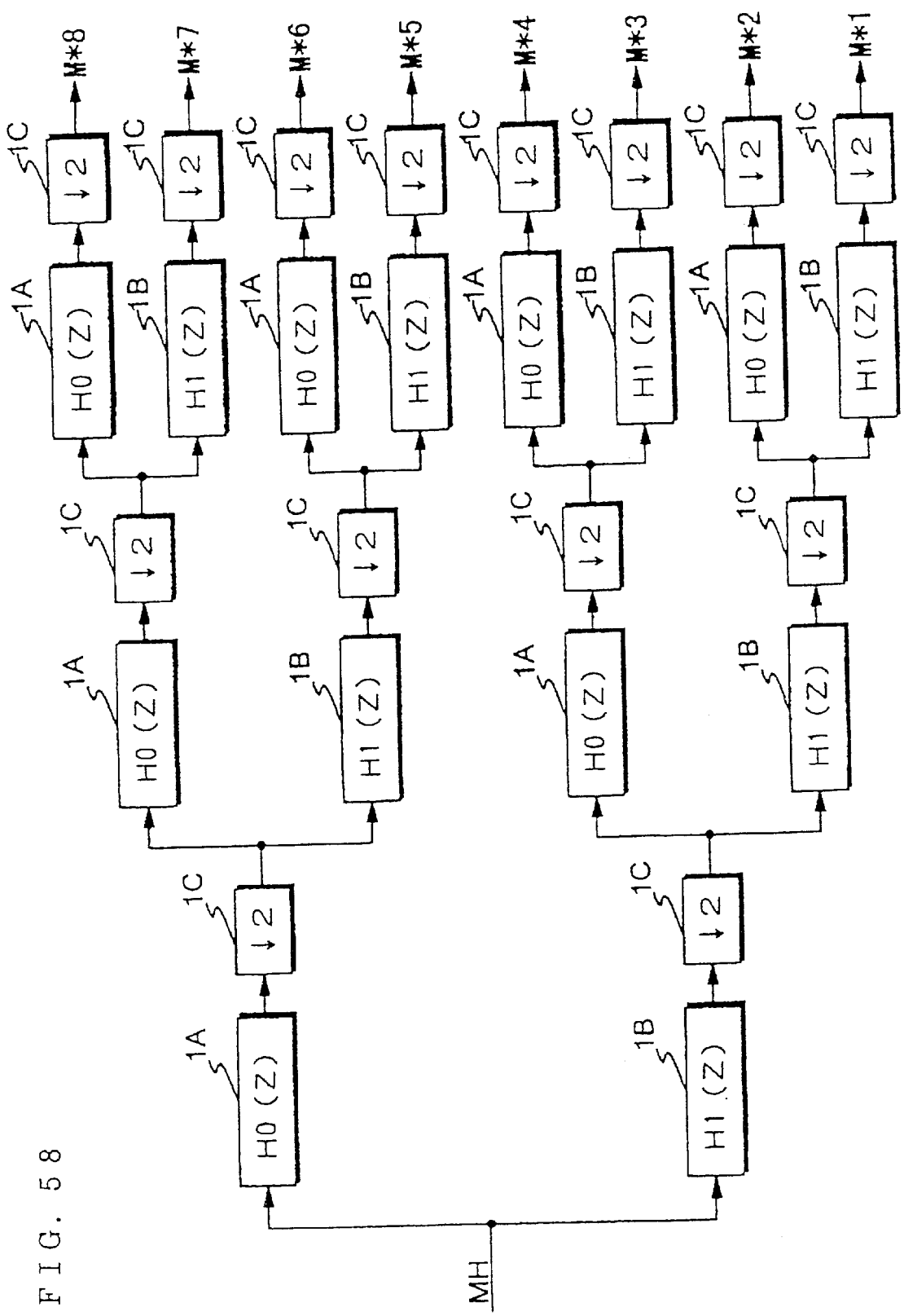
FIG. 58 is a block diagram showing a modification in which a wavelet transformation section comprises a filter bank.

Here, in order to reproduce a waveform, it is necessary to use a totally reproducible filter bank in the filter bank shown in FIG. 58 and in the filter bank shown in FIG. 59. In this case, the following relationship must be established between the characteristics of the high frequency filters 1A, 2A and the low frequency filters 1B, 2B.

$$H0(-Z)F0(Z)+H1(-Z)F1(Z)=0$$

$$H0(Z)F0(Z)+H1(-Z)F1(Z)=2Z^{-L}$$

The high frequency filter 2A and the low frequency filter 2B may be constituted of a transversal filter including a delay element (D flip-flop) in the inside thereof. In the case where a clock signal to be supplied is synchronized with the pulse waveform MH to make the divided zone variable synchronously with the frequency of the fundamental wave of the pulse waveform MH in the filter bank used in the wavelet transformation section 10, the clock signal may be supplied to the high frequency filter 2A and to the low frequency filter 2B.

(7) In the aforementioned embodiments, the display section 30 is described as an example of a measure for outputting information. Alternatively, as examples of measures for informing persons from an apparatus, those described in the following may be given. It is considered to be proper that these measures be classified according to a standard based on the five senses. These measures may be, of course, used not only singly but also in combinations of a plurality of measures. Additionally, the use of measures which appeal to the five senses other than the sense of sight enables even visually handicapped persons to understand the information. Likewise, the measures which appeal to the five senses other than the sense of hearing make it possible to notify persons with a hearing impairment. Thus an apparatus which is user-friendly even to handicapped persons can be provided.

First, notifying means which appeal to the sense of hearing include those intended either to inform the results of the analysis and diagnosis of a cardiac function or for the purpose of warning. For instance, these means are represented by piezoelectric elements and speakers as well as buzzers. To mention a specific example, one idea is that a person who is the subject of notification keeps a portable radio receiver close by and this receiver is accessed from the side of the apparatus when notification is intended. Moreover, in the notification using these devices, there are many cases where not only simple notification is made but also some further information is communicated. In this case, the level of informationsuchas mentionedbelow, for example, soundvolume, may be changed. These types of information include sound pitch, sound volume, sound tone, voice, types of music (programs).

Figure 60:
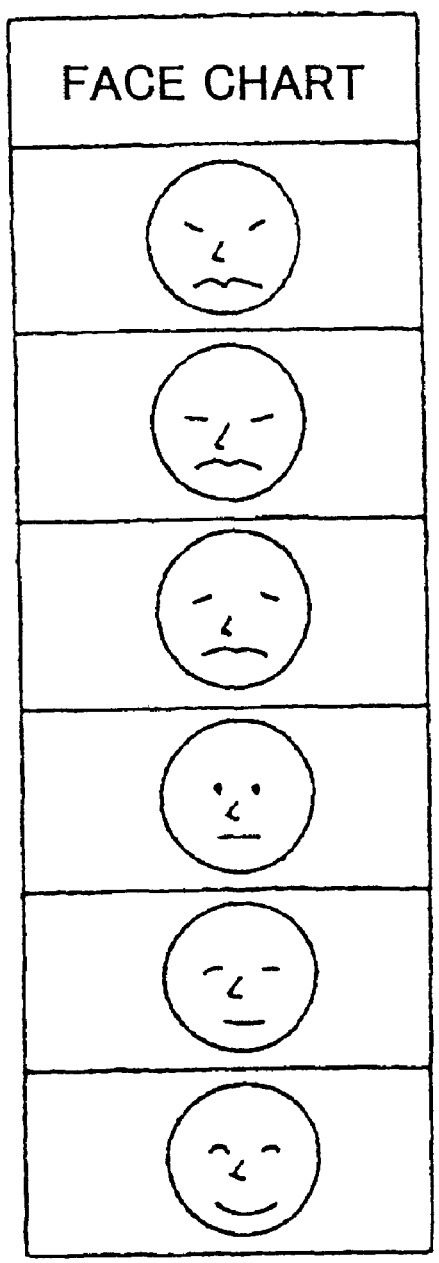
FIG. 60 is a face chart showing a modification of notification.

Second, the use of the notifying means which appeals to the sense of sight is for the purpose of communicating various messages and the results of measurement or for the purpose of warning from an apparatus. The following devices are considered suitable for attaining the above purposes. Specifically, displaying devices, CRTs (cathode ray tube displays), LCDs (liquid crystal displays), printers, X–Y plotters, and lamps are exemplified. A eyeglass-type projector is exemplified as a specific display device. In the notification, the variations mentioned below are considered. These variations include, for instance, display distinction between a digital display and an analog display in the notification of numerals, an indication by graphs, the concentration of a display color, and an indication by a bar graph, circular graph or a f ace chart in the case of transmitting numerals as is or as graded numerals. As an example of the face chart, that shown in FIG. 60 is given.

Then the use of notifying means which appeal to the sense of touch is considered, possibly for the purpose of warning. The following measures are adopted to achieve the above purpose: electrical stimulation produced by energizing a shape memory alloy projecting from the backface of a portable device such as a wrist watch , and mechanical stimulation produced by a projection formed in a portable device such as a wrist watch in such a manner that it can be freely run in and out from the backface of the device or by the vibration of a device body (for instance, the device body 100) of a wrist watch.

In addition, notifying means which appeal to the sense of smell may have a structure in which a mechanism for jetting a perfume or the like is provided in the apparatus so that the content of the notification corresponds to the fragrance of the perfume, to discharge a perfume corresponding to the content of the notification. incidentally, a micro-pump or the like is most suitable as the mechanism for jetting a perfume or the like.

These notifying means may be, of course, used either singly or in combinations of means.

(8) In the aforementioned embodiments, description is given using the pulse wave detecting section 10 as an example of the pulse wave detecting means. The present invention is not limited to the pulse wave detecting section 10 and any section may be adopted as far as it can detect pulsation.

For instance, those utilizing transmitted light may be adopted although the pulse wave detecting section 10 utilizes reflected light. In the meantime, light having a wavelength range less than 700 nm tends to transmit through a finger tissue with difficulty. In the case of using transmitted light, the light having a wavelength ranging from 600 nm to 1000 nm is emitted from an emission section and is allowed to transmit through tissue, blood vessel, and tissue in this order to detect a variation in the quantity of the transmitted light. Since the transmitted light is absorbed in hemoglobin in blood, the pulse waveform can be detected by detecting the change in quantity of the transmitted light.

In this case, in the emission section, a laser emitting diode of an InGaAs type (indium/gallium/arsenic) or GaAs type (gallium/arsenic) is preferably used. The extraneous light having wavelengths ranging from 600 nm to 1000 nm tends to transmit through tissue and hence the S/N ratio of the pulse signals is impaired when the extraneous light is introduced into a light receiving section. So a method may be adopted in which polarized laser light is emitted from an emission section and the transmitted light is accepted by a light receiving section through a polarizing filter. This enables detection of pulse signals free from the effect of extraneous light at a high S/N ratio.

Figure 61:
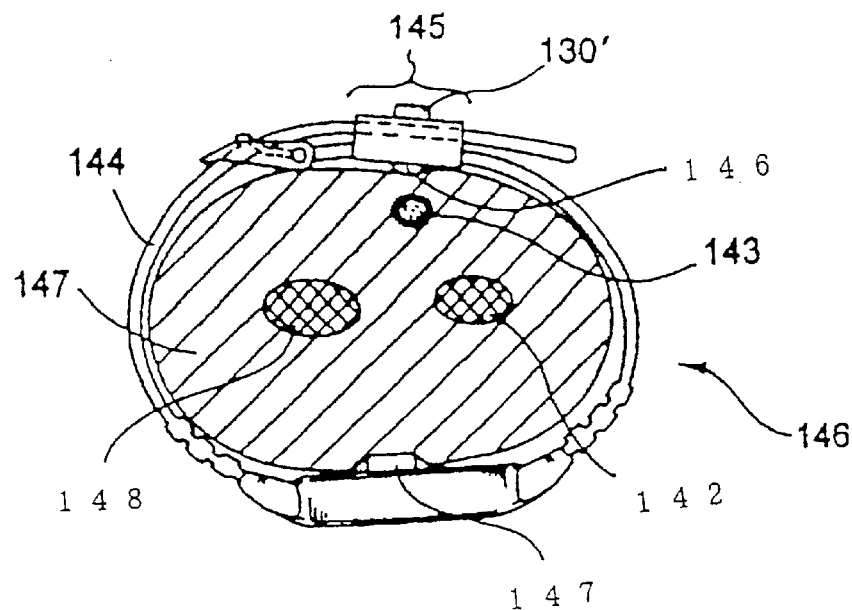
FIG. 61 is a view showing an example of a transmission-type photoelectric pulse wave sensor in a modification.

In this case, as shown in FIG. 61, an emission section 146 is arranged on the side of a fastener 145 and a light receiving section 147 is arranged on the side of the body of a wrist watch. The light emitted from the emission section 146 transmits through blood vessel 143, then passes through an area between a radius 148 and a cubitus 142 and reaches the light receiving section 147. In the case of using the transmitted light, it is necessary for the emitted light to transmit through tissue and hence its wavelength is preferably in a range between 600 nm and 1000 nm taking the absorption of the tissue into consideration.

Figure 62:
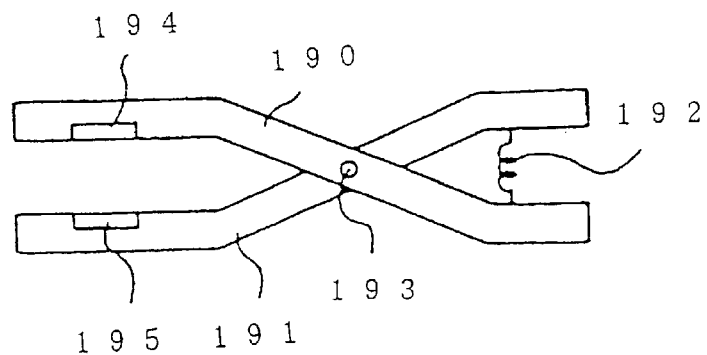
FIG. 62 is a view showing a modification in which a photoelectric pulse wave sensor is applied to a pair of eyeglasses.

FIG. 62 shows an instance using an ear lobe as a detecting position. A clamping member 190 and a clamping member 191 are activated by a spring 192 and can rotate around the center of an axis 193. The clamping members 190 and 191 are provided with a light emission section 194 and a light receiving section 195. When this pulse wave detecting section is used, a ear lobe is clamped with the clamping members 190 and 191 to detect a pulse wave.

(9) In the ninth embodiment, the body movement waveform TH is detected by the body movement detecting section 20 and the pulse wave analysis data MKDf is compared with the body movement analysis data TKDf to eliminate a body movement component and to thereby calculate the autocorrelation data RD based on which the pulse condition is determined. However, the body movement component tends to appear in a frequency zone lower than the frequency of the fundamental wave of the pulse waveform MH. Therefore, if a frequency zone higher than the frequency zone of the fundamental wave of the pulse waveform MH is selected as the focused frequency zone, the body movement detecting section 20, the waveform treating section 21, the judging section 22, the second wavelet transformation section 45 and the body movement component eliminating section 240 may be omitted. Specifically, in the pulse wave examination apparatus 1 as shown in FIG. 34, if a frequency zone higher than the frequency zone of the fundamental wave of the pulse waveform MH is selected as the focused frequency zone, an exact pulse condition can be determined even if body movement exists.

(10) The tenth and eleventh embodiments show instances in which a blood pressure monitor and a pulse waveform monitor are formed as apparatuses separated from each other. However, a structure may be adopted in which the blood pressure monitor shown in the tenth embodiment includes the pulse waveform monitor shown in the eleventh embodiment.

(11) The eleventh embodiment shows an instance in which the dicrotic wave height calculating section 544, the dicrotic pressure difference ratio calculating section 548, the mean blood pressure-pulse pressure ratio calculating section and the effusion diastolic pressure calculating section are provided in the pulse waveform monitor. However, at least one of these calculating sections may be provided.

What is claimed is:

1. A pulse wave examination apparatus comprising:
   a pulse wave detecting means for detecting a pulse waveform from a living body;
   a tidal wave-character extracting means for extracting the characteristics of a tidal wave from the pulse waveform to yield tidal wave-character information;
   a dicrotic wave-character extracting means for extracting the characteristics of a dicrotic wave from the pulse waveform to yield dicrotic wave-character information; and
   a pulse condition judging means for judging the pulse condition of the living body on the basis of the tidal wave-character information and the dicrotic wave-character information.

2. The pulse wave examination apparatus as defined in claim 1,
   wherein the tidal wave-character extracting means yields the tidal wave-character information on the basis of a variation in the amplitude in the time-domain of the tidal wave; and
   wherein the dicrotic wave-character extracting means yields the dicrotic wave-character information on the basis of a variation in the amplitude in the time-domain of the dicrotic wave.

3. The pulse wave examination apparatus as defined in claim 2,
   wherein the variations in the amplitude in the time-domain of the tidal wave and the dicrotic wave are calculated from the primary or secondary time derivative of the pulse waveform.

4. The pulse wave examination apparatus as defined in claim 1, further comprising a notification means for communicating the pulse condition judged by the pulse condition judging means.

5. A pulse wave examination apparatus comprising:
   a pulse wave detecting means for detecting a pulse waveform from a living body;
   a frequency analyzing means for performing a frequency analysis of the pulse waveform;
   a tidal wave-character extracting means for extracting the characteristics of a tidal wave from the result of the analysis of the frequency analyzing means to yield tidal wave-character information;
   a dicrotic wave-character extracting means for extracting the characteristics of a dicrotic wave from the result of the analysis of the frequency analyzing means to yield dicrotic wave-character information; and
   a pulse condition judging means for judging the pulse condition of the living body on the basis of the tidal wave-character information and the dicrotic wave-character information.

6. The pulse wave examination apparatus as defined in claim 5,
   wherein the tidal wave-character information extracting means specifies a period of the tidal wave in the pulse waveform and extracts the characteristics of the tidal wave from the tidal waveform on the basis of the result of the analysis of the frequency analyzing means in the period of the tidal wave to yield tidal wave-character information; and
   wherein the dicrotic wave-character information extracting means specifies a period of the dicrotic wave in the pulse waveform and extracts the characteristics of the dicrotic wave from the dicrotic waveform on the basis of the result of the analysis of the frequency analyzing means in the period of the dicrotic wave to yield dicrotic wave-character information.

7. The pulse wave examination apparatus as defined in claim 5, wherein the frequency analyzing means performs FFT treatment of the pulse waveform.

8. The pulse wave examination apparatus as defined in claim 5, wherein the frequency analyzing means performs wavelet transformation treatment of the pulse waveform.

9. A pulse wave examination apparatus comprising:
   a pulse wave detecting means for detecting a pulse waveform from the detecting position of a living body;
   an auto-correlation calculating means for calculating auto-correlation data giving the auto-correlation of the pulse waveform detected by the pulse wave detecting means; and
   a pulse condition-data yielding means for yielding pulse condition data giving the type of pulse waveform based on the auto-correlation data.

10. The pulse wave examination apparatus as defined in claim 9,
    wherein the pulse condition-data yielding means produces the pulse condition data by comparing the auto-correlation data with a prescribed threshold value.

11. The pulse wave examination apparatus as defined in claim 10,
    wherein the pulse condition-data yielding means comprises a minimum value detecting section for detecting the minimum value of the auto-correlation data during a period of one heart beat, and a comparing section for comparing the minimum value, detected by the minimum value detecting section, with the threshold value to yield the pulse condition data.

12. The pulse wave examination apparatus as defined in claim 10,
    wherein the pulse condition-data yielding means comprises a minimum value detecting section for detecting an average minimum value by averaging each minimum value of the auto-correlation data detected in each of plural heart beat periods, and a comparing section for comparing the average minimum value, detected by the minimum value detecting section, with the threshold value to yield the pulse condition data.

13. The pulse wave examination apparatus as defined in claim 9,
wherein the pulse condition-data yielding means comprises:
a time measuring section for comparing the auto-correlation data with a prescribed threshold value to measure a time interval in which the auto-correlation data exceeds or is less than the threshold value;
a calculating section for calculating the ratio of the time interval, measured by the time measuring section, to a period of one heart beat; and
a comparing section for comparing the result, calculated by the calculating section, with a prescribed threshold value to yield the pulse condition data.

14. The pulse wave examination apparatus as defined in claim 13,
wherein the calculating section calculates the ratio of the time interval, measured by the time measuring section, to a period of one heart beat and calculates the average of the calculated results.

15. The pulse wave examination apparatus as defined in claim 9,
wherein the pulse condition-data yielding means comprises a change rate calculating section for detecting the change rate of the auto-correlation data on the basis of the auto-correlation data, and a change rate comparing section for comparing the change rate, detected by the change rate calculating section, with a prescribed threshold value to yield the pulse condition data.

16. The pulse wave examination apparatus as defined in claim 15,
wherein the change rate comparing section detects a maximum value of the change rate and compares the maximum value of the change rate with the threshold value to yield the pulse condition data.

17. The pulse wave examination apparatus as defined in claim 9, wherein the pulse condition data yielding means comprises:
a minimum value detecting section for detecting the minimum value of the auto-correlation data in a period of one heart beat;
a first comparing section for comparing the minimum value, detected by the minimum value detecting section, with a prescribed first threshold value to yield pulse condition data indicating a Xuan mai when the minimum value is less than the first threshold value;
a time measuring section for comparing the auto-correlation data with a prescribed second threshold value to measure a time interval in which the auto-correlation data exceeds or is less than the second threshold value;
a calculating section for calculating the ratio of the time interval, measured by the time measuring section, to a period of one heart beat; and
a second comparing section for comparing the result, calculated by the calculating section, with a prescribed third threshold value to yield the pulse condition data indicating a Ping mai or a Hua mai.

18. The pulse wave examination apparatus as defined in claim 17, wherein the auto-correlation data is a coefficient of auto-correlation, and the first threshold value used in the comparing operation performed in the first comparing section is 0.25 approximately.

19. The pulse wave examination apparatus as defined in claim 17,
wherein the auto-correlation data is a coefficient of auto-correlation, and the second threshold value used in the comparing operation performed in the time measuring section is designed to be in a range between 0.4 and 0.8.

20. The pulse wave examination apparatus as defined in claim 9, wherein the pulse condition data yielding means comprises:
a minimum value detecting section for detecting the minimum value of the auto-correlation data in a period of one heart beat;
a first comparing section for comparing the minimum value, detected by the minimum value detecting section, with the first threshold value to yield pulse condition data indicating a Xuan mai when the minimum value is less than the first threshold value;
a variation calculating section for detecting a change rate of the auto-correlation data on the basis of the auto-correlation data; and
a second comparing section for comparing the change rate, calculated by the change rate calculating section, with a prescribed threshold value to yield the pulse condition data indicating a Ping mai or a Hua mai.

21. The pulse wave examination apparatus as defined in claim 9, further comprising;
a body movement detecting means for detecting the waveform of the body movement indicating the body movement of the living body; and
a body movement-component eliminating means for eliminating a body movement component from the pulse waveform to yield a body movement-eliminated pulse waveform, said body movement component in the pulse waveform generated on the basis of the body movement waveform;
wherein the auto-correlation calculating means calculates auto-correlation data giving auto-correlation on the basis of the body movement-eliminated pulse waveform in place of the pulse waveform.

22. The pulse wave examination apparatus as defined in claim 21, further comprising judging means for judging the presence of body movement of the living body on the basis of the body movement waveform detected by the body movement detecting means,
wherein the body movement-component eliminating means stops the body movement eliminating operation when the judging means shows the absence of body movement to output the pulse waveform in place of the body movement-eliminated pulse waveform.

23. The pulse wave examination apparatus as defined in claim 9, further comprising:
a first wavelet transformation means for performing wavelet transformation of the pulse waveform detected by the pulse wave detecting means to yield pulse wave analysis data for every frequency zone;
a body movement detecting means for detecting the movement of the living body to output the waveform of the body movement;
a second wavelet transformation means for performing wavelet transformation of the waveform of the body movement detected by the body movement detecting means to yield body movement analysis data for every frequency zone;

a body movement component eliminating means for subtracting the body movement analysis data from the pulse wave analysis data to yield body movement-eliminated pulse wave analysis data; and an inverse wavelet transformation means for performing inverse wavelet transformation of the body movement-eliminated pulse wave analysis data to yield a body movement-eliminated pulse waveform;

wherein the auto-correlation calculating means calculates auto-correlation data giving auto-correlation on the basis of the body movement-eliminated pulse waveform in place of the pulse waveform.

24. The pulse wave examination apparatus as defined in claim 9, further comprising:

a wavelet transformation means for performing wavelet transformation of the pulse waveform detected by the pulse waveform detecting means to yield pulse wave analysis data for every frequency zone;

a body movement component eliminating means for eliminating a prescribed frequency component corresponding to a body movement among the pulse wave analysis data to yield body movement-eliminated pulse wave analysis data; and an inverse wavelet transformation means for performing inverse wavelet transformation of the body movement-eliminated pulse wave analysis data to yield a body movement-eliminated pulse waveform;

wherein the auto-correlation calculating means calculates auto-correlation data giving auto-correlation on the basis of the body movement-eliminated pulse waveform in place of the pulse waveform.

25. The pulse wave examination apparatus as defined in claim 9, further comprising a notification means for communicating the pulse condition data yielded by the pulse condition data yielding means.

26. A pulse wave examination apparatus comprising:

a pulse wave detecting means for detecting a pulse waveform from the detecting position of a living body;

a wavelet transformation means for performing wavelet transformation of the pulse waveform detected by the pulse wave detecting means to yield pulse wave analysis data for every frequency zone;

an auto-correlation calculating means for calculating auto-correlation data giving auto-correlation of the pulse wave analysis data in a given frequency zone; and a pulse condition data yielding means for yielding a pulse condition data giving the type of pulse waveform on the basis of the auto-correlation data.

27. A pulse wave examination apparatus comprising:

a pulse wave detecting means for detecting a pulse waveform from the detecting position of a living body;

a first wavelet transformation means for performing wavelet transformation of the pulse waveform detected by the pulse wave detecting means to yield pulse wave analysis data for every frequency zone;

a body movement detecting means for detecting the movement of the living body to output the waveform of the body movement;

a second wavelet transformation means for performing wavelet transformation of the waveform of the body movement detected by the body movement detecting means to yield body movement analysis data for every frequency zone;

a body movement component eliminating means for subtracting the body movement analysis data from the pulse wave analysis data to yield body movement-eliminated pulse wave analysis data;

an auto-correlation calculating means for calculating auto-correlation data giving auto-correlation of the body movement-eliminated pulse wave analysis data in a given frequency zone; and a pulse condition data yielding means for yielding pulse condition data giving the type of pulse waveform on the basis of the auto-correlation data.

28. A pulse wave examination apparatus comprising:

a pulse wave detecting means for detecting a pulse waveform from a detection position of a living body;

a wavelet transformation means for performing wavelet transformation of the pulse waveform detected by the pulse wave detecting means to yield pulse wave analysis data for every frequency zone;

a body movement component eliminating means for eliminating a prescribed frequency component corresponding to a body movement to yield body movement-eliminated pulse wave analysis data;

an auto-correlation calculating means for calculating auto-correlation data giving auto-correlation of the body movement-eliminated pulse wave analysis data in a given frequency zone; and a pulse condition data yielding means for yielding a pulse condition data giving the type of pulse waveform on the basis of the auto-correlation data.

29. A blood pressure monitor comprising:

an arterial pressure waveform detecting section for measuring blood pressure in an artery continuously to detect a waveform of arterial pressure; and a mean blood pressure calculating section for calculating the mean blood pressure on the basis of the waveform of arterial pressure.

30. The blood pressure monitor as defined in claim 29, further comprising a pulse pressure calculating section for calculating pulse pressure which is the pressure difference between the maximum blood pressure and the minimum blood pressure on the basis of the waveform of arterial pressure.

31. The blood pressure monitor as defined in claim 30, further comprising a blood pressure conversion section for converting the waveform of arterial pressure detected by the arterial pressure waveform detecting section into the waveform of cardiac-position arterial pressure which is a waveform of arterial pressure at a position corresponding to the height of a heart;

wherein the mean blood pressure calculating section calculates the mean blood pressure on the basis of the waveform of cardiac-position arterial pressure; and wherein the pulse pressure calculating section calculating the pulse pressure on the basis of the waveform of cardiac-position arterial pressure.

32. The blood pressure monitor as defined in claim 30, further comprising:

a blood pressure-judging information storing section for storing blood pressure-judging information in advance; and a blood pressure judging section for judging blood pressure on the basis of at least one of the mean blood pressure and the pulse pressure and on the blood pressure-judging information.

33. The blood pressure monitor as defined in claim 30, further comprising an output section for outputting at least one piece of information corresponding to the mean blood pressure, to the pulse pressure and to the blood pressure judgment.

34. A blood pressure monitor comprising:
- an arterial pressure waveform detecting section for measuring blood pressure in an artery continuously to detect a waveform of arterial pressure; and
- a pulse pressure calculating section for calculating pulse pressure, which is the pressure difference between the maximum blood pressure and the minimum blood pressure, on the basis of the waveform of arterial pressure.

35. The blood pressure monitor as defined in claim 34, further comprising:
- a maximum blood pressure calculating section for calculating the maximum blood pressure on the basis of the pulse pressure; and
- a minimum blood pressure calculating section for calculating the minimum blood pressure on the basis of the pulse pressure and the maximum blood pressure.

36. A pulse waveform monitor comprising:
- an arterial pressure waveform detecting section for measuring blood pressure in an artery continuously to detect a waveform of arterial pressure; and
- a dicrotic wave height calculating section for calculating a dicrotic wave height which is the difference in blood pressure between a dicrotic notch and the peak of a dicrotic wave which are obtained from the waveform of arterial pressure.

37. The pulse waveform monitor as defined in claim 36, further comprising a dicrotic pressure difference ratio calculating section for calculating, based on the waveform of arterial pressure, the ratio of a dicrotic pressure difference, which is the pressure difference between blood pressure at a dicrotic notch and the minimum blood pressure, to a pulse pressure which is the pressure difference between the maximum blood pressure and the minimum blood pressure.

38. The pulse waveform monitor as defined in claim 37, further comprising a mean blood pressure-pulse pressure ratio calculating section for calculating, based on the waveform of arterial pressure, the mean blood pressure-pulse pressure ratio which is the ratio of the mean blood pressure to pulse pressure which is the pressure difference between the maximum blood pressure and the minimum blood pressure.

39. The pulse waveform monitor as defined in claim 37, further comprising:
- a pulse waveform-judging information storing section for storing pulse waveform-judging information in advance; and
- a pulse waveform judging section for judging the pulse waveform on the basis of the dicrotic wave height, the dicrotic pressure difference ratio and the pulse waveform-judging information.

40. The pulse waveform monitor as defined in claim 37, further comprising an output section for outputting at least one piece of information corresponding to the dicrotic wave height, to the dicrotic pressure difference ratio, and to the pulse waveform.

41. The pulse waveform monitor as defined in claim 38, further comprising a blood pressure conversion section for converting the waveform of arterial pressure detected by the arterial pressure waveform detecting section into the waveform of cardiac-position arterial pressure which is a waveform of arterial pressure at a position corresponding to the height of a heart;
- wherein the dicrotic wave height calculating section calculates, based on the waveform of cardiac-position arterial pressure, a dicrotic wave height which is the pressure difference in blood pressure between a dicrotic notch and the peak of a dicrotic wave;
- wherein the dicrotic pressure difference ratio calculating section calculates, based on the wave form of cardiac-position arterial pressure, the ratio of a dicrotic pressure difference, which is the pressure difference between the blood pressure at a dicrotic notch and the minimum blood pressure, to a pulse pressure which is the pressure difference between the maximum blood pressure and the minimum blood pressure; and
- wherein the mean blood pressure-pulse pressure ratio calculating section calculates, based on the waveform of cardiac-position arterial pressure, the mean blood pressure-pulse pressure ratio which is the ratio of the mean blood pressure to a pulse pressure which is the pressure difference between the maximum blood pressure and the minimum blood pressure.

42. The pulse waveform monitor as defined in claim 38, further comprising:
- a pulse waveform-judging information storing section for storing pulse waveform-judging information in advance; and
- a pulse waveform judging section for judging the pulse waveform on the basis of the dicrotic wave height, the dicrotic pressure difference ratio, the mean blood pressure-pulse pressure ratio, and the pulse waveform-judging information.

43. The pulse waveform monitor as defined in claim 38, further comprising an output section for outputting at least one piece of information corresponding to the dicrotic wave height, to the dicrotic pressure difference ratio, to the mean blood pressure-pulse pressure ratio, and to the pulse waveform.

44. The pulse waveform monitor as defined in claim 36, further comprising:
- a pulse waveform-judging information storing section for storing pulse waveform-judging information in advance; and
- a pulse waveform judging section for judging the waveform of a pulse wave on the basis of the dicrotic wave height and the pulse waveform-judging information.

45. The pulse waveform monitor as defined in claim 36, further comprising an output section for outputting at least one piece of information corresponding to the dicrotic wave height and to the pulse waveform.

46. A pulse waveform monitor comprising:
- a pulse waveform detecting section for detecting the pulse waveform from a living body; and
- a dicrotic pressure difference ratio calculating section for calculating, based on the pulse waveform, the dicrotic pressure difference ratio which is the ratio of the pressure difference between a dicrotic pressure and the minimum pressure, to a pulse pressure which is a pressure difference between the maximum pressure and the minimum pressure.

47. A pulse waveform monitor comprising:
- a pulse waveform detecting section for detecting a pulse waveform from a living body; and
- a mean pressure-pulse pressure ratio calculating section for calculating, based on the pulse waveform, the ratio of the mean pressure to pulse pressure which is a pressure difference between a maximum pressure and a minimum pressure.

48. A blood pressure monitor comprising:
- an arterial pressure waveform detecting section for measuring blood pressure in an artery continuously to detect a waveform of arterial pressure;

a mean blood pressure calculating section for calculating the mean blood pressure on the basis of the waveform of arterial pressure; and a dicrotic wave height calculating section for calculating, based on the waveform of arterial pressure, a dicrotic wave height which is the difference in blood pressure between a dicrotic notch and the peak of a dicrotic wave.

49. A blood pressure monitor comprising:

an arterial pressure waveform detecting section for measuring blood pressure in an artery continuously to detect a waveform of arterial pressure;

a mean blood pressure calculating section for calculating the mean blood pressure on the basis of the waveform of arterial pressure; and a dicrotic pressure difference ratio calculating section for calculating, based on the waveform of arterial pressure, the dicrotic pressure difference ratio which is the ratio of a dicrotic pressure difference, which is the pressure difference between the blood pressure at a dicrotic notch and the minimum blood pressure, to a pulse pressure which is the pressure difference between the maximum blood pressure and the minimum blood pressure.

50. A blood pressure monitor comprising:

an arterial pressure waveform detecting section for measuring blood pressure in an artery continuously to detect a waveform of arterial pressure;

a mean blood pressure calculating section for calculating the mean blood pressure on the basis of the waveform of arterial pressure; and a mean blood pressure-pulse pressure ratio calculating section for calculating, based on the waveform of arterial pressure, the mean blood pressure-pulse pressure ratio which is the ratio of the mean blood pressure to a pulse pressure which is the pressure difference between the maximum blood pressure and the minimum blood pressure.

51. A blood pressure monitor comprising:

an arterial pressure waveform detecting section for measuring blood pressure in an artery continuously to detect a waveform of arterial pressure;

a pulse pressure calculating section for calculating pulse pressure, which is the pressure difference between the maximum blood pressure and the minimum blood pressure, on the basis of the waveform of arterial pressure; and a dicrotic wave height calculating section for calculating, based on the waveform of arterial pressure, the dicrotic wave height which is the difference in blood pressure between a dicrotic notch and the peak of a dicrotic wave.

52. A blood pressure monitor comprising:

an arterial pressure waveform detecting section for measuring blood pressure in an artery continuously to detect a waveform of arterial pressure;

a pulse pressure calculating section for calculating pulse pressure, which is the pressure difference between the maximum blood pressure and the minimum blood pressure, on the basis of the waveform of arterial pressure; and a dicrotic pressure difference ratio calculating section for calculating, based on the waveform of arterial pressure, the dicrotic pressure difference ratio which is the ratio of a dicrotic pressure difference, which is the pressure difference between the blood pressure at a dicrotic notch and the minimum blood pressure, to a pulse pressure which is the pressure difference between the maximum blood pressure and the minimum blood pressure.

53. A blood pressure monitor comprising:

an arterial pressure waveform detecting section for measuring blood pressure in an artery continuously to detect a waveform of arterial pressure;

a pulse pressure calculating section for calculating pulse pressure, which is the pressure difference between the maximum blood pressure and the minimum blood pressure, on the basis of the waveform of arterial pressure; and a mean blood pressure-pulse pressure ratio calculating section for calculating, based on the waveform of arterial pressure, the mean blood pressure-pulse pressure ratio which is the ratio of the mean blood pressure to a pulse pressure which is the pressure difference between the maximum blood pressure and the minimum blood pressure.

54. A pulse waveform monitor comprising:

an arterial pressure waveform detecting section for measuring blood pressure in an artery continuously to detect a waveform of arterial pressure; and an ejection diastolic pressure calculating section for calculating, based on the waveform of arterial pressure, ejection diastolic pressure which is the pressure difference between systolic blood pressure and the blood pressure at a dicrotic notch.

55. The pulse waveform monitor as defined in claim 54, further comprising:

a pulse waveform-judging information storing section for storing pulse waveform-judging information in advance; and a pulse waveform judging section for judging the pulse waveform on the basis of the ejection diastolic pressure and the pulse waveform-judging information.

56. A pulse waveform monitor comprising:

a pulse wave detecting section for detecting a pulse waveform from a living body; and an ejection diastolic pressure ratio calculating section for calculating, based on the pulse waveform, the ejection diastolic pressure ratio which is the ratio of ejection diastolic pressure, which is the pressure difference between systolic pressure and dicrotic pressure, to pulse pressure which is the pressure difference between systolic pressure and diastolic pressure.

57. The pulse waveform monitor as defined in claim 56, further comprising:

a pulse waveform-judging information storing section for storing pulse waveform-judging information in advance; and a pulse waveform judging section for judging the pulse waveform on the basis of the ejection diastolic pressure ratio and the pulse waveform-judging information.

58. A pharmacological action monitor comprising:

an arterial pressure waveform detecting section for measuring blood pressure in an artery continuously to detect a waveform of arterial pressure; and an ejection diastolic pressure calculating section for calculating, based on the waveform of arterial pressure, ejection diastolic pressure which is the pressure difference between systolic blood pressure and blood pressure at a dicrotic notch.

59. The pharmacological action monitor as defined in claim 58, further comprising a dicrotic wave height calculating section for calculating, based on the waveform of arterial pressure, a dicrotic wave height which is the blood pressure difference between a dicrotic notch and the peak of a dicrotic wave.

60. A pharmacological action monitor comprising:
- a pulse wave detecting section for detecting a pulse waveform from a living body; and
- an ejection diastolic pressure ratio calculating section for calculating the ejection diastolic pressure ratio which is the ratio of the ejection diastolic pressure, which is the pressure difference between systolic pressure and dicrotic pressure, to a pulse pressure which is the pressure difference between the diastolic pressure and the systolic pressure.

61. The pharmacological action monitor as defined in claim 60, further comprising a dicrotic wave height calculating section for calculating, based on the pulse waveform, a dicrotic wave height ratio which is the ratio of a dicrotic wave height, which is the difference in pressure between a dicrotic notch and the peak of a dicrotic wave, to pulse pressure which is the pressure difference between systolic pressure and diastolic pressure.

* * * * *

UNITED STATES PATENT AND TRADEMARK OFFICE
CERTIFICATE OF CORRECTION

PATENT NO. : 6,293,915 B1
DATED : September 25, 2001
INVENTOR(S) : Kazuhiko Amano et al.

It is certified that error appears in the above-identified patent and that said Letters Patent is hereby corrected as shown below:

Title page,
Item [30], "Foreign Application Priority Data" change "July 12, 1998" to -- July 13, 1998 --

Signed and Sealed this

Seventh Day of May, 2002

Attest:

JAMES E. ROGAN
Attesting Officer
Director of the United States Patent and Trademark Office